US012667101B2

(12) United States Patent
Muir et al.

(10) Patent No.: US 12,667,101 B2
(45) Date of Patent: Jun. 30, 2026

(54) PICOLINAMIDE DERIVATIVES USEFUL AS AGRICULTURAL FUNGICIDES

(71) Applicant: GLOBACHEM NV, Sint-Truiden (BE)

(72) Inventors: Calum Muir, Macclesfield (GB); Ryan Burgin, Macclesfield (GB); Linda Jordan, Macclesfield (GB); Victoria Jackson, Macclesfield (GB)

(73) Assignee: GLOBACHEM NV, Sint-Truiden (BE)

( * ) Notice: Subject to any disclaimer, the term of this patent is extended or adjusted under 35 U.S.C. 154(b) by 1160 days.

(21) Appl. No.: 17/629,344

(22) PCT Filed: Jul. 23, 2020

(86) PCT No.: PCT/EP2020/070743

§ 371 (c)(1),
(2) Date: Jan. 21, 2022

(87) PCT Pub. No.: WO2021/013910

PCT Pub. Date: Jan. 28, 2021

(65) Prior Publication Data

US 2022/0256855 A1 Aug. 18, 2022

(30) Foreign Application Priority Data

Jul. 24, 2019 (GB) ...................................... 1910586
Jan. 28, 2020 (GB) ...................................... 2001180

(51) Int. Cl.

| | |
|---|---|
| ***C07D 401/12*** | (2006.01) |
| ***A01N 43/42*** | (2006.01) |
| ***A01N 43/90*** | (2006.01) |
| ***A01P 3/00*** | (2006.01) |
| ***C07D 401/14*** | (2006.01) |
| ***C07D 498/04*** | (2006.01) |
| ***C07D 498/14*** | (2006.01) |

(52) U.S. Cl.

CPC ............. *A01N 43/90* (2013.01); *A01N 43/42* (2013.01); *A01P 3/00* (2021.08); *C07D 401/12* (2013.01); *C07D 401/14* (2013.01); *C07D 498/04* (2013.01)

(58) Field of Classification Search

CPC ... C07D 401/12; C07D 401/14; C07D 498/14
See application file for complete search history.

(56) References Cited

U.S. PATENT DOCUMENTS

| | | | |
|---|---|---|---|
| 7,183,278 B1 | 2/2007 | Imamura et al. | |
| 8,003,799 B2 | 8/2011 | Nieto-Roman et al. | |
| 2006/0040995 A1 | 2/2006 | Bacque et al. | |
| 2007/0254894 A1 | 11/2007 | Kane et al. | |
| 2015/0191438 A1 | 7/2015 | Chang et al. | |

FOREIGN PATENT DOCUMENTS

| | | |
|---|---|---|
| CN | 1329596 | 1/2002 |
| CN | 1394202 | 1/2003 |
| EA | 22145 | 11/2015 |
| EP | 1134214 | 9/2001 |
| JP | 2003-519215 | 10/2012 |
| WO | 2000026191 | 5/2000 |
| WO | 200149667 | 7/2001 |
| WO | WO 2019006157 | 1/2019 |
| WO | 2019141980 | 7/2019 |

OTHER PUBLICATIONS

Search Report, dated Jan. 23, 2020, received in Priority Application No. GB 1910586.5.
Bastin, RJ et al., "Salt Selection and Optimisation Procedures for Pharmaceutical New Chemical Entities", *Organic Process Research & Development*, 4, 427-435, 2000.
Popova, LM et al., "Chemical means for plant protection", Textbook, *St. Petersburg State Technological University of Plants*, St. Petersburg, pp. 1, 9, 13, 2009. (English Machine Translation Provided).
Shvetsov, SV, et al., "Modern calculated methods of assessment of pesticide and herbicide activity of organic compounds", *Bashkir Chemical Journal*, 20(2); pp. 134-135, 2013. (English Abstract).
Indian Search Report and Written Opinion issued in corresponding Indian application No. 202217007769 mailed Feb. 16, 2023.
Zhang, Chengxia et al., "Fungicide Seed Dressing to Control Lawn Grass Diseases—Research Progress on Harm", Acta Prataculturae Sinica, vol. 14, No. 6, Dec. 30, (with English abstract) 2005.

*Primary Examiner* — Brian E Mcdowell
(74) *Attorney, Agent, or Firm* — NORTON ROSE FULBRIGHT US LLP

(57) ABSTRACT

The present invention relates to picolinic acid derivatives that are useful in treating fungal diseases, particularly in plants.

(I)

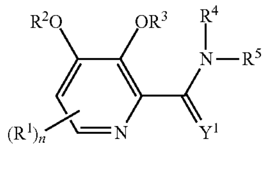

24 Claims, No Drawings

PICOLINAMIDE DERIVATIVES USEFUL AS AGRICULTURAL FUNGICIDES

CROSS-REFERENCE TO RELATED APPLICATIONS

The present application is a U.S. National Stage entry under 35 U.S.C. § 371 of International Application No. PCT/EP2020/070743, filed on Jul. 23, 2020, designating the United States of America and published in English on Jan. 28, 2021, which in turn claims priority to G.B. Application Nos. 2001180.5 and 1910586.5, filed on Jan. 28, 2020 and Jul. 24, 2019, respectively, each of which is hereby incorporated by reference in its entirety.

The present invention relates to picolinic acid derivatives that are useful in treating fungal disease.

Given the global increase in demand for food, there is an international need for new treatments to reduce food crop losses to disease, insects and weeds. Over 40% of crops are lost before harvest, and 10% post harvest, worldwide. Losses have actually increased since the mid-1990s.

A new threat contributing to this is the emergence of chemical-resistant organisms, for example, glyphosate-resistant weeds in the USA and strobilurin-resistant strains of *Septoria* fungal species.

Recent research also suggests that the geographical spread of many crop pests and diseases is increasing, possibly as a result of global warming.

Certain picolinic acid derivatives are shown to be useful in treating fungal disease in PCT/GB2019/050111 (published as WO2019/141980).

An aim of certain embodiments of the present invention is to provide pesticides (e.g. fungicides) which have activity either non-selectively, i.e. broad spectrum activity, or which are active specifically against selective target organisms.

An aim of certain embodiments of the present invention is to provide compounds which are less persistent in the environment after use than prior art compounds. Alternatively or additionally, the compounds of the present invention may be less prone to bioaccumulation once in the food chain than prior art compounds.

Another aim of certain embodiments of the invention is to provide compounds which are less harmful to humans than prior art compounds. Alternatively or additionally, the compounds of the invention may be less harmful than prior art compounds to one or more of the following groups: amphibians, fish, mammals (including domesticated animals such as dogs, cats, cows, sheep, pigs, goats, etc.), reptiles, birds, and beneficial invertebrates (e.g. bees and other insects, or worms), beneficial nematodes, beneficial fungi and nitrogen-fixing bacteria.

The compounds of the invention may be as active as or more active than prior art compounds. They may have activity against organisms which have developed a resistance to prior art compounds. However, the present invention may also concern compounds which have a lower or similar level of activity relative to that of the prior art compounds. These lower activity compounds are still effective as fungicides but may have other advantages relative to existing compounds such as, for example, a reduced environmental impact.

The compounds of the invention may be more selective than prior art compounds, i.e. they may have better, similar or even slightly lower activity than prior art compounds against target species but have a significantly lower activity against non-target species (e.g. the crops which are being protected).

Certain embodiments of the invention provide compounds that achieve one or more of the above aims. The compounds may be active in their own right or may metabolise or react in aqueous media to yield an active compound.

SUMMARY OF THE INVENTION

In a first aspect of the invention is provided a compound of formula I, or an agronomically acceptable salt or N-oxide thereof:

I

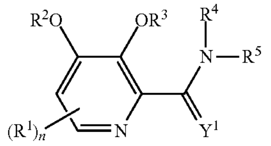

$Y^1$ is independently selected from O or S;

$R^1$, $R^{5a}$ and $R^{15}$ are each independently at each occurrence selected from $C_1$-$C_6$-alkyl, $C_1$-$C_6$-haloalkyl, $C_3$-$C_6$-cycloalkyl, halogen, nitro, $OR^{11}$, $SR^{12}$, $OS(O)_2R^{12}$, $S(O)_2R^{12}$, $C(O)OR^{12}$, $C(O)NR^{12}R^{12}$, $C(O)R^{12}$, $S(O)_2NR^{12}R^{12}$, $S(O)(NR^{12})R^{12}$, $S(O)R^{12}$, cyano, $C_2$-$C_6$-alkenyl, $C_2$-$C_6$-alkynyl, and $NR^{12}R^{13}$;

$R^2$ and $R^3$ are each independently selected from H, $C_1$-$C_4$-alkyl, $C_3$-$C_6$-cycloalkyl, $C(O)R^1$, $C(O)OR^{14}$, $CH_2OC(O)R^{14}$ and $CH_2OC(O)OR^{14}$;

$R^4$ is independently at each occurrence selected from: H, $C_3$-$C_6$-cycloalkyl, $C_1$-$C_6$-alkyl and benzyl;

or $R^3$ and $R^4$ together form a group independently selected from $C_1$-$C_2$-alkylene, —C(O)— and —C(S)—;

$R^5$ is a 10-membered heteroaryl group selected from quinoline, isoquinoline and quinazoline; wherein $R^5$ is substituted with from 1 to 5 $R^{5a}$ groups and/or a single $Z^1$—$Z^2$—$R^6$ group;

$Z^1$ is independently absent or is $CR^8R^9$;

$Z^2$ is independently absent or is selected from C(O)O, OC(O), O, S, S(O), $S(O)_2$, $C(O)NR^7$, $NR^7C(O)$, $S(O)_2NR^7$, $NR^7S(O)_2$, $S(O)NR^7$, NR'S(O), $CR^8R^9$, C(O), C(S), C=$NOR^{10}$, and $NR^7$;

$R^6$ is independently at each occurrence selected from $C_3$-$C_8$-alkyl and $C_0$-$C_3$-alkylene-$R^{6a}$; wherein $R^{6a}$ is independently at each occurrence selected from phenyl, 5- or 6-membered heteroaryl, 5-, 6-, 7- or 8-membered heterocycloalkyl and $C_5$-$C_8$-cycloalkyl; said heterocycloalkyl or cycloalkyl group being monocyclic or bicyclic; said heteroaryl or phenyl group being optionally substituted with from 1 to 5 $R^{15}$ groups or said heterocycloalkyl or cycloalkyl group being optionally substituted with from 1 to 4 $R^{16}$ groups;

$R^{16}$ is independently at each occurrence selected from: =O, =S, $C_1$-$C_6$-alkyl, $C_1$-$C_6$-haloalkyl, $C_3$-$C_6$-cycloalkyl; halogen, nitro, $OR^{11}$, $SR^{12}$, $OS(O)_2R^{12}$, $S(O)_2R^{12}$, $S(O)_2NR^{12}R^{12}$, $S(O)(NR^{12})R^{12}$, $S(O)R^{12}$, cyano, $C_2$-$C_6$-alkenyl, $C_2$-$C_6$-alkynyl, and $NR^{12}R^{13}$;

$R^7$ and $R^{12}$ are each independently at each occurrence selected from: H, $C_3$-$C_6$-cycloalkyl, $C_1$-$C_6$-alkyl and benzyl;

or where two $R^{12}$ groups are attached to the same nitrogen atom, said $R^{12}$ groups, together with said nitrogen atom form a 4-, 5-, 6- or 7-membered heterocycloalkyl ring;

$R^8$ is independently at each occurrence selected from: H, $C_3$-$C_6$-cycloalkyl, $C_1$-$C_6$-alkyl, phenyl and 5- or 6-membered heteroaryl;

$R^9$ is independently at each occurrence selected from: H, halo and $OR^{10}$;

or $R^8$ and $R^9$ together with the carbon atom to which they are attached may form a $C_3$-$C_6$-cycloalkyl ring or a 3-, 4-, 5- or 6-membered heterocycloalkyl ring;

$R^{10}$ is each independently at each occurrence selected from: H, $C_3$-$C_6$-cycloalkyl, $C_1$-$C_6$-alkyl and $C_1$-$C_3$-alkylene-$R^{10a}$; wherein $R^{10a}$ is independently at each occurrence selected from phenyl and 5- or 6-membered heteroaryl;

$R^{11}$ is independently at each occurrence selected from: H, $C_1$-$C_6$-alkyl, $C_3$-$C_6$-cycloalkyl, C(O)—$C_1$-$C_6$-alkyl and $C_1$-$C_6$-haloalkyl;

$R^{13}$ is independently at each occurrence selected from; H, $C_1$-$C_6$-alkyl, C(O)—$C_1$-$C_6$-alkyl and $S(O)_2$—$C_1$-$C_6$-alkyl;

or where an $R^{12}$ group and an $R^{13}$ group are attached to the same nitrogen atom, said $R^{12}$ and $R^{13}$ groups, together with said nitrogen atom form a 4-, 5-, 6- or 7-membered heterocycloalkyl ring;

$R^{14}$ is independently at each occurrence: $C_1$-$C_6$-alkyl, phenyl, benzyl and $C_3$-$C_6$-cycloalkyl;

n is independently an integer selected from 0, 1 and 2;

m is independently an integer selected from 0, 1, 2 and 3;

p is independently an integer selected from 0, 1, 2, 3 and 4;

q is independently an integer selected from 0 and 1; and wherein any aforementioned alkyl, alkylene, alkenyl, cycloalkyl, heterocycloalkyl (including where two $R^{12}$ groups or an $R^{12}$ group and an $R^{13}$ group together with a nitrogen to which they are attached form a heterocycloalkyl ring), alkynyl, C(O)-alkyl, $S(O)_2$-alkyl and benzyl is optionally substituted, where chemically possible, by 1 to 4 substituents which are each independently selected at each occurrence from the group consisting of: =O; $=NR^a$, $=NOR^a$, $C_1$-$C_4$-alkyl, halo, nitro, cyano, $C_1$-$C_4$-haloalkyl, $C_2$-$C_4$-alkenyl, $C_2$-$C_4$-alkynyl, $NR^aR^b$, $S(O)_2R^a$, $S(O)R^a$, $S(O)(NR^a)R^a$, $S(O)_2NR^aR^a$, $CO_2R^a$, $C(O)R^a$, $CONR^aR^a$, $OR^a$ and $SR^a$;

wherein $R^a$ is independently selected from H and $C_1$-$C_4$-alkyl; and $R^b$ is independently selected from H, $C_1$-$C_4$-alkyl, C(O)—$C_1$-$C_4$-alkyl and $S(O)_2$—$C_1$-$C_4$-alkyl.

In certain embodiments, the compound of formula I is a compound of formula II:

II

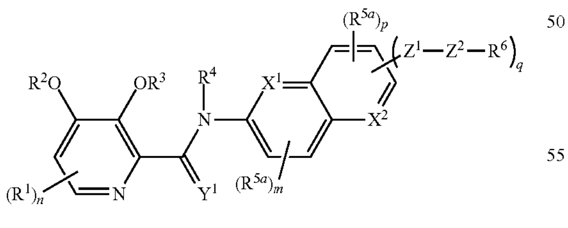

wherein $R^1$, $R^2$, $R^3$, $R^4$, $R^{5a}$, n, $Z^1$, $Z^2$ and $R^6$ are as described above for formula I; a single one of $X^1$ and $X^2$ is nitrogen and a single one of $X^1$ and $X^2$ is carbon; m is independently an integer selected from 0, 1, 2 and 3; p is independently an integer selected from 0, 1, 2, 3 and 4; and q is independently an integer selected from 0 and 1.

In certain embodiments, the compound of formula I is a compound of formula III:

III

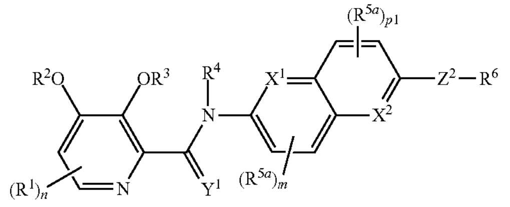

wherein $R^1$, $R^2$, $R^3$, $R^4$, $R^{5a}$, n, $Z^2$ and $R^6$ are as described above for formula I; a single one of $X^1$ and $X^2$ is nitrogen and a single one of $X^1$ and $X^2$ is carbon; m is independently an integer selected from 0, 1, 2 and 3; and p1 is independently an integer selected from 0, 1, 2 and 3.

In certain embodiments, the compound of formula I is a compound of formula IV:

IV

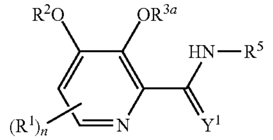

wherein $R^1$, $R^2$, $R^5$ and n are as described above for formula I; and $R^{3a}$ is independently selected from: H, $C_1$-$C_4$-alkyl, $C_3$-$C_6$-cycloalkyl, $C(O)R^{14}$, $C(O)OR^{14}$, $CH_2OC(O)R^{14}$ and $CH_2OC(O)OR^{14}$.

In certain embodiments, the compound of formula I is a compound of formula V:

V

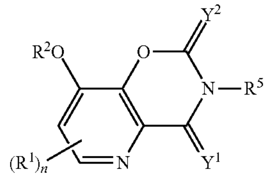

wherein $R^1$, $R^2$, $R^5$ and n are as described above for formula I; and $Y^2$ is independently selected from O and S.

In certain embodiments, the compound of formula I is a compound of formula VI:

VI

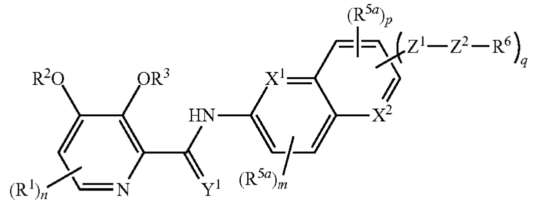

wherein $R^1$, $R^2$, $R^{5a}$, n, $Z^1$, $Z^2$ and $R^6$ are as described above for formula I; a single one of $X^1$ and $X^2$ is nitrogen and a single one of $X^1$ and $X^2$ is carbon; m is independently an integer selected from 0, 1, 2 and 3; p is independently an integer selected from 0, 1, 2, 3 and 4; q is independently an integer selected from 0 and 1; and $R^{3a}$ is independently selected from: H, $C_1$-$C_4$-alkyl, $C_3$-$C_6$-cycloalkyl, $C(O)R^{14}$, $C(O)OR^{14}$, $CH_2OC(O)R^{14}$ and $CH_2OC(O)OR^{14}$.

In certain embodiments, the compound of formula I is a compound of formula VI:

VI

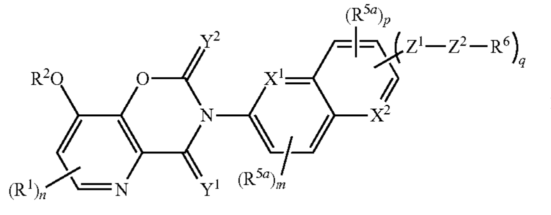

wherein $R^1$, $R^2$, $R^{5a}$, n, $Z^1$, $Z^2$ and $R^6$ are as described above for formula I; a single one of $X^1$ and $X^2$ is nitrogen and a single one of $X^1$ and $X^2$ is carbon; m is independently an integer selected from 0, 1, 2 and 3; p is independently an integer selected from 0, 1, 2, 3 and 4; q is independently an integer selected from 0 and 1; and $Y^2$ is independently selected from O and S.

In certain embodiments, the compound of formula I is a compound of formula VII:

VII

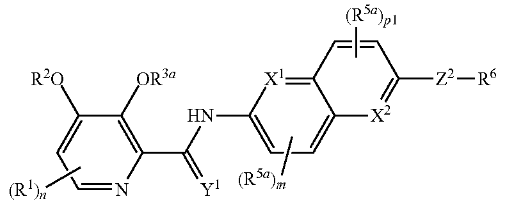

wherein $R^1$, $R^2$, $R^{5a}$, n, $Z^2$ and $R^6$ are as described above for formula I; a single one of $X^1$ and $X^2$ is nitrogen and a single one of $X^1$ and $X^2$ is carbon; m is independently an integer selected from 0, 1, 2 and 3; p1 is independently an integer selected from 0, 1, 2 and 3; and $R^{3a}$ is independently selected from: H, $C_1$-$C_4$-alkyl, $C_3$-$C_6$-cycloalkyl, $C(O)R^{14}$, $C(O)OR^{14}$, $CH_2OC(O)R^{14}$ and $CH_2OC(O)OR^{14}$.

In certain embodiments, the compound of formula I is a compound of formula VIII:

VIII

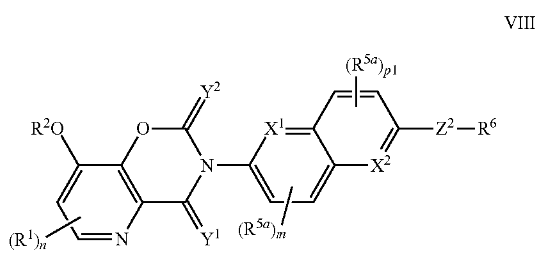

wherein $R^1$, $R^2$, $R^{5a}$, n, $Z^2$ and $R^6$ are as described above for formula I; a single one of $X^1$ and $X^2$ is nitrogen and a single one of $X^1$ and $X^2$ is carbon; m is independently an integer selected from 0, 1, 2 and 3; p1 is independently an integer selected from 0, 1, 2 and 3; and $Y^2$ is independently selected from O and S.

In certain embodiments, the compound of formula I is a compound of formula IX:

IX

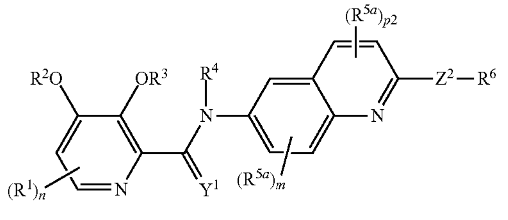

wherein $R^1$, $R^2$, $R^3$, $R^4$, $R^{5a}$, n, $Z^2$ and $R^6$ are as described above for formula I; m is independently an integer selected from 0, 1, 2 and 3; and p2 is independently an integer selected from 0, 1 and 2.

In certain embodiments, the compound of formula I is a compound of formula X:

X

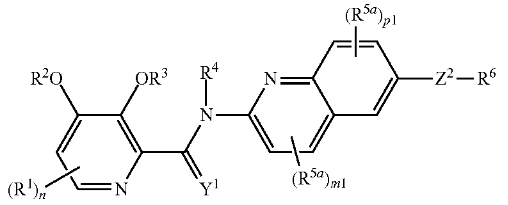

wherein $R^1$, $R^2$, $R^3$, $R^4$, $R^{5a}$, n, $Z^2$ and $R^6$ are as described above for formula I; m1 is independently an integer selected from 0, 1 and 2; and p1 is independently an integer selected from 0, 1, 2 and 3.

The following embodiments apply to compounds of any of formulae (I)-(X). These embodiments are independent and interchangeable. Any one embodiment may be combined with any other embodiment, where chemically allowed. In other words, any of the features described in the following embodiments may (where chemically allowable) be combined with the features described in one or more other embodiments. In particular, where a compound is exemplified or illustrated in this specification, any two or more of the embodiments listed below, expressed at any level of generality, which encompass that compound may be combined to provide a further embodiment which forms part of the present disclosure.

It may be that $R^1$ is independently at each occurrence selected from $C_1$-$C_4$-alkyl, halo and $OR^{11}$.

It may be that n is 1 or 2. Preferably, however, it may be that n is 0.

$R^2$ may be independently selected from H, $C_1$-$C_4$-alkyl and $C_3$-$C_6$-cycloalkyl. $R^2$ may be independently selected from $C_1$-$C_4$-alkyl and $C_3$-$C_6$-cycloalkyl. $R^2$ may be methyl or ethyl. $R^2$ may be methyl.

$R^3$ may be independently selected from H, $C_1$-$C_4$-alkyl, $C_3$-$C_6$-cycloalkyl, $C(O)R^{14}$, $C(O)OR^{14}$, $CH_2OC(O)R^{14}$ and $CH_2OC(O)OR^{14}$. $R^3$ may be independently selected from H, $C(O)R^{14}$, $C(O)OR^4$, $CH_2OC(O)R^4$ and $CH_2OC(O)OR^4$. $R^3$ may be independently selected from H, and $C(O)R^{14}$. $R^3$ may be H. $R^3$ may be $C(O)R^{14}$, e.g. C(O)Me.

$R^4$ may be selected from $C_3$-$C_6$-cycloalkyl, $C_1$-$C_6$-alkyl and benzyl. $R^4$ may be $C_1$-$C_4$-alkyl, e.g. methyl. $R^4$ may be H.

It may be that $R^3$ and $R^4$ together form a group independently selected from $C_1$-$C_2$-alkylene, —C(O)— and —C(S)—. It may be that $R^3$ and $R^4$ together form a group —C(=$Y^2$)—; wherein $Y^2$ is independently selected from O and S.

$Y^2$ may be S. $Y^2$ may be O.

It may be that $R^3$ and $R^4$ together form a $C_1$-$C_2$-alkylene. It may be that $R^3$ and $R^4$ together form a $C_1$ alkylene, e.g. $CH_2$ or $CMe_2$. It may be that $R^3$ and $R^4$ together form a $C_2$ alkylene, e.g.

$CH_2CMe_2$, $CMe_2CH_2$ or $CH_2CH_2$.

$Y^1$ may be S. $Y^1$ may be O.

$R^5$ may be a quinoline. $R^5$ may be an isoquinoline. $R^5$ may be a quinazoline.

It may be that $R^5$ is attached to the rest of the molecule via the ring of the heteroaromatic group that comprises the nitrogen atom(s). It may be that $R^5$ is attached to the rest of the molecule via the ring of the heteroaromatic group that does not comprise the nitrogen atom(s). It may be that $R^5$ is attached to the rest of the molecule via a carbon of the heteroaromatic group that is not next to a carbon that is part of both rings of the heteroaromatic group. Where present, it may be that $Z^1$—$Z^2$—$R^6$ is attached to $R^5$ via a carbon of the heteroaromatic group that is not next to a carbon atom that is part of both rings of the heteroaromatic group.

$R^5$ may have the structure:

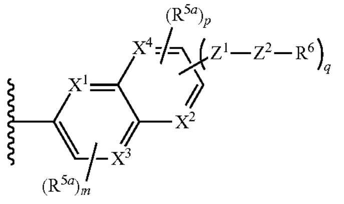

wherein a single one of $X^1$, $X^2$, $X^3$ and $X^4$ is nitrogen and the other three of $X^1$, $X^2$, $X^3$ and $X^4$ are carbon; m is independently an integer selected from 0, 1, 2 and 3; p is independently an integer selected from 0, 1, 2, 3 and 4; and q is independently an integer selected from 0 and 1.

$R^5$ may have the structure:

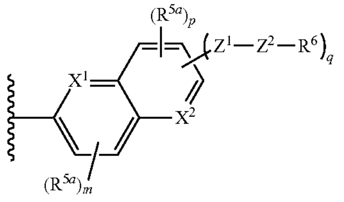

wherein a single one of $X^1$ and $X^2$ is nitrogen and a single one of $X^1$ and $X^2$ is carbon; m is independently an integer selected from 0, 1, 2 and 3; p is independently an integer selected from 0, 1, 2, 3 and 4; and q is independently an integer selected from 0 and 1.

$R^5$ may have the structure:

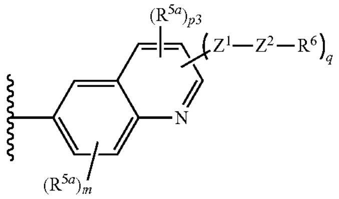

wherein m is independently an integer selected from 0, 1, 2 and 3; p3 is independently an integer selected from 0, 1, 2 and 3; and q is independently an integer selected from 0 and 1.

$R^5$ may have the structure:

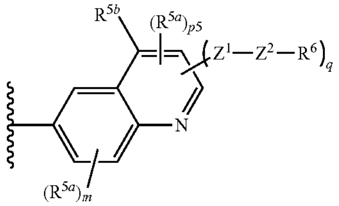

wherein m is independently an integer selected from 0, 1, 2 and 3; p5 is independently an integer selected from 0, 1 and 2; q is independently an integer selected from 0 and 1; and $R^{5b}$ is selected from $OR^{11}$ and $C_1$-$C_6$-alkyl group. It may be that $R^{5b}$ is $C_1$-$C_6$-alkyl.

$R^5$ may have the structure:

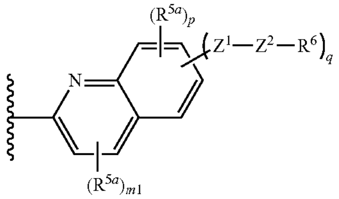

wherein m1 is independently an integer selected from 0, 1 and 2; p is independently an integer selected from 0, 1, 2, 3 and 4; and q is independently an integer selected from 0 and 1.

$R^5$ may have the structure:

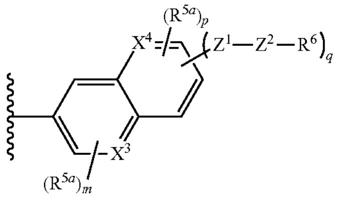

wherein a single one of $X^3$ and $X^4$ is nitrogen and a single one of $X^3$ and $X^4$ is carbon; m is independently an integer selected from 0, 1, 2 and 3; p is independently an integer selected from 0, 1, 2, 3 and 4; and q is independently an integer selected from 0 and 1.

$R^5$ may have the structure:

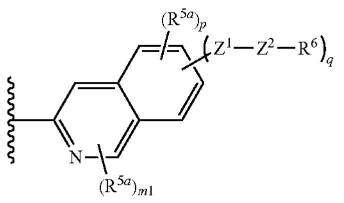

wherein m1 is independently an integer selected from 0, 1 and 2; p is independently an integer selected from 0, 1, 2, 3 and 4; and q is independently an integer selected from 0 and 1.

$R^5$ may have the structure:

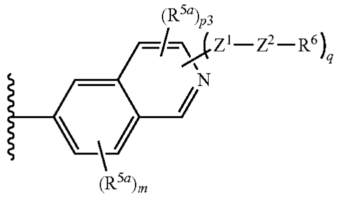

wherein m is independently an integer selected from 0, 1, 2 and 3; p3 is independently an integer selected from 0, 1, 2 and 3; and q is independently an integer selected from 0 and 1.

$R^5$ may have the structure:

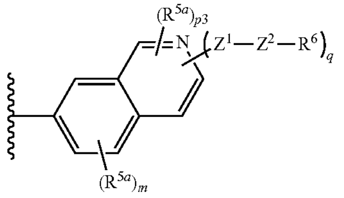

wherein m is independently an integer selected from 0, 1, 2 and 3; p3 is independently an integer selected from 0, 1, 2 and 3; and q is independently an integer selected from 0 and 1.

$R^5$ may have the structure:

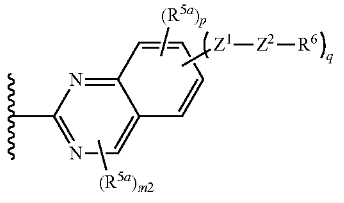

wherein m2 is independently an integer selected from 0 and 1; p is independently an integer selected from 0, 1, 2, 3 and 4; and q is independently an integer selected from 0 and 1.

$R^5$ may have the structure:

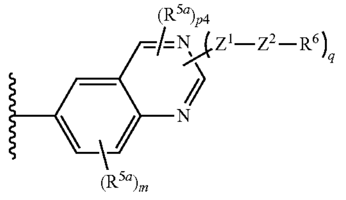

wherein m is independently an integer selected from 0, 1, 2 and 3; p4 is independently an integer selected from 0, 1 and 2; and q is independently an integer selected from 0 and 1.

$R^5$ may have the structure:

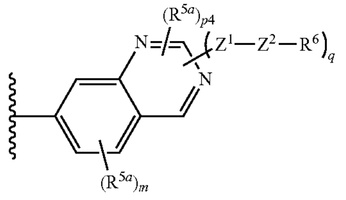

wherein m is independently an integer selected from 0, 1, 2 and 3; p4 is independently an integer selected from 0, 1 and 2; and q is independently an integer selected from 0 and 1.

q may be 0. Preferably, however, q is 1.

Where q is 1, the $Z^1$—$Z^2$—$R^6$ group is preferably situated para to the point of connection of $R^5$ to the rest of the molecule.

$R^5$ may have the structure:

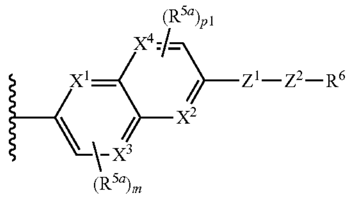

wherein a single one of $X^1$, $X^2$, $X^3$ and $X^4$ is nitrogen and the other three of $X^1$, $X^2$, $X^3$ and $X^4$ are carbon; m is independently an integer selected from 0, 1, 2 and 3; and p1 is independently an integer selected from 0, 1, 2 and 3.

$R^5$ may have the structure:

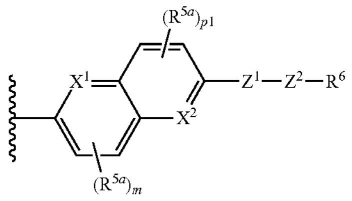

wherein a single one of $X^1$ and $X^2$ is nitrogen and a single one of $X^1$ and $X^2$ is carbon; m is independently an integer selected from 0, 1, 2 and 3; and p1 is independently an integer selected from 0, 1, 2 and 3.

$R^5$ may have the structure:

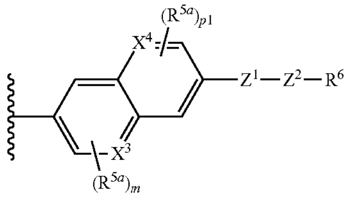

wherein a single one of $X^3$ and $X^4$ is nitrogen and a single one of $X^3$ and $X^4$ is carbon; m is independently an integer selected from 0, 1, 2 and 3; and p1 is independently an integer selected from 0, 1, 2 and 3. $X^3$ may be N. Alternatively, $X^4$ may be N.

$R^5$ may have the structure:

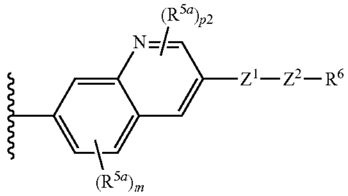

wherein m is independently an integer selected from 0, 1, 2 and 3; and p2 is independently an integer selected from 0, 1 and 2.

$R^5$ may have the structure:

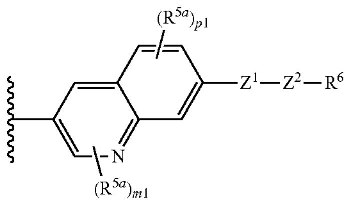

wherein m1 is independently an integer selected from 0, 1 and 2; and p1 is independently an integer selected from 0, 1, 2 and 3.

m may be 0.

m1 may be 0.

m2 may be 0.

p may be 0. Where q is 0, however, p is preferably at least 1.

p1 may be 0.

p2 may be 0.

p3 may be 0. Where q is 0, however, p3 is preferably at least 1.

p4 may be 0. Where q is 0, however, p4 is preferably at least 1.

p5 may be 0. Where q is 0, however, p5 is preferably at least 1.

Where present, $R^{5a}$ may be independently at each occurrence selected from: cyano, nitro, $C_1$-$C_4$-alkyl, halo and $OR^{11}$.

$Z^1$ may be $CR^3R^9$. Preferably, however, $Z^1$ is absent. $Z^1$—$Z^2$—$R^6$ may be $Z^2$—$R^6$.

$Z^2$ may be absent or selected from C(O)O, OC(O), O, S, S(O), $S(O)_2$, $CR^3R^9$ and $NR^7$. $Z^2$ may be absent or selected from C(O)O, OC(O), O, S, $CR^3R^9$, and $NR^7$. $Z^2$ may be selected from $CR^3R^9$, S, $NR^7$ and O. $Z^2$ may be absent or selected from $NR^7$, S, and O. $Z^2$ may be selected from $NR^7$, S, and O. $Z^2$ may be selected from O and S. $Z^2$ may be O. $Z^2$ may be S. $Z^2$ may be $NR^7$. $Z^2$ may be $CR^8R^9$.

$R^7$ may be H. Preferably, however $R^7$ is $C_1$-$C_4$-alkyl, e.g. methyl.

$Z^2$ may be absent. $Z^1$—$Z^2$—$R^6$ may be $R^6$.

$R^6$ may be $CH_2R^{6a}$. Alternatively, $R^6$ may be $R^{6a}$.

$Z^1$—$Z^2$—$R^6$ may be $Z^1$—$Z^2$—$R^{6a}$. $Z^1$—$Z^2$—$R^6$ may be $Z^2$—$R^{6a}$. $Z^1$—$Z^2$—$R^6$ may be $R^{6a}$.

$R^{6a}$ may be optionally substituted phenyl, e.g. unsubstituted phenyl. $R^6$ maybe optionally substituted phenyl, e.g. unsubstituted phenyl.

$R^{6a}$ may have the structure:

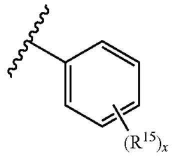

wherein x is an integer selected from 0, 1, 2, 3, 4 and 5.

x may be at least 1. x may be 1, 2 or 3. x may be 1 or 2. x may be 1. x may be O.

$R^{15}$ may in a single occurrence be situated para to $Z^2$.

$R^{6a}$ may have the structure:

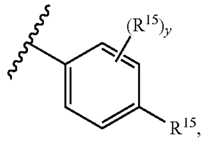

wherein y is an integer selected from 0, 1, 2, 3 and 4.

y may be at least 1. y may be 1 or 2. y may be 1. y may be O.

$R^{6a}$ may have the structure:

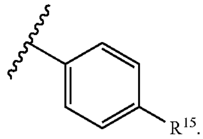

$R^{15}$ may be independently at each occurrence selected from: cyano, nitro, $C_1$-$C_4$-alkyl, $C_1$-$C_4$-haloalkyl, halo, S—$R^{12}$ and O—$R^{11}$. $R^{15}$ may be independently at each occurrence selected from: $C_1$-$C_4$-alkyl, $C_1$-$C_4$-haloalkyl and halo.

$R^{6a}$ may be a 6-membered heteroaryl, e.g. a pyridine.

$R^{6a}$ may have a structure selected from:

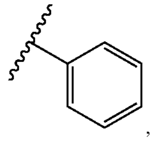
,
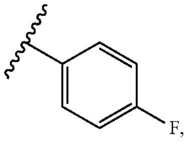
,

-continued
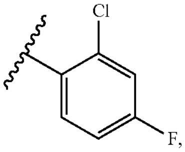,
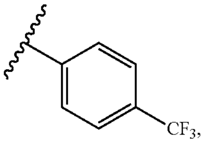,
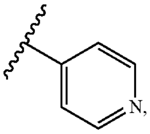,
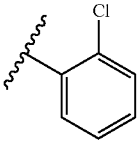,
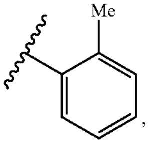,
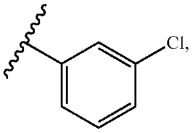,
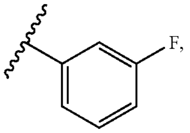,
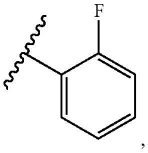,
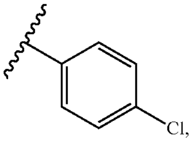,
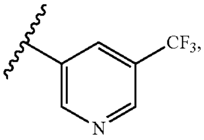,
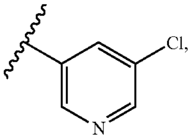,
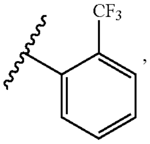,
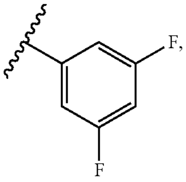,
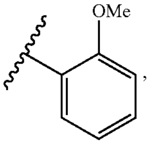,
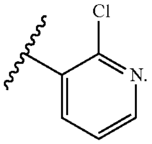.
$R^6$ may be $C_3$-$C_3$-alkyl, e.g. $C_3$-$C_6$-alkyl. This is particularly preferred where $Z^2$ is selected from O, S and $NR^7$.
The compound of formula (I) may be selected from:
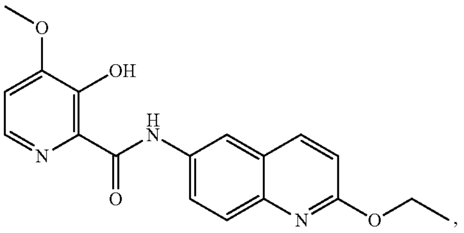,
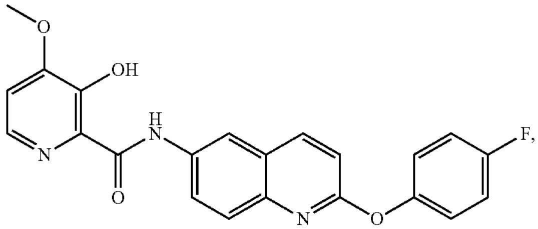,
-continued
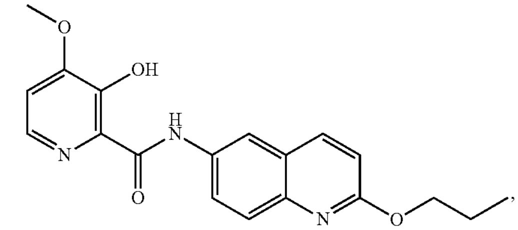,
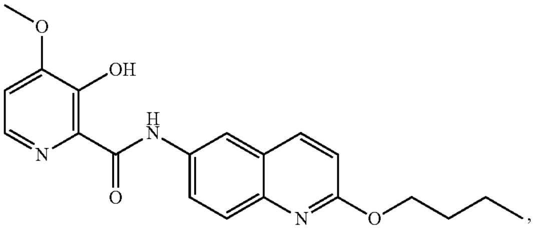,
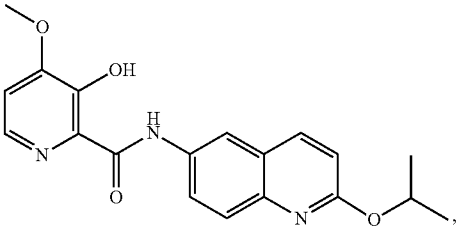,
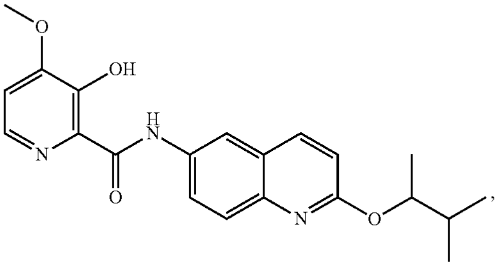,
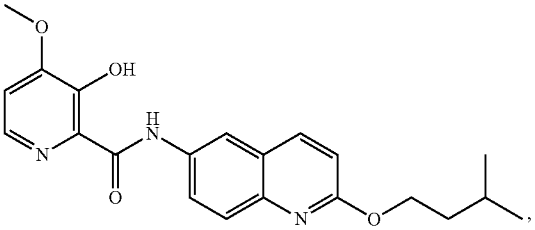,
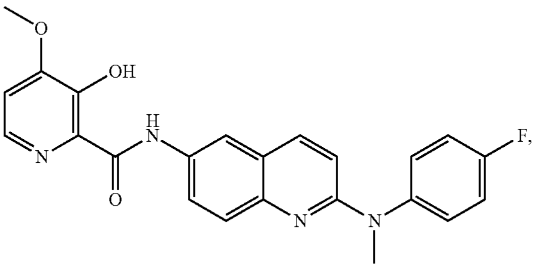,
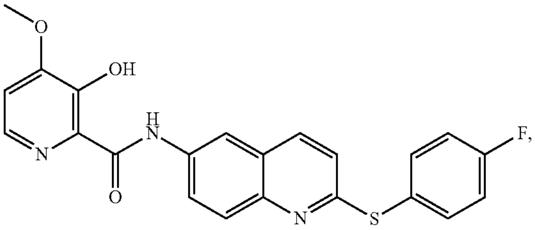, -continued
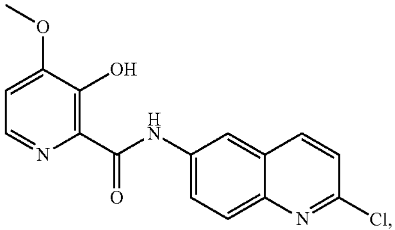,
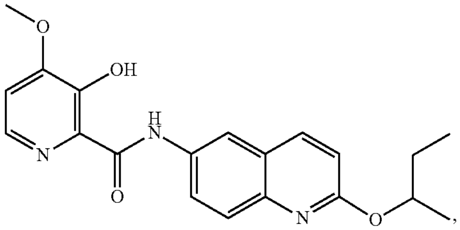,
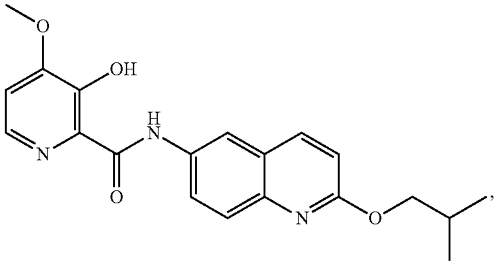,
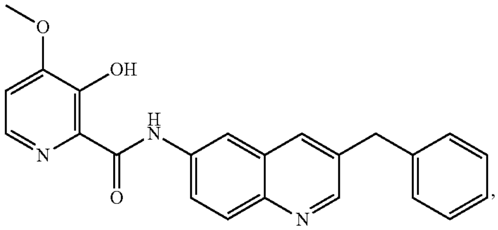,
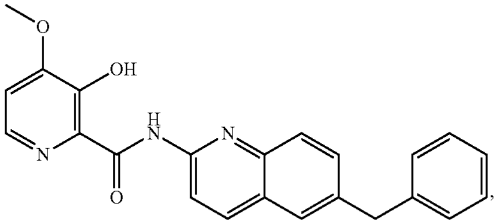,
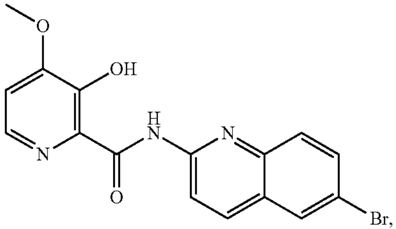,
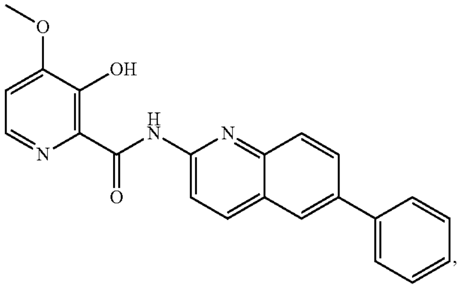,
-continued
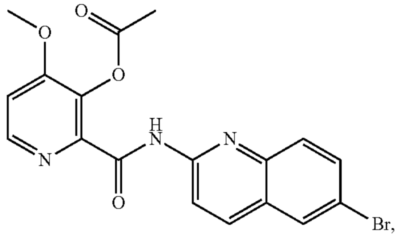,
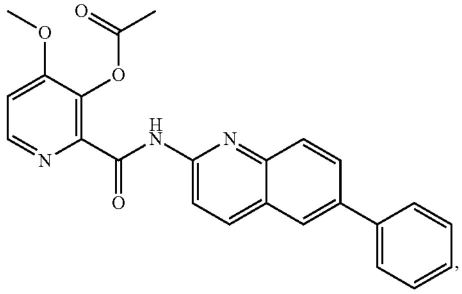,
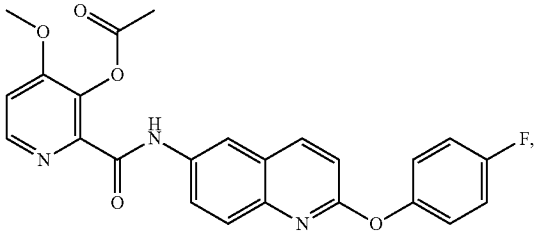,
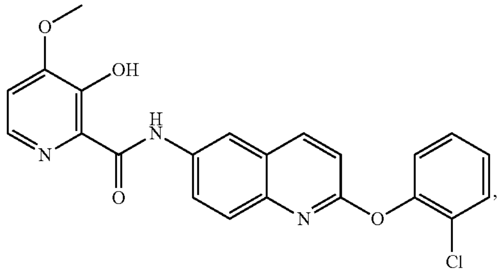,
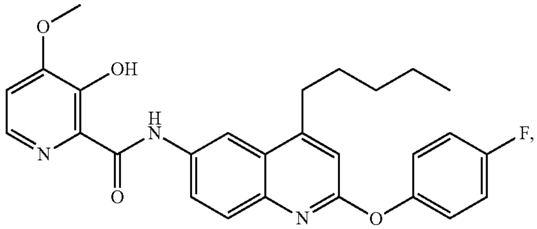,
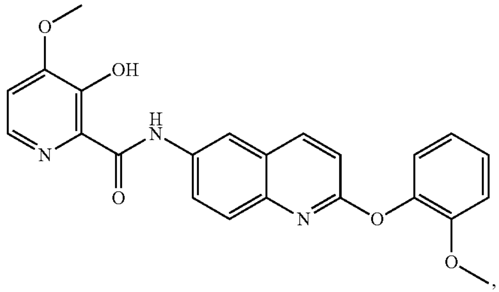, -continued
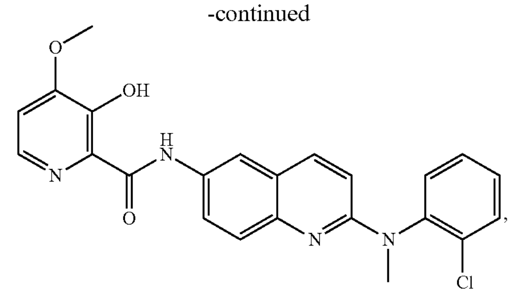
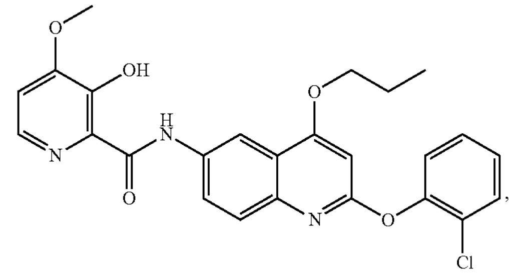
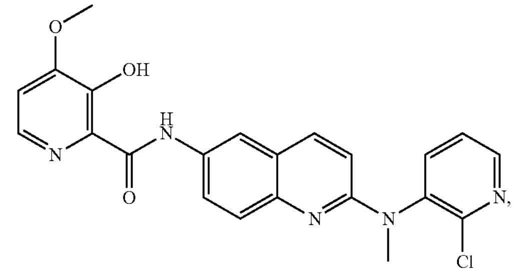
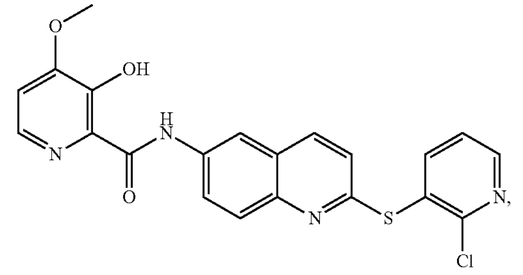
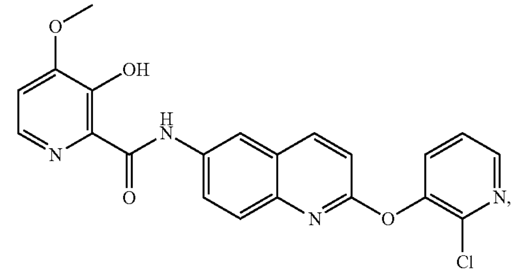
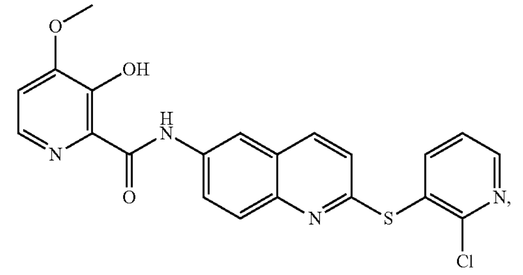
-continued
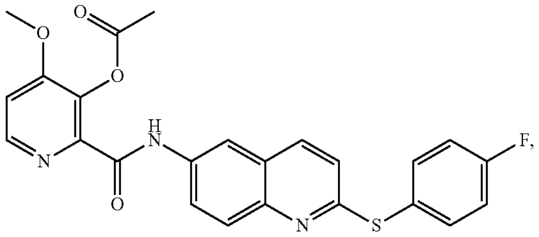
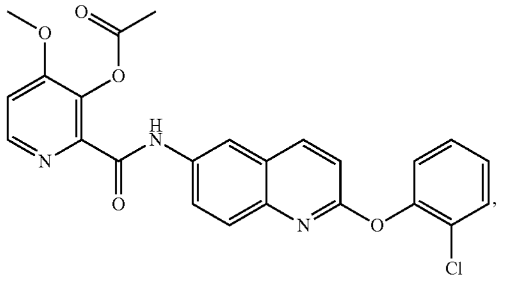
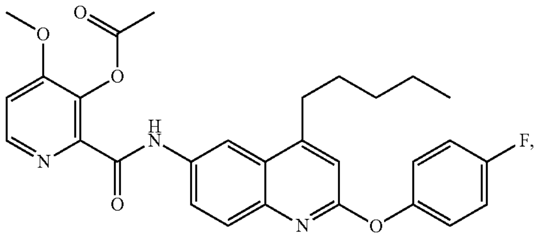
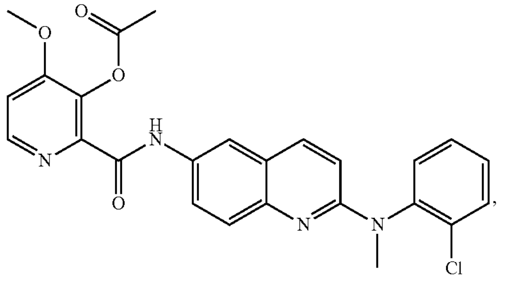
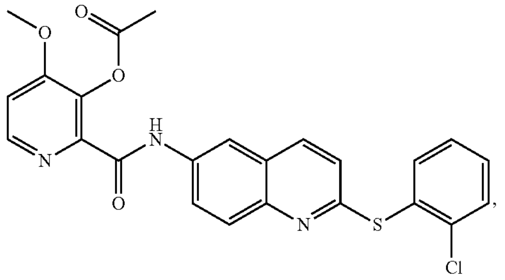
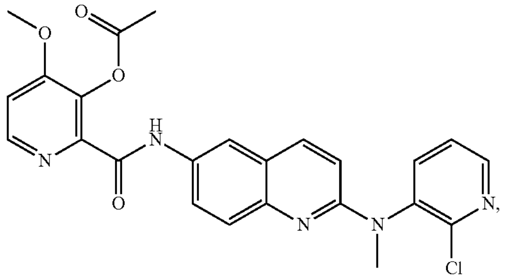

-continued
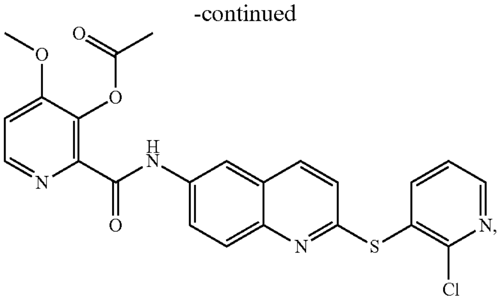
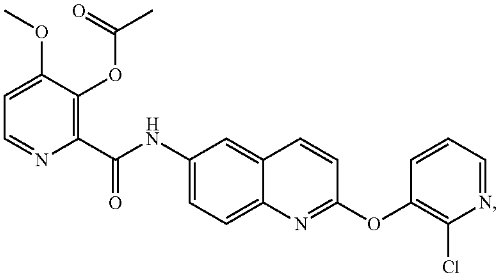
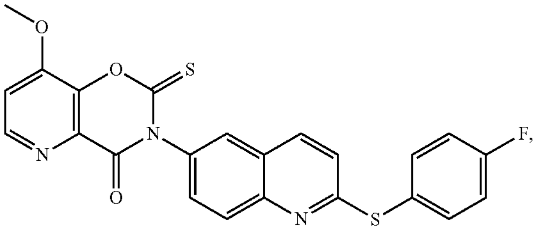
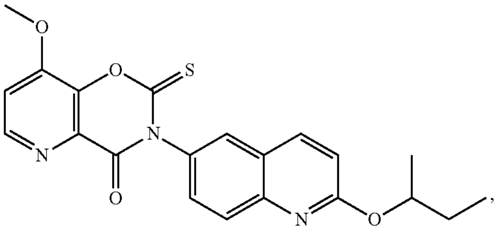
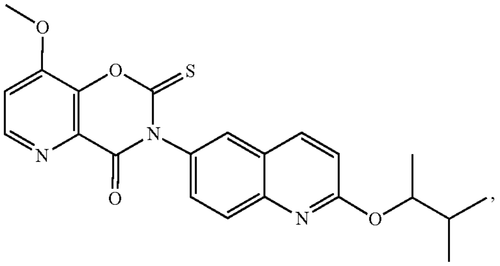
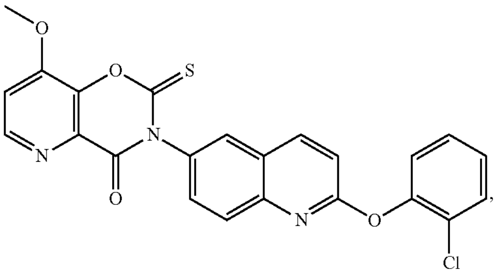
-continued
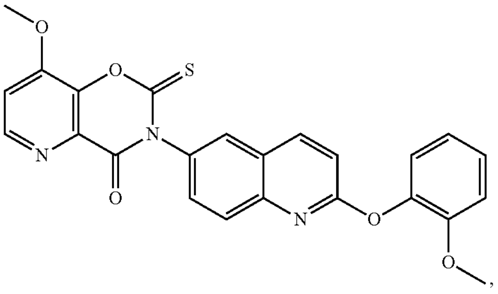
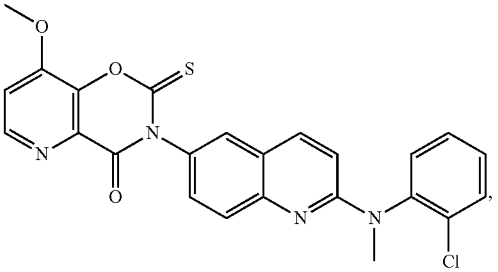
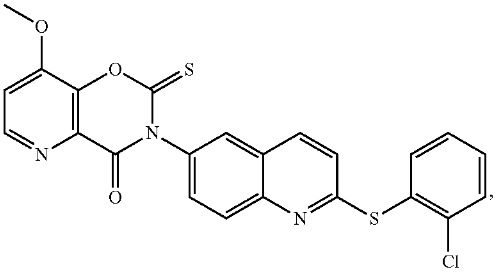
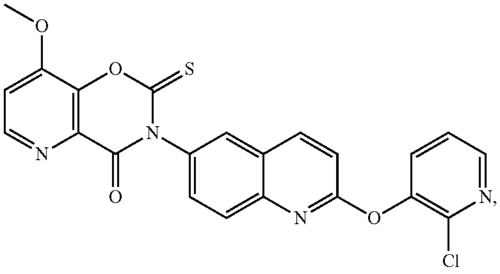
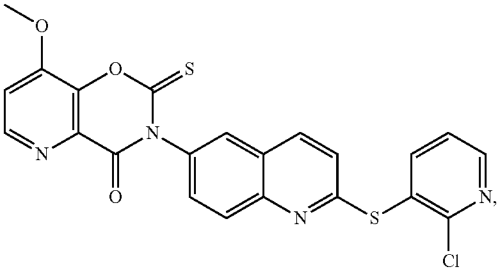
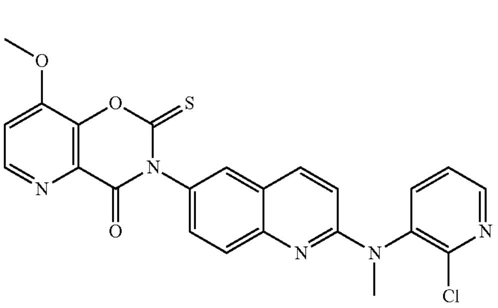
and -continued

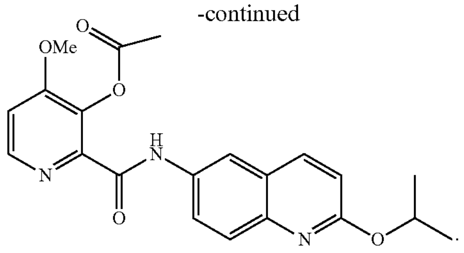

DETAILED DESCRIPTION

The term $C_m$-$C_n$ refers to a group with m to n carbon atoms.

The term "alkyl" refers to a linear or branched saturated monovalent hydrocarbon chain. For example, $C_1$-$C_6$-alkyl may refer to methyl, ethyl, n-propyl, iso-propyl, n-butyl, sec-butyl, tert-butyl, n-pentyl and n-hexyl. The alkyl groups may be unsubstituted or substituted by one or more substituents. Specific substituents for each alkyl group independently may be fluorine, $OR^a$ or $NHR^a$.

The term "alkylene" refers to a linear saturated divalent hydrocarbon chain. The alkylene groups may be unsubstituted or substituted by one or more substituents. Specific substituents for each alkylene group independently may be $C_1$-$C_4$-alkyl, fluorine, $OR^a$ or $NHR^a$.

The term "haloalkyl" refers to a hydrocarbon group substituted with at least one halogen atom independently chosen at each occurrence from: fluorine, chlorine, bromine and iodine. The halogen atom may be present at any position on the hydrocarbon chain. For example, $C_1$-$C_6$-haloalkyl may refer to chloromethyl, fluoromethyl, trifluoromethyl, chloroethyl e.g. 1-chloroethyl and 2-chloroethyl, trichloroethyl e.g. 1,2,2-trichloroethyl, 2,2,2-trichloroethyl, fluoroethyl e.g. 1-fluoroethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl. A haloalkyl group may be a fluoroalkyl group, i.e. a hydrocarbon chain substituted with at least one fluorine atom. Thus, a haloalkyl group may have any amount of halogen substituents. The group may contain a single halogen substituent, it may have two or three halogen substituents, or it may be saturated with halogen substituents.

The term "alkenyl" refers to a branched or linear hydrocarbon group containing at least one double bond. The double bond(s) may be present as the E or Z isomer. The double bond may be at any possible position of the hydrocarbon chain; for example, "$C_2$-$C_6$-alkenyl" may refer to ethenyl, propenyl, butenyl, butadienyl, pentenyl, pentadienyl, hexenyl and hexadienyl. The alkenyl groups may be unsubstituted or substituted by one or more substituents. Specific substituents for any saturated carbon atom in each alkenyl group independently may be fluorine, $OR^a$ or $NHR^a$.

The term "alkynyl" refers to a branched or linear hydrocarbon chain containing at least one triple bond. The triple bond may be at any possible position of the hydrocarbon chain. For example, "$C_2$-$C_6$-alkynyl" may refer to ethynyl, propynyl, butynyl, pentynyl and hexynyl. The alkynyl groups may be unsubstituted or substituted by one or more substituents. Specific substituents for any saturated carbon atom in each alkynyl group independently may be fluorine, $OR^a$ or $NHR^a$.

The term "cycloalkyl" refers to a saturated hydrocarbon ring system containing, for example, 3, 4, 5 or 6 carbon atoms. For example, "$C_3$-$C_6$-cycloalkyl" may refer to cyclopropyl, cyclobutyl, cyclopentyl, cyclohexyl. The cycloalkyl groups may be unsubstituted or substituted by one or more substituents. Specific substituents for each cycloalkyl group independently may be fluorine, $OR^a$ or $NHR^a$.

The term heterocycloalkyl may refer to a monocyclic or bicyclic saturated or partially saturated group having the indicated number of atoms in the ring system and comprising 1 or 2 heteroatoms independently selected from O, S and N in the ring system (in other words 1 or 2 of the atoms forming the ring system are selected from O, S and N). By partially saturated it is meant that the ring may comprise one or two double bonds. This applies particularly to monocyclic rings with from 5 to 6 members. The double bond will typically be between two carbon atoms but may be between a carbon atom and a nitrogen atom. Examples of heterocycloalkyl groups include; piperidine, piperazine, morpholine, thiomorpholine, pyrrolidine, tetrahydrofuran, tetrahydrothiophene, dihydrofuran, tetrahydropyran, dihydropyran, dioxane, azepine. A heterocycloalkyl group may be unsubstituted or substituted by one or more substituents. Specific substituents for any saturated carbon atom in each heterocycloalkyl group may independently be fluorine, $OR^a$ or $NHR^a$.

Aryl groups may be any aromatic carbocyclic ring system (i.e. a ring system containing $2(2n+1)\pi$ electrons). Aryl groups may have from 6 to 12 carbon atoms in the ring system. Aryl groups will typically be phenyl groups. Aryl groups may be naphthyl groups or biphenyl groups.

In any of the above aspects and embodiments, heteroaryl groups may be any aromatic (i.e. a ring system containing $2(2n+1)\pi$ electrons) 5-10 membered ring system comprising from 1 to 4 heteroatoms independently selected from O, S and N (in other words from 1 to 4 of the atoms forming the ring system are selected from O, S and N). Thus, any heteroaryl groups may be independently selected from: 5 membered heteroaryl groups in which the heteroaromatic ring is substituted with 14 heteroatoms independently selected from O, S and N; and 6-membered heteroaryl groups in which the heteroaromatic ring is substituted with 1-3 (e.g. 1-2) nitrogen atoms; 9-membered bicyclic heteroaryl groups in which the heteroaromatic system is substituted with 1-4 heteroatoms independently selected from O, S and N; 10-membered bicyclic heteroaryl groups in which the heteroaromatic system is substituted with 1-4 nitrogen atoms. Specifically, heteroaryl groups may be independently selected from: pyrrole, furan, thiophene, pyrazole, imidazole, oxazole, isoxazole, triazole, oxadiazole, thiadiazole, tetrazole, pyridine, pyridazine, pyrimidine, pyrazine, triazine, indole, isoindole, benzofuran, isobenzofuran, benzothiophene, indazole, benzimidazole, benzoxazole, benzothiazole, benzisoxazole, purine, quinoline, isoquinoline, cinnoline, quinazoline, quinoxaline, pteridine, phthalazine, naphthyridine.

It may be that, in any group which is an aryl or heteroaryl group, that aryl or heteroaryl group is unsubstituted or is optionally substituted, where chemically possible, by 1 to 5 substituents which are each independently selected at each occurrence from: halo, nitro, cyano, $NR^aR^a$, $NR^aS(O)_2R^a$, $NR^aC(O)R^a$, $NR^aCONR^aR^a$, $NR^aCO_2R^a$, $OR^a$, $SR^a$, $S(O)R^a$, $S(O)_2OR^a$, $S(O)_2R^a$, $S(O)_2NR^aR^a$, $CO_2R^a$ $C(O)R^a$, $CONR^aR^a$, $CR^bR^bNR^aR^a$, $CR^bR^bOR^a$, $C_1$-$C_4$-alkyl, $C_2$-$C_4$-alkenyl, $C_2$-$C_4$-alkynyl and $C_1$-$C_4$-haloalkyl; wherein $R^a$ and $R^b$ are as described above for formula I.

Compounds of the invention containing one or more asymmetric carbon atoms can exist as two or more stereoisomers. Where a compound of the invention contains a double bond such as a C═C or C═N group, geometric cis/trans (or Z/E) isomers are possible. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of the invention, including compounds exhibiting more than one type of isomerism, and mixtures of one or more thereof.

The compounds of the invention may be obtained, stored and/or used in the form of an agronomically acceptable salt. Suitable salts include, but are not limited to, salts of acceptable inorganic acids such as hydrochloric, sulfuric, phosphoric, nitric, carbonic, boric, sulfamic, and hydrobromic acids, or salts of agronomically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulfonic, toluenesulfonic, benzenesulfonic, salicylic, sulfanilic, aspartic, glutamic, edetic, stearic, palmitic, oleic, lauric, pantothenic, tannic, ascorbic and valeric acids. Suitable salts also include salts of inorganic and organic bases, e.g. counterions such as Na, Ca, K, Li, Mg, ammonium, trimethylsulfonium. The compounds may also be obtained, stored and/or used in the form of an N-oxide. Also included are acid addition salts or base salts wherein the counter ion is optically active; for example, d-lactate or l-lysine, or racemic; for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers when necessary include chiral synthesis from a suitable optically pure precursor or resolution of the racemate (or the racemate of a salt or derivative) using, for example, chiral high pressure liquid chromatography (HPLC). Thus, chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and for specific examples, 0 to 5% by volume of an alkylamine e.g. 0.1% diethylamine. Concentration of the eluate affords the enriched mixture.

Alternatively, the racemate (or a racemic precursor) may be reacted with a suitable optically active compound, for example, an alcohol, or, in the case where the compound of the invention contains an acidic or basic moiety, a base or acid such as 1-phenylethylamine or tartaric acid. The resulting diastereomeric mixture may be separated by chromatography and/or fractional crystallisation and one or both of the diastereoisomers converted to the corresponding pure enantiomer(s) by means well known to a skilled person.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see for example, "Stereochemistry of Organic Compounds" by E. L. Eliel and S. H. Wilen (Wiley, 1994).

The activity of the compounds of the present invention can be assessed by a variety of in silico, in vitro and in vivo assays. In silico analysis of a variety of compounds has been demonstrated to be predictive of ultimate in vitro and even in vivo activity.

The present invention also includes all environmentally acceptable isotopically-labelled compounds of formulae I to X and their syntheses, wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Isotopically-labelled compounds can generally be prepared by conventional techniques known to those skilled in the art or by processes analogous to those described using an appropriate isotopically-labelled reagent in place of the non-labelled reagent previously employed.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

If appropriate, the compounds of the invention can, at certain concentrations or application rates, be used as fungicides.

According to another aspect of the present invention, there is provided a method for controlling fungal diseases, the method comprising the application of an agronomically effective and substantially non-phytotoxic (to the crop plant) quantity of a compound of the invention to the seeds of the plants, to the plants themselves or to the area where it is intended that the plants will grow.

The pesticide may be applied as a seed treatment, foliar application, stem application, drench or drip application (chemigation) to the seed, the plant or to the fruit of the plant or to soil or to inert substrate (e.g. inorganic substrates like sand, rockwool, glasswool; expanded minerals like perlite, vermiculite, zeolite or expanded clay), Pumbe, Pyroclastic materials or stuff, synthetic organic substrates (e.g. polyurethane) organic substrates (e.g. peat, composts, tree waste products like coir, wood fibre or chips, tree bark) or to a liquid substrate (e.g. floating hydroponic systems, Nutrient Film Technique, Aeroponics).

In a further aspect, the present invention also relates to a fungicidal composition comprising an effective and non-phytotoxic amount of an active compound of the invention. The composition may further comprise one or more additional fungicides.

The term "effective and non-phytotoxic amount" means an amount of pesticide according to the invention which is sufficient to control or destroy any of the targeted pests present or liable to appear in the crops and which does not have any significant detrimental effect on the crops or indeed has a positive effect on plant vigour and yield in the absence of target organism.

The amount will vary depending on the pest to be controlled, the type of crop, the climatic conditions and the compounds included in the pesticidal composition. This amount can be determined by systematic field trials, which are within the capabilities of a person skilled in the art.

Depending on their particular physical and/or chemical properties, the active compounds of the invention can be formulated as solutions, emulsions, suspensions, powders, foams, pastes, granules, aerosols, microencapsulations in polymeric substances and in coating materials for seed, and also as ULV cold and warm fogging formulations.

The active compounds can be used neat, or in the form of a formulation, e.g. ready-to-use solutions, emulsions, water- or oil-based suspensions, powders, wettable powders, pastes, soluble powders, dusts, soluble granules, granules for broadcasting, suspoemulsion concentrates, natural substances impregnated with active compound, synthetic substances impregnated with active compound, fertilizers and also microencapsulations in polymeric substances. Application may be carried out, for example, by watering, spraying, atomising, broadcasting, dusting, foaming, spreading, etc. It is also possible to apply the active compounds by the ultra-low volume method or to inject the preparation of active compound or the active compound itself into the soil. It is also possible to treat the seed of the plants.

Formulations containing the compounds of the invention are produced in a known manner, for example by mixing the compounds with extenders (e.g. liquid solvents and/or solid carriers), optionally with the use of surfactants (e.g. emulsifiers and/or dispersants and/or foam-formers). The formulations are prepared either in factories/production plants or alternatively before or during the application.

Auxiliaries are substances which are suitable for imparting to the composition itself and/or to preparations derived therefrom (for example; spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender used is water, it is also possible to use, for example, organic solvents as auxiliary solvents. Essentially, suitable liquid solvents are: aromatics such as xylene, toluene or alkylnaphthalenes; chlorinated aromatics and chlorinated aliphatic hydrocarbons such as chlorobenzenes, chloroethylenes or methylene chloride; aliphatic hydrocarbons such as cyclohexane or paraffins, for example petroleum fractions; alcohols such as butanol or glycol and also their ethers and esters; ketones such as acetone, methyl ethyl ketone, methyl isobutyl ketone or cyclohexanone; strongly polar solvents such as dimethylformamide and dimethyl sulfoxide.

Suitable solid carriers are: for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and also protein hydrolysates; suitable dispersants are nonionic and/or ionic substances, for example from the classes of the alcohol-POE and/or -POP ethers, acid and/or POP-POE esters, alkylaryl and/or POP-POE ethers, fat- and/or POP-POE adducts, POE- and/or POP-polyol derivatives, POE- and/or POP-sorbitan- or -sugar adducts, alkyl or aryl sulfates, alkyl- or arylsulfonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulfonic acid derivatives, unmodified and modified celluloses, aromatic and/or aliphatic sulfonic acids and their adducts with formaldehyde.

Tackifiers such as carboxymethylcellulose and natural and synthetic polymers in the form of powders, granules or lattices, such as gum arabic, polyvinyl alcohol and polyvinyl acetate, as well as natural phospholipids such as cephalins and lecithins, and synthetic phospholipids, can be used in the formulations.

Further additives may be mineral and vegetable oils. It is also possible to add colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc. Other possible additives are perfumes, mineral or vegetable, optionally modified oils and waxes.

The formulations may also comprise stabilizers, e.g. low-temperature stabilizers, preservatives, antioxidants, light stabilizers or other agents which improve chemical and/or physical stability.

The formulations generally comprise between 0.01 and 98% by weight of active compound, preferably between 0.1 and 95% and particularly preferably between 0.5 and 90%.

The active compounds of the invention can also be used as a mixture with other known fungicides, for example, to improve the activity spectrum or to reduce or slow the development of resistance. A mixture with other known active compounds such as nematicides, herbicides, insecticides, acaricides, or bactericides, or with fertilizers and growth regulators, safeners or semiochemicals is also possible.

Exemplary application rates of the active compounds according to the invention are: when treating leaves: from 0.1 to 10 000 g/ha, preferably from 10 to 1000 g/ha, particularly preferably from 50 to 300 g/ha (when the application is carried out by watering or dripping, it is even possible to reduce the application rate, especially when inert substrates such as rock wool or perlite are used); when treating seed: from 2 to 200 g per 100 kg of seed, preferably from 2.5 to 150 g per 100 kg of seed, and particularly preferably from 2.5 to 25 g per 100 kg of seed, very particularly preferably from 2.5 to 12.5 g per 100 kg of seed; when treating the soil: from 0.1 to 10000 g/ha, preferably from 1 to 5000 g/ha.

The compositions according to the invention are suitable for protecting any plant variety which is employed in agriculture, in the greenhouse, in forests or in horticulture and, in particular, cereals (e.g. wheat, barley, rye, millet and oats), maize, cotton, soya beans, rice, potatoes, sunflowers, beans, coffee, beet (for example sugar beet and fodder beet), peanuts, vegetables (e.g. tomatoes, cucumbers, onions and lettuce), lawns, fruit and nut trees (e.g. apples, pears, peaches, nectarines, apricots, hazelnut, pecan, macadamia, pistachio), soft fruit (e.g. strawberries, raspberries, blackcurrants, redcurrants), grapevines, bananas, cocoa and ornamental plants.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material and for controlling pests, in particular fungal diseases, which are encountered in agriculture, in horticulture, in animal husbandry, in forests, in gardens and leisure facilities, in the protection of stored products and of materials, and in the hygiene sector. They may be preferably employed as crop protection agents.

Use as Fungicides

The compounds of the invention have activity as fungicides.

The following are illustrative examples of agricultural pests that may be controlled by fungicidal compounds:

Powdery mildew diseases such as: Blumeria diseases, caused for example by *Blumeria graminis*; Podosphaera diseases, caused for example by Podosphaera leucotheca; Sphaerotheca diseases, caused for example by *Sphaerotheca fuliginea*; Uncinula diseases, caused for example by *Uncinula necator*; Rust diseases such as: Gymnosporangium diseases, caused for example by *Gymnosporangium sabinae*; Hemileia diseases, caused for example by *Hemileia vastatix;*

Phakopsora diseases, caused for example by *Phakopsora pachyrhizi* or *Phakopsora meibomiae*; Puccinia diseases, caused for example by *Puccinia recondita*; Uromyces diseases, caused for example by *Uromyces appendiculatus*; Oomycete diseases such as:

Albugo diseases caused for example by *Albugo candida;*

Bremia diseases, caused for example by *Bremia lactucae*; Peronospora diseases, caused for example by *Peronospora pisi* or *P. brassicae*; Phytophthora diseases, caused for example by *Phytophthora infestans*; Plasmopara diseases, caused for example by *Plasmopara viticola*; Pseudoperonospora diseases, caused for example by *Pseudoperonospora humuli* or *Pseudoperonospora cubensis*; Pythium diseases, caused for example by *Pythium ultimum*; Leafspot, leaf blotch and leaf blight diseases such as: Alternaria diseases, caused for example by *Alternaria solani*; Cercospora diseases, caused for example by *Cercospora beticola*; Cladiosporum diseases, caused for example by *Cladiosporium cucumerinum*; Cochliobolus diseases, caused for example by *Cochliobolus sativus*; Colletotrichum diseases, caused for example by *Colletotrichum lindemuthanium*; Cycloconium diseases, caused for example by *Cycloconium oleaginum*; Diaporthe diseases, caused for example by *Diaporthe citri*; Drechslera, Syn: *Helminthosporium*) or *Cochliobolus miyabeanus*; Elsinoe diseases, caused for example by *Elsinoe fawcettii*; Gloeosporium diseases, caused for example by *Gloeosporium laeticolor*; Glomerella diseases, caused for example by *Glomerella cingulata*; Guignardia diseases, caused for example by *Guignardia bidwelli*; Leptosphaeria diseases, caused for example by *Leptosphaeria maculans; Leptosphaeria nodorum*; Magnaporthe diseases, caused for example by *Magnaporthe grisea*; Mycosphaerella diseases, caused for example by *Mycosphaerella graminicola; Mycosphaerella arachidtola; Mycosphaerella fibensis*; Phaeosphaeria diseases, caused for example by *Phaeosphaera nodorum*; Pyrenophora diseases, caused for example by *Pyrenophora teres*; Ramularia diseases, caused for example by *Ramularia collo-cygni*; Rhynchosporium diseases, caused for example by *Rhynchosporium secalis*; Septoria diseases, caused for example by *Septoria apii* or *Septoria lycopercisi*; Typhula diseases, caused for example by *Typhula incarnata*; Venturia diseases, caused for example by *Venturia inaequalis;*

Root and stem diseases such as: Corticium diseases, caused for example by *Corticium graminearum*; Fusarium diseases, caused for example by *Fusarium oxysporum*; Gaeumannomyces diseases, caused for example by *Gaeumannomyces graminis*; Rhizoctonia diseases, caused for example by *Rhizoctonia solani*; Sarocladium diseases caused for example by *Sarocladium oryzae*; Sclerotium diseases caused for example by *Sclerotium oryzae*; Tapesia diseases, caused for example by *Tapesia acuformis*; Thielavbpsis diseases, caused for example by *Thielaviopsis basicola;*

Ear and panicle diseases including maize cob, such as: Alternaria diseases, caused for example by *Alternaria* spp.; Aspergillus diseases, caused for example by *Aspergillus flavus; Cladosporium diseases, caused for example by Cladosporium* spp.; *Claviceps diseases, caused for example by Claviceps purpurea*; Fusarium diseases, caused for example by *Fusarium culmorum*; Gibberella diseases, caused for example by *Gibberella zeae*; Monographella diseases, caused for example by *Monographella nivalis;*

Smut and bunt diseases such as: Sphacelotheca diseases, caused for example by *Sphacelotheca reiliana*; Tilletia diseases, caused for example by *Tilletia caries;*

Urocystis diseases, caused for example by *Urocystis occulta*; Ustilago diseases, caused for example by *Ustilago nuda;*

Fruit rot and mould diseases such as: Aspergillus diseases, caused for example by *Aspergillus flavus*; Botrytis diseases, caused for example by *Botrytis cinerea*; Penicillium diseases, caused for example by *Penicillium expansum*; Rhizopus diseases caused for example by *Rhizopus stolonifer*; Sclerotinia diseases, caused for example by *Sclerotinia sclerotiorum;*

Verticilium diseases, caused for example by *Verticilium alboatrum;*

Seed and soil borne decay, mould, wilt, rot and damping-off diseases such as: Alternaria diseases, caused for example by *Alternaria brassicicola*; Aphanomyces diseases, caused for example by *Aphanomyces euteiches*;

Ascochyta diseases, caused for example by *Ascochyta lentis*; Aspergillus diseases, caused for example by *Aspergillus flavus*; Cladosporium diseases, caused for example by *Cladosporium herbarum*; Cochliobolus diseases, caused for example by *Cochliobolus sativus* (Conidiaform: *Drechslera, Bipolaris* Syn: *Helminthosporium*); Colletotrichum diseases, caused for example by *Colletotrichum coccodes*; Fusarium diseases, caused for example by *Fusarium culmorum*; Gibberella diseases, caused for example by *Gibberella zeae*; Macrophomina diseases, caused for example by *Macrophomina phaseolina*; Monographella diseases, caused for example by *Monographella nivalis*; Penicillium diseases, caused for example by *Penicillium expansum*; Phoma diseases, caused for example by *Phoma lingam; Phomopsis diseases, caused for example by Phomopsis sojae*; Phytophthora diseases, caused for example by *Phytophthora cactorum*; Pyrenophora diseases, caused for example by *Pyrenophora graminea*; Pyricularia diseases, caused for example by *Pyricularia oryzae*; Pythium diseases, caused for example by *Pythium ultimum*; Rhizoctonia diseases, caused for example by *Rhizoctonia solani*; Rhizopus diseases, caused for example by *Rhizopus oryzae*; Sclerotium diseases, caused for example by *Sclerotium rolfsii*; Septoria diseases, caused for example by *Septoria nodorum*; Typhula diseases, caused for example by *Typhula incarnata*; Verticillium diseases, caused for example by *Verticillium dahliae*; Canker, broom and dieback diseases such as: Nectria diseases, caused for example by *Nectria galligena;*

Blight Diseases Such as:

- Monilinia diseases, caused for example by *Monilinia laxa;*
- Leaf blister or leaf curl diseases such as: Exobasidium diseases caused for example by *Exobasidium vexans*; Taphrina diseases, caused for example by *Taphrina deformans;*
- Decline diseases of wooden plants such as:
- Esca diseases, caused for example by *Phaemoniella clamydospora, Phaeomoniella clamydospora, Phaeoacremonium aleophilum* and *Fomitiporia mediterranea;*
- Eutypa dyeback, caused for example by *Eutypa lata*; Dutch elm disease, caused for example by *Ceratocystsc ulmi*; Ganoderma diseases caused for example by *Ganoderma boninense*; Diseases of flowers and seeds such as: Botrytis diseases, caused for example by *Botrytis cinerea;*
- Diseases of tubers such as: Rhizoctonia diseases, caused for example by *Rhizoctonia solani* Helminthosporium diseases, caused for example by *Helminthospohum solani.*

Diseases of Tubers Such as:

- Rhizoctonia diseases caused for example by *Rhizoctonia solani*; Helminthosporium diseases caused for example by *Helminthospohum solani;*

Club Root Diseases Such as:

- Plasmodiophora diseases, caused for example by *Plasmodiophora brassicae.*

The compounds of the invention may be active against a broad spectrum of fungal diseases of plants. Alternatively, they may be active specifically against certain specific fungal diseases.

Particular fungal diseases against which the compounds of the invention may be useful include: wheat leaf blotch (*Septoria tritici*), wheat brown rust (*Puccinia triticina*), wheat stripe rust (*Puccinia striiformis*), scab of apple (*Venturia inaequalis*), powdery mildew of grapevine (*Uncinula necator*), barley scald (*Rhynchosporium secalis*), blast of rice (*Magnaporthe grisea*), rust of soybean (*Phakopsora pachyrhizi*), glume blotch of wheat (*Leptosphaeria nodorum*), powdery mildew of wheat (*Blumeria graminis* f. sp. *tritici*), powdery mildew of barley (*Blumeria graminis* f. sp. *hordei*), powdery mildew of cucurbits (*Erysiphe dehor acearum*), anthracnose of cucurbits (*Glomerella lagenarium*), leaf spot of beet (*Cercospora beticola*), early blight of tomato (*Alternaria solani*), and spot blotch of barley (*Cochliobolus sativus*).

In additional to their fungicidal activity, the compounds of the invention may also have activity against other microbes, e.g. bacteria.

The fungicidal compounds of the invention may also be used in the treatment of fungal diseases of humans and animals (e.g. mammals). Likewise, the bactericidal compounds of the invention may be used in the treatment of bacterial diseases of humans and animals.

Thus, the invention includes a method of treating a fungal or bacterial disease, the method comprising of administering a therapeutic amount of an antifungal agent of the invention to a subject (e.g. a human subject) in need thereof. The compound may be formulated for topical administration to the infected area of the body or it may be formulated for oral or parenteral administration.

Synthesis

The skilled person will appreciate that adaptation of methods known in the art could be applied in the manufacture of the compounds of the present invention.

For example, the skilled person will be immediately familiar with standard textbooks such as "Comprehensive Organic Transformations—A Guide to Functional Group Transformations", RC Larock, Wiley-VCH (1999 or later editions); "March's Advanced Organic Chemistry—Reactions, Mechanisms and Structure", MB Smith, J. March, Wiley, (5th edition or later editions); "Advanced Organic Chemistry, Part B, Reactions and Synthesis", FA Carey, RJ Sundberg, Kluwer Academic/Plenum Publications, (2001 or later editions); "Organic Synthesis—The Disconnection Approach", S Warren (Wiley), (1982 or later editions); "Designing Organic Syntheses" S Warren (Wiley) (1983 or later editions); "Heterocyclic Chemistry", J. Joule (Wiley 2010 edition or later editions); ("Guidebook To Organic Synthesis" R K Mackie and D M Smith (Longman) (1982 or later editions), etc., and the references therein as a guide.

The skilled person is familiar with a range of strategies for synthesising organic and particularly heterocyclic molecules and these represent common general knowledge as set out in text books such as Warren "Organic Synthesis: The Disconnection Approach"; Mackie and Smith "Guidebook to Organic Chemistry"; and Clayden, Greeves, Warren and Wothers "Organic Chemistry".

The skilled person will exercise his/her judgement and skill as to the most efficient sequence of reactions for the synthesis of a given target compound and will employ protecting groups as necessary. This will depend inter alia on factors such as the nature of other functional groups present in a particular substrate. Clearly, the type of chemistry involved will influence the choice of reagent that is used in the said synthetic steps, the need, and type, of protecting groups that are employed, and the sequence for accomplishing the protection/deprotection steps. These and other reaction parameters will be evident to the skilled person by reference to standard textbooks and to the examples provided herein.

Sensitive functional groups may need to be protected and deprotected during synthesis of a compound of the invention. This may be achieved by conventional methods, for example as described in "Protective Groups in Organic Synthesis" by TW Greene and PGM Wuts, John Wiley & Sons Inc. (1999), and references therein.

Throughout this specification these abbreviations have the following meanings:

Throughout this specification these abbreviations have the following meanings:

PyBOP - benzotriazol-1-yl-oxytripyrrolidinophosphonium hexafluorophosphate
HATU - (1-[Bis(dimethylamino)methylene]-1H-1,2,3-triazolo[4,5-b]pyridinium 3-oxidhexafluorophosphate
DIPEA - N,N-diisopropylethylamine
DMSO - dimethylsulfoxide
aq .- aqueous
conc. - concentrated
DCM - dichloromethane
DMF - N,N-dimethylformamide
h - hour
min - minute
LCMS - liquid chromatography mass spectrometry
rt - room temperature
PE - petroleum ether
THF - tetrahydrofuran
XPHos - 2-Dicyclohexylphosphino-2',4',6'-triisopropylbiphenyl Certain compounds of the invention can be accessed according to or analogously to the general synthetic schemes below. Certain compounds of the invention can be accessed via the synthetic intermediates described in Examples 1 to 46 below.

General Synthetic Schemes

Compounds of formula I can be made according to schemes A to D.

Quinolines of formula A are commercially available. Activating group X on quinoline A can be used as a handle to introduce the $Z^1$—$Z^2$—$R^6$ group and provide quinoline B. $Z^1$—$Z^2$—$R^6$ can be introduced using coupling reactions (e.g. Buchwald-Hartwig, Suzuki) with a suitable coupling partner (e.g. a boronic ester) in which case X may be a halogen, e.g. bromide, or a boronic ester. Alternatively, $Z^1$—$Z^2$—$R^6$ can be introduced using an addition elimination reaction, in which case X may be a leaving groups, such as a halogen, e.g chloro, or a sulfonate, e.g. methylsulfonate. Addition/elimination reactions are particularly appropriate where $Z^1$—$Z^2$—$R^6$ is $Z^2R^6$ and $Z^2$ is O, S or $NR^7$. In these reactions, quinoline A is typically treated with $R^6$—$Z^2$—H in the presence of a base (e.g. NaH or $Na_2CO_3$). Reduction of the nitro group, e.g. using Fe and $NH_4Cl$ using Pd/C and $H_2$, then provides amine C. Where $R^4$ is not H, $R^4$ can be introduced at this stage, e.g. using an alkyl halide. Amide formation with picolinic acid derivative D (e.g. using LiHMDS) or E (e.g. using HATU) forms compounds of formula F, a subset of compounds of the invention.

Scheme A

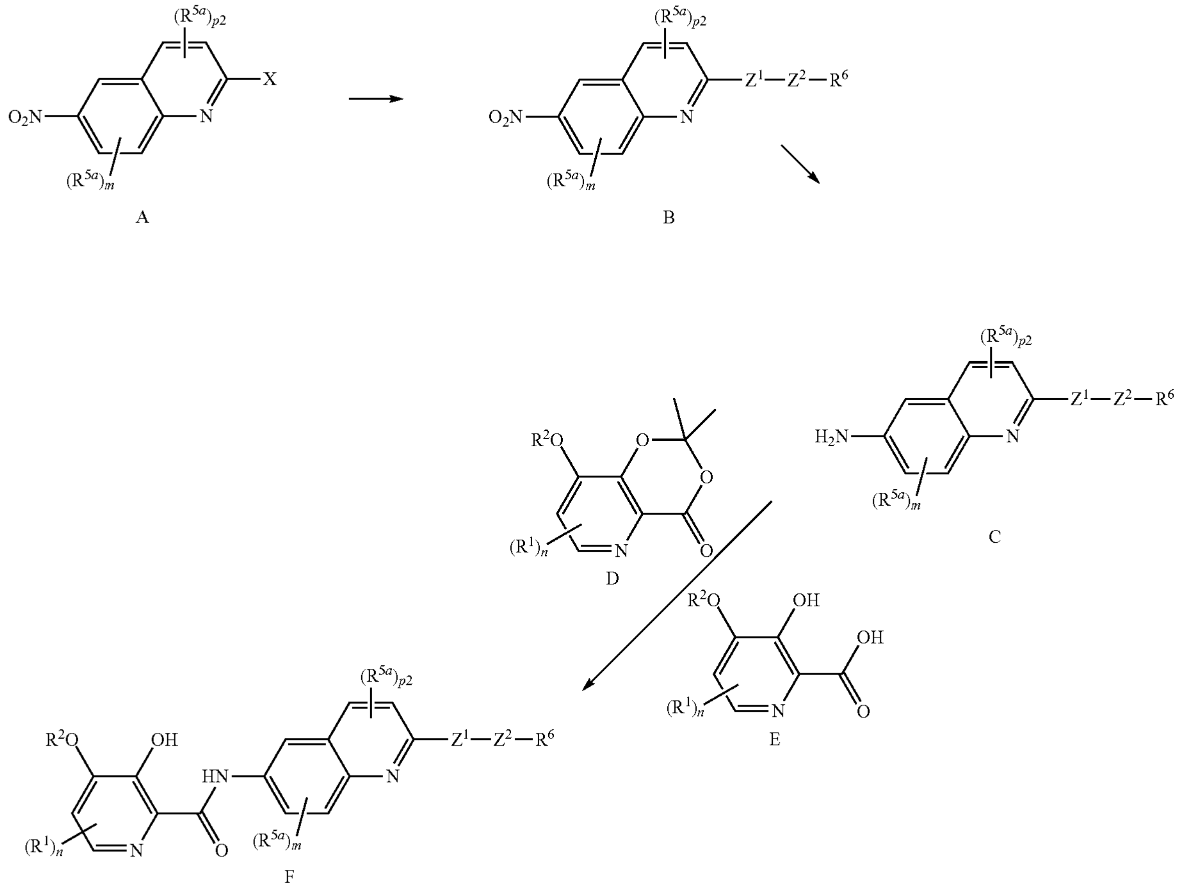

A B C D E F

Alternatively, compounds of the invention can be accessed via quinoline G. Amine formation, e.g. by heating with acetamide and $K_2CO_3$ at 200° C. can provide amine H. Palladium coupling reaction (e.g. Suzuki) with an appropriate halide or boronic ester can provide a compound of formula J. Where $R^4$ is not H, $R^4$ can be introduced at this stage, e.g. using an alkyl halide. Amide formation with picolinic acid derivative D (e.g. using LiHMDS) or E (e.g. using HATU) forms compounds of formula K, a subset of compounds of the invention.

Scheme B

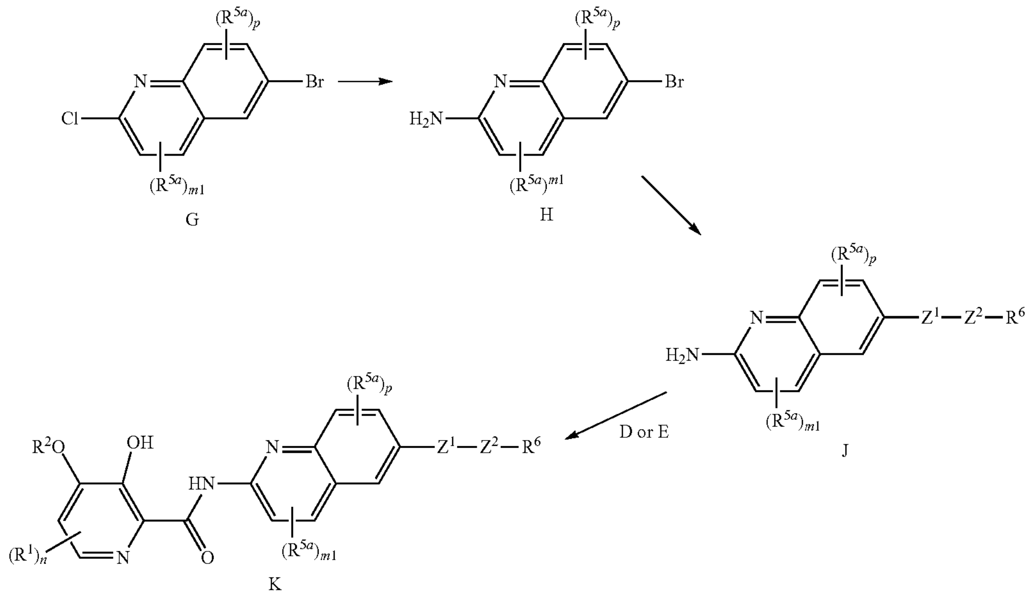

In a further alternative, compounds of the invention can be accessed via quinoline L. A Palladium coupling reaction (e.g. Suzuki) with an appropriate halide or boronic ester can provide a compound of formula M, a subset of compounds of the invention. Boc deprotection provides the corresponding amine N. Where $R^4$ is not H, $R^4$ can be introduced at this stage, e.g. using an alkyl halide. Amide formation with picolinic acid derivative D (e.g. using LiHMDS) or E (e.g. using HATU) forms compounds of formula 0, a subset of compounds of the invention.

Scheme C

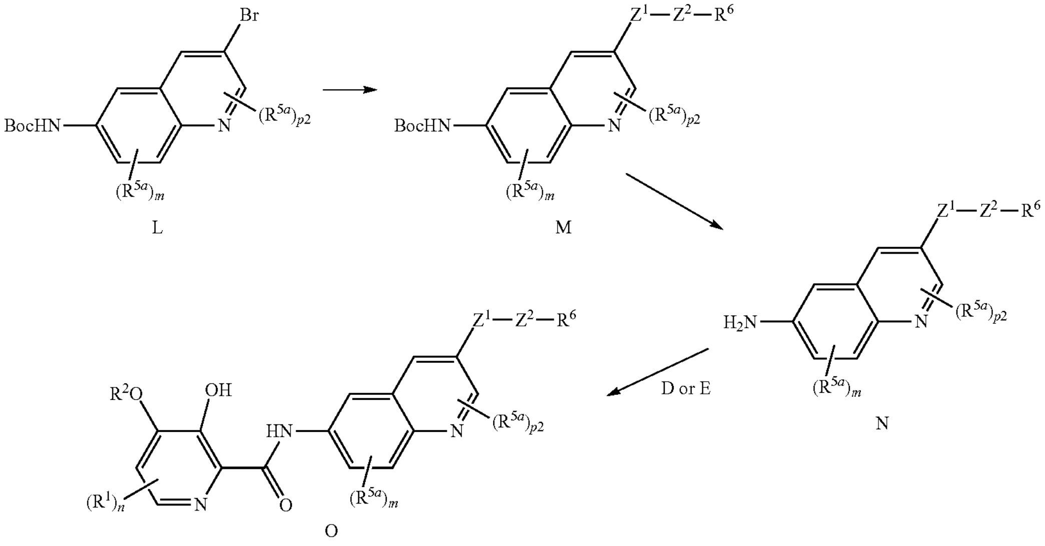

Compounds of formulae F, K and O (generalised below as formula P) can be converted to compounds of formula Q (e.g. using $Ac_2O$) or R (e.g. using either thiophosgene where $Y^2$ is S or triphosgene where $Y^2$ is O), two further subsets of compounds of the invention.

Scheme D

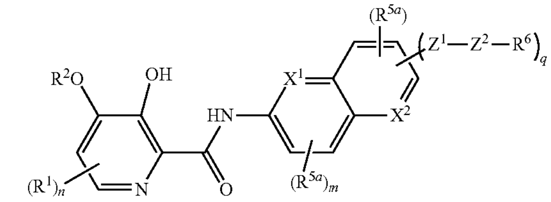

P

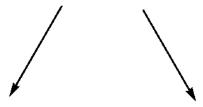

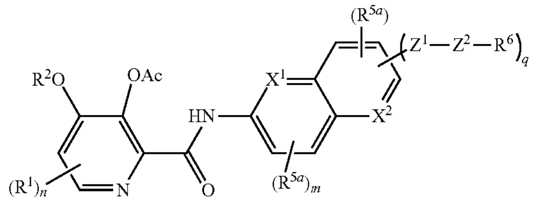

Q

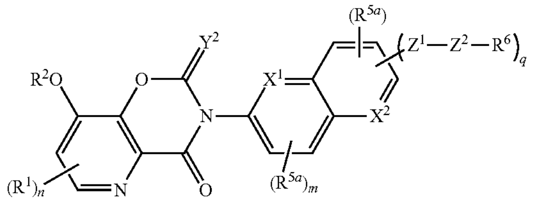

R

EXAMPLES

General Methods

Flash chromatography was carried out using a Biotage Isolera 4, with Biotage® SNAP KP-Sil cartridges, packed with 50 μm silica particles with a surface area of 500 $m^2/g$, or alternative cartridges (e.g. Puriflash, produced by Interchim) where stated, or using silica gel (40-63 μm particles). Visualisation was carried out with UV light (254 nm) and by staining with either potassium permanganate, phosphomolybdic acid (PMA) or ninhydrin solutions.

All $^1H$ NMR spectra were obtained on a Bruker AVIII 400 with 5 mm QNP or Bruker AVI 500 with 5 mm QNP. Chemical shifts are expressed in parts per million (δ) and are referenced to the solvent. Coupling constants J are expressed in Hertz (Hz).

LCMS was carried out on a Waters Alliance ZQ MS, using a YMC-Triart C18 50×2 mm, 5 micron LC column (solvent: 5-90% gradient of acetonitrile in water (with 1% by volume of 28% (by weight) aqueous ammonia solution)) by Method A, or (solvent: 5-90% gradient of acetonitrile in water (with 1% formic acid)) by Method B. Flow rate: 0.8 mL/min. Wavelengths were 254 and 210 nm.

Method A (5 Minute Basic pH)

Column: YMC-Triart C18 50×2 mm, 5 μm. Flow rate: 0.8 mL/min. Injection volume: 5 μL.

| Mobile Phase | | |
|---|---|---|
| | A | $H_2O$ |
| | B | $CH_3CN$ |
| | C | 50% $H_2O$/ 50% $CH_3CN$ + 1.0% ammonia (aq.) |

| Time (min) | A (%) | B (%) | C (%) |
|---|---|---|---|
| 0 | 95 | 0 | 5 |
| 4.0 | 0 | 95 | 5 |
| 4.4 | 0 | 95 | 5 |
| 4.5 | 95 | 5 | 0 |
| 4.5 | | STOP | |

Method B (5 Minute Acidic pH)

Column: YMC-Triart C18 50×2 mm, 5 μm. Flow rate: 0.8 mL/min. Injection volume: 5 μL.

| Mobile Phase | | |
|---|---|---|
| | A | $H_2O$ |
| | B | $CH_3CN$ |
| | C | 50% $H_2O$/ 50% $CH_3CN$ + 1.0% formic acid |

| Time (min) | A (%) | B (%) | C (%) |
|---|---|---|---|
| 0 | 95 | 0 | 5 |
| 4.0 | 0 | 95 | 5 |

-continued

| | | | |
|---|---|---|---|
| 4.4 | 0 | 95 | 5 |
| 4.5 | 95 | 5 | 0 |
| 4.5 | | STOP | |

Alternatively MS was carried on a Waters Acquity UPLC-QDA UV-MS system using Method C (high pH) or Method D (low pH):

Method C (3.5 Minute Basic pH)

| Mobile phases: Water (A)/Acetonitrile (B) both with 0.1% (v/v) Ammonia | | | |
|---|---|---|---|
| Time | % A | % B | Flow rate (mL/min) |
| Initial | 98 | 2 | 1.0 |
| 0.2 | 98 | 2 | 1.0 |
| 2.5 | 2 | 98 | 1.0 |
| 3.0 | 2 | 98 | 1.0 |
| 3.1 | 98 | 2 | 1.0 |
| 3.5 | 98 | 2 | 1.0 |

Column: BEH C18 2.1 × 50 mm, 1.7 μm @ 50° C.

Column: BEH C18 2.1×50 mm, 1.7 μm @ 50° C.

Method D (3.5 Minute Acidic pH)

| Mobile phases: Water (A)/Acetonitrile (B) both with 0.1% (v/v) Formic Acid | | | |
|---|---|---|---|
| Time | % A | % B | Flow rate (mL/min) |
| Initial | 98 | 2 | 1.0 |
| 0.2 | 98 | 2 | 1.0 |
| 2.5 | 2 | 98 | 1.0 |
| 3.0 | 2 | 98 | 1.0 |
| 3.1 | 98 | 2 | 1.0 |
| 3.5 | 98 | 2 | 1.0 |

Column: CSH C18 2.1 × 50 mm, 1.7 μm @ 50° C.

All reagents were obtained from commercial suppliers and used as supplied unless otherwise stated.

All compounds are named using ChemBioDraw Ultra 14.0.

Intermediate A: 2-(4-Fluorophenoxy)-6-nitroquinoline

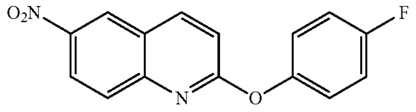

A suspension of sodium hydride (60% in mineral oil) (67.1 mg, 1.68 mmol) in anhydrous DMF (2 mL) was treated with a solution of 4-fluorophenol (134 mg, 1.20 mmol) in DMF (0.5 mL). The reaction mixture was stirred at rt for 15 min and then 2-chloro-6-nitroquinoline (250 mg, 1.20 mmol) was added portion-wise. The reaction mixture was stirred for 4 h at rt and then quenched by pouring into water (20 mL). A precipitate was formed, and the resulting mixture was stirred for 30 min and then filtered. The solid was washed with water (3×50 mL) and dried under vacuum to afford the title compound as a beige solid (260 mg, 76%).

1H NMR (DMSO-$d^6$): 9.04 (d, J=2.6 Hz, 1H), 8.73 (d, J=8.9 Hz, 1H), 8.36 (dd, J=9.2, 2.7 Hz, 1H), 7.79 (d, J=9.2 Hz, 1H), 7.50 (d, J=8.9 Hz, 1H), 7.47-7.15 (m, 4H).

Intermediates B-D

The following Intermediates were prepared using the general method described in Intermediate A from commercial starting materials.

| Intermediate No | Compound | $^1H$ NMR/LCMS |
|---|---|---|
| B | 2-ethoxy-6-nitroquinoline 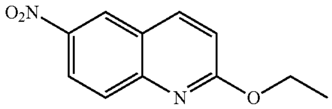 [SMILES: CCOc1ccc2cc([N+](=O)[O-])ccc2n1] | LCMS (Method B): 3.15 min (219.1, $MH^+$). |
| C | 6-nitro-2-propoxyquinoline 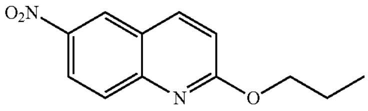 [SMILES: CCCOc1ccc2cc([N+](=O)[O-])ccc2n1] | LCMS (Method B): 3.64 min (233.3, $MH^+$). |
| D | 2-butoxy-6-nitroquinoline 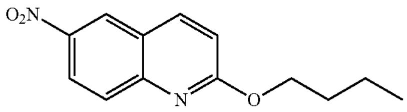 [SMILES: CCCCOc1ccc2cc([N+](=O)[O-])ccc2n1] | LCMS (Method B): 3.89 min (247.1, $MH^+$). |

Intermediate E: 2-Isopropoxy-6-nitroquinoline

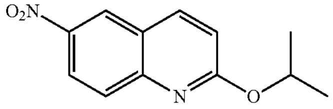

A suspension of potassium tert-butoxide (32 mg, 0.29 mmol) in DMF (0.5 ml) was treated with 2-propanol (20 μl, 0.26 mmol) and the mixture was stirred at rt for 30 min. 2-Chloro-6-nitroquinoline (50 mg, 0.24 mmol) was then added in one portion and the reaction mixture was stirred at rt for 4 h. The reaction was quenched with water (3 mL) and a precipitate formed. The resulting mixture was stirred for 30 mins and then EtOAc (3 mL) was added. The aqueous layer was extracted with EtOAc (3×3 mL) and the combined organics were dried ($MgSO_4$) and evaporated in vacuo to afford the title compound as a brown solid (44 mg, 79%).

LCMS (Method B): 3.64 min, (333.0, $MH^+$).

Intermediates F-I

The following Intermediates were prepared using the general method described in Intermediate E from commercial starting materials.

| Intermediate No | Compound | $^1H$ NMR/LCMS |
|---|---|---|
| F | (2-((3-methylbutan-2-yl)oxy)-6-nitroquinoline 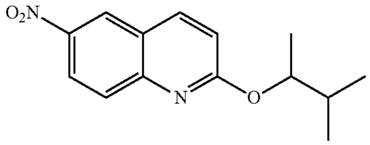 [SMILES: CC(C)C(C)Oc1ccc2cc([N+](=O)[O-])ccc2n1] | LCMS (Method B): 4.09 min (261.1, $MH^+$). |
| G[a] | 2-(isopentyloxy)-6-nitroquinoline 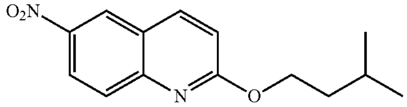 [SMILES: CC(C)CCOc1ccc2cc([N+](=O)[O-])ccc2n1] | LCMS (Method B): 4.09 min (261.1, $MH^+$). |
| H | 2-(sec-butoxy)-6-nitroquinoline 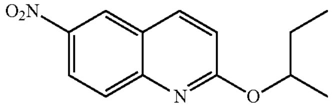 [SMILES: CCC(C)Oc1ccc2cc([N+](=O)[O-])ccc2n1] | LCMS (Method B): 3.91 min (247.0, $MH^+$). |
| I | 2-isobutoxy-6-nitroquinoline 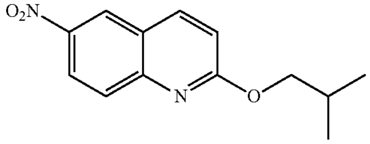 [SMILES: CC(C)COc1ccc2cc([N+](=O)[O-])ccc2n1] | $^1H$ NMR $\delta_H$ (DMSO-d$^6$): 8.96 (d, J = 2.6 Hz, 1H), 8.54 (d, J = 8.9 Hz, 1H), 8.38 (dd, J = 9.2, 2.7 Hz, 1H), 7.92 (t, J = 10.5 Hz, 1H), 7.22 (d, J = 8.9 Hz, 1H), 4.26 (d, J = 6.7 Hz, 2H), 2.12 (dp, J = 13.4, 6.7 Hz, 1H), 1.02 (d, J = 6.7 Hz, 6H); LCMS (Method B): 3.90 min, (247.0, $MH^+$). |

[a]Reaction stirred at rt for 48 h

Intermediate J: N-(4-fluorophenyl)-N-methyl-6-nitroquinolin-2-amine

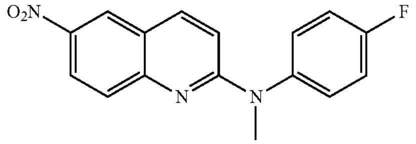

A mixture of 2-chloro-6-nitroquinoline (50 mg, 0.24 mmol), acetic acid (1.4 μl, 0.024 mmol) and 4-fluoro-N-methylaniline (29 μl, 0.24 mmol) in dioxane (2.4 mL) was heated at 150° C. for 3 h under microwave irradiation. The reaction mixture was allowed to cool to rt and then concentrated under vacuum to afford the title compound as a pale brown solid (50 mg, 70%).

LCMS (Method B): 3.60 min, (298.1, $MH^+$).

Intermediate K: 2-((4-Fluorophenyl)thio)-6-nitroquinoline

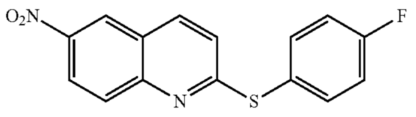

A mixture of 2-chloro-6-nitroquinoline (50 mg, 0.24 mmol), potassium carbonate (16.6 mg, 0.12 mmol) and 4-fluorobenzenethiol (26 μl, 0.24 mmol) in DMF (0.5 mL) was stirred at rt for 18 h. The reaction was diluted with water (4 mL) and EtOAc (4 mL), the two layers were separated, and the aqueous layer was further extracted with EtOAc (3×3 mL). The combined organics were dried ($MgSO_4$) and concentrated under reduced pressure to afford the title compound as a yellow solid (58 mg, 81%).

LCMS (Method B): 3.62 min, (301.0, $MH^+$).

Intermediate L: 2-(4-Fluorophenoxy)quinolin-6-amine

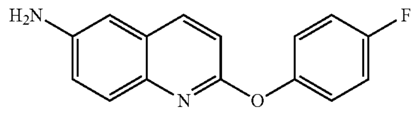

A solution of Intermediate A (260 mg, 0.915 mmol) in methanol (2.7 mL)/THF (5.4 mL)/water (1.1 mL) was treated with ammonium chloride (294 mg, 5.49 mmol) and iron (306 mg, 5.49 mmol). The reaction mixture was heated at 60° C. for 18 h. After cooling to rt, the mixture was filtered through Dicalite®, washing with EtOAc. The filtrate was washed with water, dried ($MgSO_4$), and concentrated under reduced pressure to afford the title compound as a beige solid (185 mg, 80%).

LCMS (Method D): 1.62 min, (255.1, $MH^+$).

Intermediates M-W

The following Intermediates were prepared using the general method described in Intermediate L from the appropriate intermediate.

| Intermediate No | Compound | $^1H$ NMR/LCMS |
|---|---|---|
| M | 2-ethoxyquinolin-6-amine 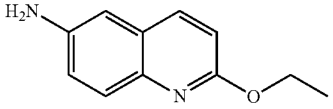 | LCMS (Method B): 1.90 min (189.0, $MH^+$). |
| N | 2-propoxyquinolin-6-amine 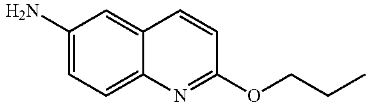 | LCMS (Method B): 2.27 min (203.0, $MH^+$). |
| O | 2-butoxyquinolin-6-amine 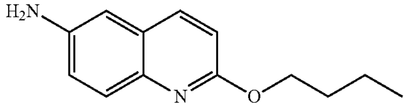 | LCMS (Method B): 2.68 min (217.1, $MH^+$). |
| P | 2-isopropoxyquinolin-6-amine 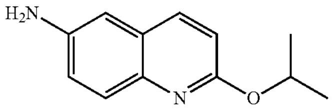 | LCMS (Method B): 1.90 min (189.0, $MH^+$). |
| Q | 2-((3-methylbutan-2-yl)oxy)quinolin-6-amine 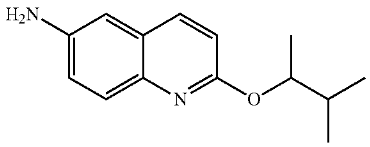 | LCMS (Method B): 2.97 min (231.1, $MH^+$). |

-continued

| Intermediate No | Compound | $^1$H NMR/LCMS |
|---|---|---|
| R | 2-(isopentyloxy)quinolin-6-amine 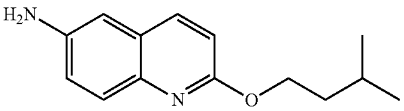 | LCMS (Method B): 3.03 min (231.1, $MH^+$). |
| S | N2-(4-fluorophenyl)-N2-methylquinoline-2,6-diamine 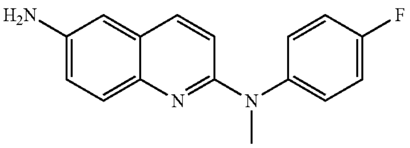 [SMILES: CN(c1ccc(F)cc1)c1ccc2cc(N)ccc2n1] | LCMS (Method B): 1.46 min (268.1, $MH^+$). |
| T | 2-((4-fluorophenyl)thio)quinolin-6-amine 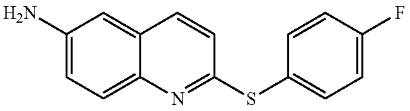 [SMILES: Nc1ccc2nc(Sc3ccc(F)cc3)ccc2c1] | LCMS (Method B): 2.82 min (271.0, $MH^+$). |
| U | 2-chloroquinolin-6-amine 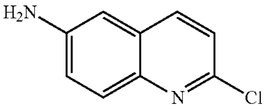 [SMILES: Nc1ccc2nc(Cl)ccc2c1] | LCMS (Method B): 2.02 min (179.0, $MH^+$). |
| V | 2-(sec-butoxy)quinolin-6-amine 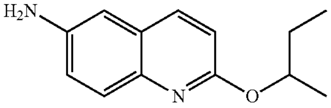 | LCMS (Method B): 2.70 min (217.1, $MH^+$). |
| W | 2-isobutoxyquinolin-6-amine 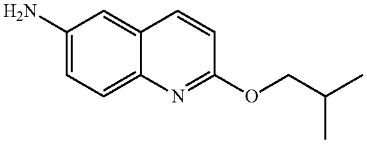 [SMILES: CC(C)COc1ccc2cc(N)ccc2n1] | LCMS (Method B): 2.69 min (217.1, $MH^+$). |

Intermediate X: tert-Butyl (3-benzylquinolin-6-yl)carbamate

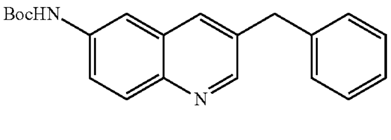 [SMILES: CC(C)(C)OC(=O)Nc1ccc2ncc(Cc3ccccc3)cc2c1]

A mixture of benzylboronic acid pinacol ester (506 mg, 2.32 mmol), potassium phosphate tribasic (657 mg, 3.09 mmol), XPHOS (36.9 mg, 0.077 mmol), palladium(II) acetate (8.7 mg, 0.039 mmol) and tert-butyl (3-bromoquinolin-6-yl)carbamate (250 mg, 0.774 mmol) in THF (3 mL)/water (0.2 mL) was degassed and then heated at 90° C. for 18 h. The reaction was allowed to cool to rt and then filtered through Dicalite®, washing with EtOAc (30 mL). The filtrate was dried ($MgSO_4$) and concentrated under reduced pressure to afford a crude residue of the title compound (assumed quantitative yield) which was taken on to the next step without further purification.

LCMS (Method D): 3.02 min, (335.1, $MH^+$).

Intermediate Y: 3-Benzylquinolin-6-amine

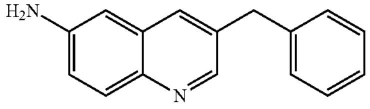 [SMILES: Nc1ccc2ncc(Cc3ccccc3)cc2c1]

A solution of crude Intermediate X (220 mg, 0.658 mmol) in HCl (4M in dioxane) (4.11 mL, 16.5 mmol) was stirred at rt for 2 h. The reaction mixture was neutralised with 1M aq. solution of NaOH and diluted with EtOAc (20 mL). The layers were separated, and the aqueous layer was extracted using EtOAc (3×10 mL). The combined organics were dried ($MgSO_4$) and concentrated under reduced pressure to afford a crude residue of the title compound (assumed quantitative yield) which was taken on to the next step without further purification.

LCMS (Method B): 1.77 min, (235.0, $MH^+$).

Intermediate Z: 6-Bromoquinolin-2-amine

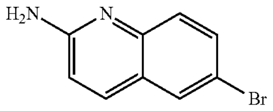 [SMILES: Nc1ccc2cc(Br)ccc2n1]

A mixture of 6-bromo-2-chloro-quinoline (2.0 g, 8.3 mmol), acetamide (9.74 g, 165 mmol) and potassium carbonate (3.4 g, 25 mmol) was heated at 200° C. for 2 h. The reaction mixture was allowed to cool to rt whereupon the mixture solidified. The residue was taken up in DCM (15 mL) and water (10 mL), and the layers separated. The aqueous layer was extracted with DCM (2×15 mL), the combined organic extracts were washed with brine, dried ($MgSO_4$) and concentrated under vacuum to yield the title compound as a beige solid (780 mg, 34%).

$^1$H NMR $\delta_H$ (400 MHz, Chloroform-d) 8.01 (d, J=8.6 Hz, 1H), 7.83-7.78 (m, 1H), 7.78-7.73 (m, 1H), 7.61 (dd, J=8.9, 2.2 Hz, 1H), 7.51 (d, J=8.9 Hz, 1H), 4.94 (s, 2H); LCMS (Method B): 1.10 min, (222.9/224.9, $MH^+$).

Intermediate AA: 6-Phenylquinolin-2-amine

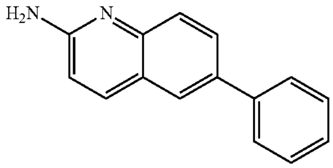 [SMILES: Nc1ccc2cc(-c3ccccc3)ccc2n1]

Intermediate Z (210 mg, 0.94 mmol), sodium carbonate (300 mg, 2.83 mmol) and phenylboronic acid (345 mg, 2.83 mmol) were taken up in 1,4-dioxane (9 mL)/water (3 mL) and degassed for 10 min. Tetrakis(triphenylphosphine)palladium (109 mg, 0.094 mmol) was added and the reaction heated to 80° C. overnight. The reaction was cooled to rt, water (5 mL) was added and the mixture was extracted with EtOAc (3×15 mL). The combined organics were dried ($MgSO_4$) and concentrated under vacuum. The residue was purified by column chromatography ($SiO_2$, 0-60% EtOAc in PE), to give the title compound as a beige solid (180 mg, 87%).

$^1$H NMR $\delta_H$ (400 MHz, DMSO-d$^6$) 7.79-7.56 (m, 1H), 7.32 (d, J=4.6 Hz, 5H), 7.22 (dd, J=8.1, 4.9 Hz, 3H), 7.10 (t, J=4.2 Hz, 1H); LCMS (Method B): 1.16 min, (221.0, $MH^+$).

Intermediate AB: 6-Benzylquinolin-2-amine

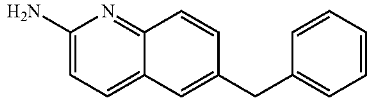 [SMILES: Nc1ccc2cc(Cc3ccccc3)ccc2n1]

Intermediate Z (900 mg, 4.03 mmol), cesium carbonate (3.94 g, 12.1 mmol) and benzylboronic acid pinacol ester (2.69 mL, 12.1 mmol) were taken up in dioxane (20 mL)/water (7 mL) and degassed for 5 minutes. [1,1'-Bis(diphenylphosphino)ferrocene]dichloropalladium(II), complex with dichloromethane (659 mg, 0.807 mmol) was added and the reaction mixture was heated at 80° C. for 18 h. The reaction was cooled to rt, water (10 mL) was added and the mixture was extracted with EtOAc (3×15 mL). The combined organic extracts were dried ($MgSO_4$) and concentrated under vacuum. The residue was purified by column chromatography ($SiO_2$, 0-60% EtOAc in PE), to give the title compound as a light yellow solid (492 mg, 52%).

$^1$H NMR $\delta_H$ (400 MHz, DMSO-d$^6$) 7.79-7.50 (m, 1H), 7.42 (m, 5H), 7.22 (m, 3H), 7.10 (m, 1H), 4.50 (m, 2H) 3.57 (s, 2H); LCMS (Method B): 1.82 min, (235.1, $MH^+$).

Intermediate AC: 4-Pentylquinolin-2-ol

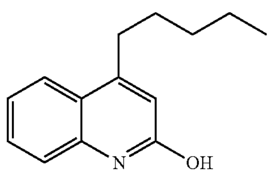 [SMILES: CCCCCc1cc(O)nc2ccccc12]

A solution of 4-methylquinoline-2-ol (1.0 g, 6.3 mmol) in anhydrous THF (10.5 mL) was purged with nitrogen and cooled to −78° C. n-Butyllithium (11.8 mL, 18.9 mmol) was added and the reaction was allowed to warm to rt and stirred for 2 h. 1-Chlorobutane (1.31 mL, 12.6 mmol) was added dropwise and the reaction mixture was stirred for 1 h at rt. Water (20 mL) was added to the reaction mixture, stirred for 10 mins and then extracted with EtOAc (3×10 mL).

The combined extracts were dried ($MgSO_4$) and concentrated under vacuum to give the title compound as an off-white solid (500 mg, 37% yield). LCMS (Method B): 2.65 min, (216.1, $MH^+$).

Intermediate AD: 6-Nitro-4-pentylquinolin-2-ol

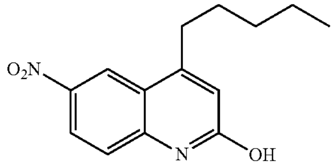 [SMILES: CCCCCc1cc(O)nc2ccc([N+](=O)[O-])cc12]

A mixture of Intermediate AC (500 mg, 2.32 mmol) and sulfuric acid (7.43 mL, 139 mmol) was cooled in an ice/methanol bath and water (0.5 mL) was added followed by nitric acid (97 μL, 2.32 mmol) in a dropwise manner. The reaction mixture was stirred for 2 h and then poured onto a water/ice mixture (50 mL). A precipitate formed, which was filtered and dried under vacuum to give the title compound as a pale yellow solid (410 mg, 68%). LCMS (Method B): 2.80 min, (261.1, $MH^+$).

Intermediate AE: 2-chloro-6-nitro-4-pentylquinoline

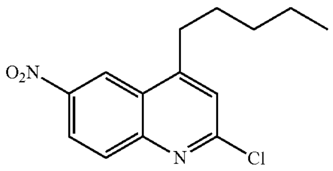 [SMILES: CCCCCc1cc(Cl)nc2ccc([N+](=O)[O-])cc12]

A mixture of Intermediate AD (410 mg, 1.58 mmol) and phosphorus(V) oxychloride (7.34 mL, 7.88 mmol) was stirred at rt for 18 h. The reaction mixture was added dropwise to ice water (10 mL) and the resulting mixture was neutralised with a saturated aqueous solution of NaOH. The mixture was extracted with EtOAc (3×5 mL) and the combined organic extracts were dried ($MgSO_4$) and concentrated under reduced pressure to afford the title compound as an off-white solid (350 mg, 80%). LCMS (Method B): 4.01 min (279.1, $MH^+$).

Intermediates AF-AJ

The following Intermediates were prepared using the general method described in Intermediate A from commercial starting materials.

| Intermediate No | Compound | $^1H$ NMR/LCMS |
|---|---|---|
| AF | 2-(2-chlorophenoxy)-6-nitroquinoline 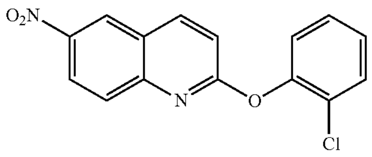 [SMILES: O=[N+]([O-])c1ccc2nc(Oc3ccccc3Cl)ccc2c1] | LCMS (Method B): 3.58 min (301.0, $MH^+$). |
| AG | 2-(4-fluorophenoxy)-6-nitro-4-pentylquinoline 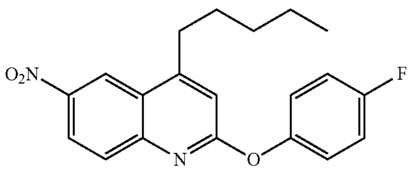 [SMILES: CCCCCc1cc(Oc2ccc(F)cc2)nc2ccc([N+](=O)[O-])cc12] | LCMS (Method B): 4.37 min (355.1, $MH^+$). |
| AH | 2-(2-methoxyphenoxy)-6-nitroquinoline 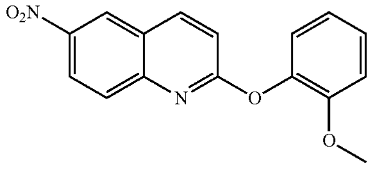 [SMILES: COc1ccccc1Oc1ccc2cc([N+](=O)[O-])ccc2n1] | $^1H$ NMR $\delta_H$ (DMSO-$d^6$): 8.74 (d, J = 2.5 Hz, 1H), 8.38 (dd, J = 9.2, 2.5 Hz, 1H), 8.28 (d, J = 8.9 Hz, 1H), 7.85 (d, J = 9.2 Hz, 1H), 7.35-7.29 (m, 2H), 7.26 (dd, J = 7.7, 1.4 Hz, 1H), 7.11-7.03 (m, 2H), 3.77 (s, 3H); LCMS (Method B): 3.32 min (297.1, $MH^+$). |
| AI | N-(2-chlorophenyl)-N-methyl-6-nitroquinolin-2-amine 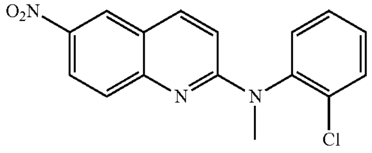 [SMILES: CN(c1ccc2cc([N+](=O)[O-])ccc2n1)c1ccccc1Cl] | 1H NMR $\delta_H$ ($CDCl_3$): 8.58 (d, J = 2.6 Hz, 1H), 8.39 (dd, J = 9.2, 2.5 Hz, 1H), 7.99 (br m, 1H), 7.85 (d, J = 9.2 Hz, 1H), 7.62 (dd, J = 7.6, 1.8 Hz, 1H), 7.50-7.36 (m, 3H), 6.48 (d, J = 9.2 Hz, 1H), 3.68 (s, 3H); LCMS (Method B): 3.80 min (314.1, $MH^+$). |

-continued

| Intermediate No | Compound | $^1$H NMR/LCMS |
|---|---|---|
| AJ | N-(2-chloropyridin-3-yl)-N-methyl-6-nitroquinolin-2-amine 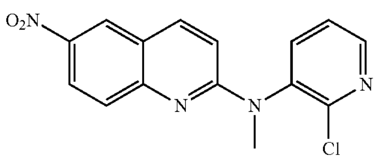 [SMILES: CN(c1ccc2cc([N+](=O)[O-])ccc2n1)c1cccnc1Cl] | $^1$H NMR $\delta_H$ ($CDCl_3$): 8.61 (d, J = 2.6 Hz, 1H), 8.52 (dd, J = 4.7, 1.8 Hz, 1H), 8.40 (dd, J = 9.2, 2.6 Hz, 1H), 7.93 (d, J = 9.1 Hz, 2H), 7.79 (dd, J = 7.8, 1.8 Hz, 1H), 7.46 (dd, J = 7.7, 4.7 Hz, 1H), 6.52 (d, J = 9.1 Hz, 1H), 3.66 (s, 3H); LCMS (Method B): 4.23 min (315.1, $MH^+$). |

Intermediate AK: 2-Chloro-6-nitro-5-propoxyquinoline

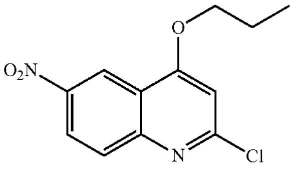 [SMILES: CCCOc1cc(Cl)nc2ccc([N+](=O)[O-])cc12]

A mixture of 7-chloro-4-hydroxy-3-nitroquinoline (250 mg, 1.11 mmol), potassium carbonate (308 mg, 2.23 mmol), and 1-bromopropane (0.202 mL, 2.23 mmol) in DMF (3 mL) was stirred at 80° C. for 18 h. The reaction was allowed to cool to rt, and water was added. The resulting suspension was stirred for 15 min, then filtered. The residue was washed with water and dried under vacuum to afford the title compound as a pale yellow solid (292 mg, 98%).

1H NMR (400 MHz, $CDCl_3$) δ 8.92 (s, 1H), 8.58 (dd, J=8.3, 0.8 Hz, 1H), 7.56-7.49 (m, 2H), 4.28-4.20 (m, 2H), 2.10-1.97 (m, 2H), 1.12 (t, J=7.4 Hz, 3H); LCMS (Method B3): 2.40 min (267.0, $MH^+$).

Intermediates AL-AO

The following Intermediates were prepared using the general method described in Intermediate K from the appropriate intermediate or commercial starting materials.

| Intermediate No | Compound | $^1$H NMR/LCMS |
|---|---|---|
| AL | 2-(2-chlorophenoxy)-6-nitro-5-propoxyquinoline 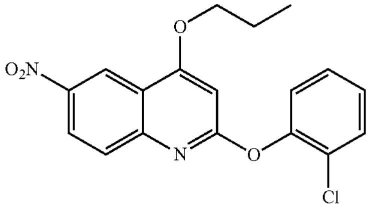 [SMILES: CCCOc1cc(Oc2ccccc2Cl)nc2ccc([N+](=O)[O-])cc12] | $^1$H NMR $\delta_H$ ($CDCl_3$): 8.89 (s, 1H), 8.58 (d, J = 8.9 Hz, 1H), 7.57 (dd, J = 8.0, 1.6 Hz, 1H), 7.39 (dd, J = 7.8, 1.6 Hz, 1H), 7.31 (dd, J = 7.8, 1.6 Hz, 1H), 7.21 (dd, J = 8.0, 1.5 Hz, 1H), 7.02 (dd, J = 9.0, 2.2 Hz, 1H), 6.97 (d, J = 2.1 Hz, 1H), 4.18-4.07 (m, 2H), 2.02-1.90 (m, 2H), 1.05 (t, J = 7.4 Hz, 3H); LCMS (Method B): 2.54 min (359.1, $MH^+$). |
| AM | 2-((2-chlorophenyl)thio)-6-nitroquinoline 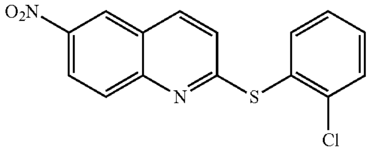 [SMILES: O=[N+]([O-])c1ccc2nc(Sc3ccccc3Cl)ccc2c1] | $^1$H NMR $\delta_H$ ($CDCl_3$): 8.71 (d, J = 2.5 Hz, 1H), 8.44 (dd, J = 9.2, 2.5 Hz, 1H), 8.09 (d, J = 8.7 Hz, 1H), 8.00 (d, J = 9.2 Hz, 1H), 7.82 (dd, J = 7.6, 1.7 Hz, 1H), 7.64 (dd, J = 8.0, 1.4 Hz, 1H), 7.53-7.48 (m, 1H), 7.45-7.39 (m, 1H), 7.14 (d, J = 8.8 Hz, 1H); LCMS (Method A): 3.90 min (317.0, $MH^+$). |
| AN | 2((2-chloropyridin-3-yl)oxy)-6-nitroquinoline 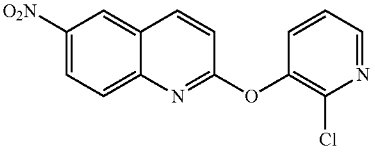 [SMILES: O=[N+]([O-])c1ccc2nc(Oc3cccnc3Cl)ccc2c1] | $^1$H NMR $\delta_H$ ($CDCl_3$): 8.78 (d, J = 2.5 Hz, 1H), 8.44-8.35 (m, 3H), 7.80 (d, J = 9.2 Hz, 1H), 7.74 (dd, J = 8.0, 1.7 Hz, 1H), 7.45-7.39 (m, 2H); LCMS (Method A): 3.45 min (No mass observed). |

-continued

| Intermediate No | Compound | $^1H$ NMR/LCMS |
|---|---|---|
| AO | 2-((2-chloropyridin-3-yl)thio)-6-nitroquinoline 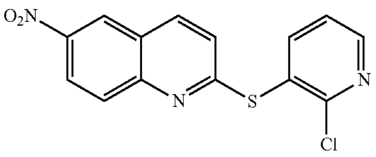 | $^1H$ NMR $\delta_H$ ($CDCl_3$): 8.77 (d, J = 2.5 Hz, 1H), 8.49-8.43 (m, 2H), 8.23 (d, J = 8.6 Hz, 1H), 8.09 (d, J = 9.2 Hz, 1H), 7.82 (dd, J = 8.0, 1.6 Hz, 1H), 7.67 (d, J = 8.7 Hz, 1H), 7.31-7.25 (m, 1H); LCMS (Method A): 3.97 min (318.0, $MH^+$). |

Intermediates AP-AX

The following Intermediates were prepared using the general method described in Intermediate L from the appropriate intermediate.

| Intermediate No | Compound | $^1H$ NMR/LCMS |
|---|---|---|
| AP | 2-(2-chlorophenoxy)quinolin-6-amine 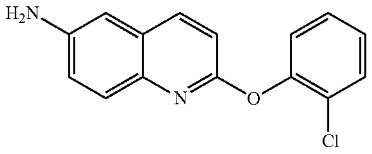 | $^1H$ NMR $\delta_H$ ($CDCl_3$): 7.94 (d, J = 8.8 Hz, 1H), 7.60 (d, J = 8.9 Hz, 1H), 7.51 (dd, J = 7.9, 1.1 Hz, 1H), 7.38-7.30 (m, 2H), 7.24-7.17 (m, 1H), 7.10-7.02 (m, 2H), 6.94 (d, J = 2.6 Hz, 1H), 3.84 (br s, 2H); LCMS (Method B): 2.81 min (271.0, $MH^+$). |
| AQ | 2-(4-fluorophenoxy)-4-pentylquinolin-6-amine 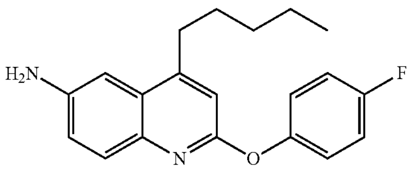 | LCMS (Method B): 3.75 min (325.2, $MH^+$). |
| AR | 2-(2-methoxyphenoxy)quinolin-6-amine 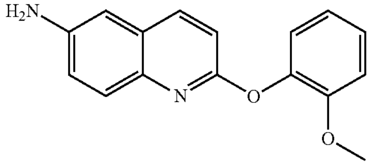 | $^1H$ NMR $\delta_H$ ($CDCl_3$): 7.89 (d, J = 8.8 Hz, 1H), 7.62 (d, J = 8.9 Hz, 1H), 7.26-7.19 (m, 2H), 7.10-6.97 (m, 4H), 6.93 (d, J = 2.6 Hz, 1H), 3.85 (br s, 2H), 3.78 (s, 3H); LCMS (Method A): 2.74 min (267.1, $MH^+$). |
| AS | N2-(2-chlorophenyl)-N2-methylquinoline-2,6-diamine 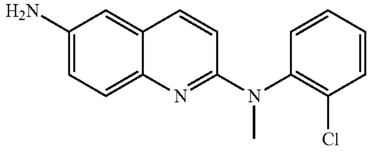 | $^1H$ NMR $\delta_H$ ($CDCl_3$): 7.62-7.54 (m, 2H), 7.41-7.29 (m, 4H), 7.09 (dd, J = 8.8, 2.5 Hz, 1H), 6.83 (d, J = 2.6 Hz, 1H), 6.33 (d, J = 9.1 Hz, 1H), 3.77 (br s, 2H), 3.60 (s, 3H); LCMS (Method A): 3.06 min (284.1, $MH^+$). |

-continued

| Intermediate No | Compound | $^1$H NMR/LCMS |
|---|---|---|
| AT | N2-(2-chloropyridin-3-yl)-N2-methylquinoline-2,6-diamine 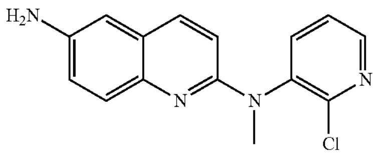 | $^1$H NMR $\delta_H$ ($CDCl_3$): 8.45 (d, J = 5.0 Hz, 1H), 8.01 (v br m, 1H), 7.75 (dd, J = 7.8, 1.8 Hz, 1H), 7.67 (d, J = 9.0 Hz, 1H), 7.40 (dd, J = 7.8, 4.4 Hz, 1H), 7.13 (dd, J = 8.9, 2.4 Hz, 1H), 6.85 (d, J = 2.6 Hz, 1H), 6.36 (d, J = 9.1 Hz, 1H), 3.66 (br s, 3H), $NH_2$ not observed; LCMS (Method A): 0.44 min (285.1, $MH^+$). |
| AU | 2-(2-chlorophenoxy)-5-propoxyquinolin-6-amine 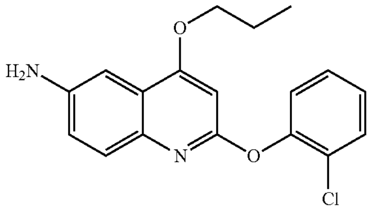 | $^1$H NMR $\delta_H$ ($CDCl_3$): 8.45 (d, J = 8.2 Hz, 1H), 7.53 (dd, J = 8.0, 1.5 Hz, 1H), 7.43 (br m, 1H), 7.37-7.29 (m, 1H), 7.25-7.18 (m, 1H), 7.13 (dd, J = 8.1, 1.1 Hz, 1H), 6.89 (br d, J = 8.8 Hz, 1H), 6.84 (br s, 1H), 3.98-3.83 (m, 2H), 1.84 (br m, 2H), 0.95 (t, J = 7.2 Hz, 3H), $NH_2$ not observed; LCMS (Method B): 2.48 min (329.1, $MH^+$). |
| AV | 2-((2-chlorophenyl)thio)quinolin-6-amine 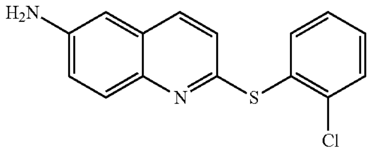 | $^1$H NMR $\delta_H$ ($CDCl_3$): 7.96 (d, J = 8.0 Hz, 1H), 7.79 (d, J = 8.6 Hz, 1H), 7.66 (dd, J = 7.6, 1.4 Hz, 1H), 7.56 (dd, J = 7.9, 1.2 Hz, 1H), 7.40-7.30 (m, 2H), 7.21-7.13 (m, 1H), 6.95 (d, J = 8.6 Hz, 1H), 6.87 (br s, 1H), $NH_2$ not observed; LCMS (Method B): 3.21 min (287.0, $MH^+$). |
| AW | 2-((2-chloropyridin-3-yl)oxy)quinolin-6-amine 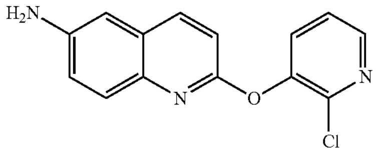 | $^1$H NMR $\delta_H$ ($CDCl_3$): 8.31 (dd, J = 4.7, 1.7 Hz, 1H), 7.98 (d, J = 8.8 Hz, 1H), 7.73 (dd, J = 8.0, 1.7 Hz, 1H), 7.55 (d, J = 8.9 Hz, 1H), 7.35 (dd, J = 8.0, 4.7 Hz, 1H), 7.13 (d, J = 8.8 Hz, 1H), 7.09 (dd, J = 8.9, 2.6 Hz, 1H), 6.95 (d, J = 2.6 Hz, 1H), 3.89 (br s, 2H); LCMS (Method A): 0.49 min (272.0, $MH^+$). |
| AX | 2-((2-chloropyridin-3-yl)thio)quinolin-6-amine 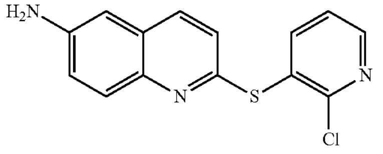 | $^1$H NMR $\delta_H$ ($CDCl_3$): 8.26 (dd, J = 4.7, 1.5 Hz, 1H), 7.92 (d, J = 9.0 Hz, 1H), 7.89 (d, J = 8.7 Hz, 1H), 7.66 (dd, J = 7.9, 1.6 Hz, 1H), 7.49 (d, J = 8.5 Hz, 1H), 7.16 (dd, J = 8.9, 2.6 Hz, 1H), 7.06 (dd, J = 7.9, 4.7 Hz, 1H), 6.92 (d, J = 2.6 Hz, 1H), 4.06 (br s, 2H); LCMS (Method A): 0.45 min (288.0, $MH^+$). |

Example 1: N-(2-ethoxyquinolin-6-yl)-3-hydroxy-4-methoxypicolinamide

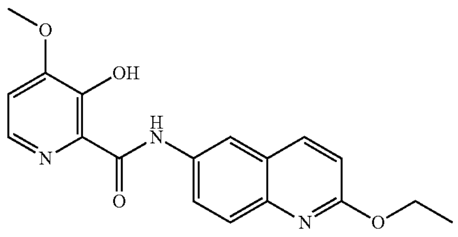 [SMILES: CCOc1ccc2cc(NC(=O)c3nccc(OC)c3O)ccc2n1]

A mixture of Intermediate M (42.8 mg, 0.23 mmol), 3-hydroxy-4-methoxypicolinic acid (35 mg, 0.21 mmol), PyBOP (118 mg, 0.228 mmol) and DIPEA (72 µl, 0.41 mmol) in anhydrous DCM (4.5 mL) was stirred at rt for 3 h. The reaction mixture was evaporated in vacuo, and the residue purified by column chromatography ($SiO_2$, 0-100% EtOAc in PE) to afford the title compound as pale yellow solid (24 mg, 34%).

$^1$H NMR $\delta_H$ (DMSO-d$^6$): 12.26 (s, 1H), 11.04 (s, 1H), 8.43 (s, 1H), 8.21 (d, J=8.9 Hz, 1H), 8.17 (d, J=5.3 Hz, 1H), 8.04 (d, J=8.9 Hz, 1H), 7.75 (d, J=9.0 Hz, 1H), 7.28 (d, J=5.5 Hz, 1H), 7.00 (d, J=8.8 Hz, 1H), 4.45 (q, J=6.9 Hz, 2H), 3.94 (d, J=9.4 Hz, 3H), 1.38 (t, J=7.0 Hz, 3H); LCMS (Method B): 2.00 min, (340.0, $MH^+$).

Examples 2-14

The following Examples were prepared using the general method described in Example 1 from the appropriate intermediate.

| Example No | Compound | $^1$H NMR/LCMS |
| --- | --- | --- |
| 2[a] | N-(2-(4-fluorophenoxy)quinolin-6-yl)-3-hydroxy-4-methoxypicolinamide 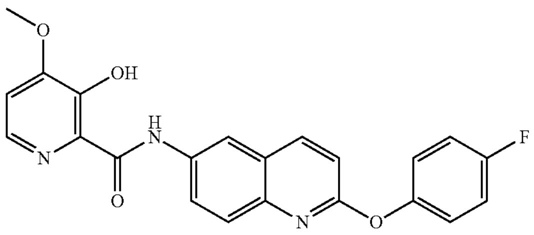 [SMILES: COc1ccnc(C(=O)Nc2ccc3nc(Oc4ccc(F)cc4)ccc3c2)c1O] | 1H NMR $\delta_H$ (DMSO-d$^6$): 12.21 (s, 1H), 11.08 (s, 1H), 8.46 (m, 2H), 8.30-7.87 (m, 2H), 7.63 (d, J = 9.0 Hz, 1H), 7.46-6.94 (m, 6H), 3.93 (s, 3H); LCMS (Method D): 2.72 min, (406.1, $MH^+$). |
| 3 | 3-hydroxy-4-methoxy-N-(2-propoxyquinolin-6-yl)picolinamide 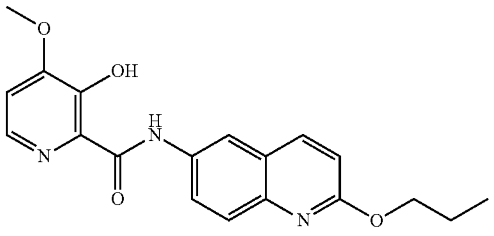 [SMILES: CCCOc1ccc2cc(NC(=O)c3nccc(OC)c3O)ccc2n1] | $^1$H NMR $\delta_H$ (DMSO-d$^6$): 12.26 (s, 1H), 11.03 (s, 1H), 8.43 (dd, J = 7.0, 3.8 Hz, 1H), 8.27-8.12 (m, 1H), 8.12-7.93 (m, 2H), 7.82-7.72 (m, 1H), 7.28 (dt, J = 9.5, 2.9 Hz, 1H), 7.06-6.95 (m, 1H), 4.41-4.27 (m, 2H), 4.04-3.83 (m, 3H), 1.89-1.63 (m, 2H), 1.01 (dt, J = 11.1, 3.6 Hz, 3H); LCMS (Method B): 3.04 min, (354.1, $MH^+$). |
| 4 | N-(2-butoxyquinolin-6-yl)-3-hydroxy-4-methoxypicolinamide 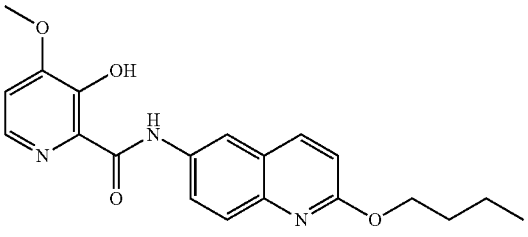 [SMILES: CCCCOc1ccc2cc(NC(=O)c3nccc(OC)c3O)ccc2n1] | $^1$H NMR $\delta_H$ (DMSO-d$^6$): 12.27 (s, 1H), 11.05 (s, 1H), 8.44 (s, 1H), 8.21 (t, J = 9.9 Hz, 2H), 8.04 (s, 1H), 7.76 (d, J = 9.0 Hz, 1H), 7.29 (s, 1H), 7.01 (d, J = 8.8 Hz, 1H), 4.41 (t, J = 6.6 Hz, 2H), 3.94 (s, 3H), 1.84-1.66 (m, 2H), 1.47 (dt, J = 14.5, 7.4 Hz, 2H), 0.97 (t, J = 7.4 Hz, 3H); LCMS (Method B): 3.42 min, (368.1, $MH^+$). |

-continued

| Example No | Compound | $^1H$ NMR/LCMS |
|---|---|---|
| 5 | 3-hydroxy-N-(2-isopropoxyquinolin-6-yl)-4-methoxypicolinamide 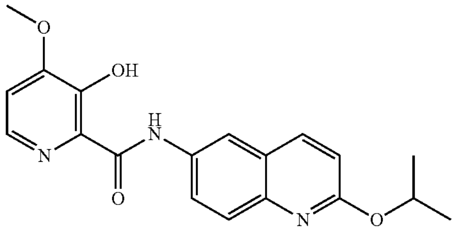 [SMILES: COc1ccnc(C(=O)Nc2ccc3nc(OC(C)C)ccc3c2)c1O] | $^1H$ NMR $\delta_H$ (DMSO-$d^6$): 12.26 (s, 1H), 11.03 (s, 1H), 8.42 (d, J = 2.3 Hz, 1H), 8.29-8.13 (m, 2H), 8.10-7.84 (m, 1H), 7.74 (d, J = 8.9 Hz, 1H), 7.09-6.93 (m, 1H), 6.94 (d, J = 8.8 Hz, 1H), 5.47 (dt, J = 12.3, 6.1 Hz, 1H), 3.94 (d, J = 9.7 Hz, 3H), 1.36 (d, J = 6.2 Hz, 6H); LCMS (Method B): 3.04 min, (354.1, $MH^+$). |
| 6 | 3-hydroxy-4-methoxy-N-(2-((3-methylbutan-2-yl)oxy)quinolin-6-yl)picolinamide 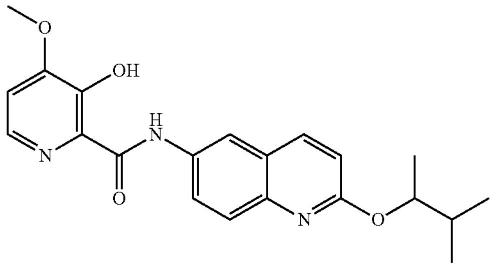 [SMILES: COc1ccnc(C(=O)Nc2ccc3nc(OC(C)C(C)C)ccc3c2)c1O] | $^1H$ NMR $\delta_H$ (DMSO-$d^6$): 12.26 (s, 1H), 11.02 (s, 1H), 8.41 (s, 1H), 8.26-8.16 (m, 2H), 8.03-7.84 (m, 1H), 7.73 (d, J = 9.0 Hz, 1H), 7.29-7.27 (m, 1H), 6.96 (d, J = 8.7 Hz, 1H), 5.30-5.16 (m, 1H), 3.92 (s, 3H), 1.95 (dd, J = 13.2, 6.4 Hz, 1H), 1.28 (d, J = 6.2 Hz, 3H), 1.07-0.81 (m, 6H); LCMS (Method B): 3.69 min, (382.1, $MH^+$). |
| 7 | 3-hydroxy-N-(2-(isopentyloxy)quinolin-6-yl)-4-methoxypicolinamide 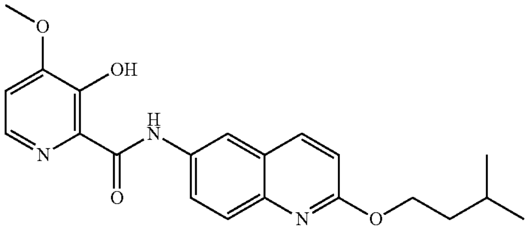 [SMILES: COc1ccnc(C(=O)Nc2ccc3nc(OCCC(C)C)ccc3c2)c1O] | $^1H$ NMR $\delta_H$ (DMSO-$d^6$): 12.26 (s, 1H), 11.04 (s, 1H), 8.43 (s, 1H), 8.30-8.14 (m, 2H), 8.11-7.84 (m, 1H), 7.82-7.62 (m, 1H), 7.28 (d, J = 5.2 Hz, 1H), 7.04 (dt, J = 15.0, 4.6 Hz, 1H), 4.44 (t, J = 6.6 Hz, 2H), 3.94 (d, J = 9.7 Hz, 3H), 1.80 (dt, J = 20.4, 7.0 Hz, 1H), 1.68 (dd, J = 13.2, 6.4 Hz, 2H), 0.96 (d, J = 6.6 Hz, 6H); LCMS (Method D): 2.29 min, (382.2, $MH^+$). |
| 8 | N-(2-((4-fluorophenyl)(methyl)amino)quinolin-6-yl)-3-hydroxy-4-methoxypicolinamide 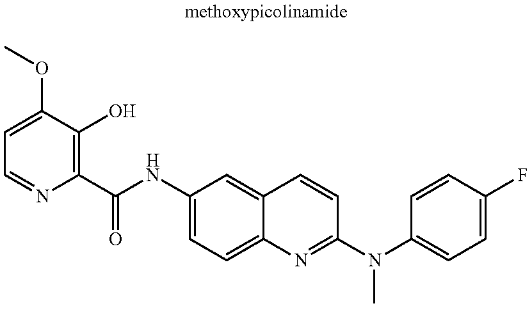 | $^1H$ NMR $\delta_H$ (DMSO-$d^6$): 12.32 (s, 1H), 10.94 (s, 1H), 8.26 (d, J = 2.0 Hz, 1H), 8.16 (d, J = 5.1 Hz, 1H), 8.02-7.87 (m, 2H), 7.65 (d, J = 9.3 Hz, 1H), 7.47-7.37 (m, 2H), 7.37-7.03 (m, 3H), 6.69 (d, J = 9.1 Hz, 1H), 3.93 (d, J = 9.2 Hz, 3H), 3.50 (s, 3H); LCMS (Method B): 2.12 min, (419.1, $MH^+$). |

-continued

| Example No | Compound | $^1$H NMR/LCMS |
|---|---|---|
| 9 | N-(2-((4-fluorophenyl)thio)quinolin-6-yl)-3-hydroxy-4-methoxypicolinamide 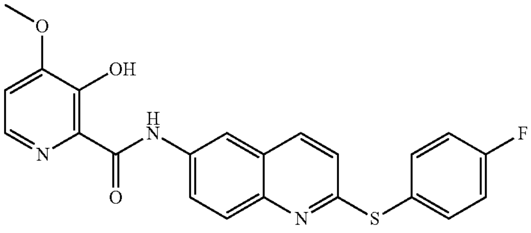 | 1H NMR $\delta_H$ (DMSO-$d^6$): 12.14 (s, 1H), 11.12 (s, 1H), 8.49 (s, 1H), 8.33-8.01 (m, 3H), 7.79 (d, J = 9.1 Hz, 1H), 7.76-7.71 (m, 2H), 7.46-7.21 (m, 3H), 7.08 (d, J = 8.7 Hz, 1H), 3.93 (s, 3H); LCMS (Method B): 3.11 min, (422.0, $MH^+$). |
| 10[a] | N-(2-chloroquinolin-6-yl)-3-hydroxy-4-methoxypicolinamide 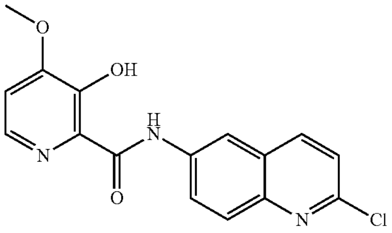 [SMILES: COc1ccnc(C(=O)Nc2ccc3nc(Cl)ccc3c2)c1O] | $^1$H NMR $\delta_H$ (DMSO-$d^6$): 12.10 (s, 1H), 11.22 (s, 1H), 8.64 (s, 1H), 8.45 (d, J = 8.7 Hz, 1H), 8.31-7.86 (m, 3H), 7.77-7.52 (m, 1H), 7.35-7.05 (m, 1H), 3.93 (s, 3H); LCMS (Method B): 2.17 min, $MH^+$). |
| 11 | N-(2-(sec-butoxy)quinolin-6-yl)-3-hydroxy-4-methoxypicolinamide 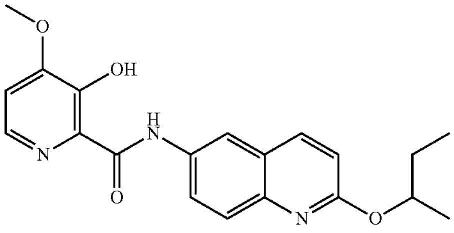 [SMILES: CCC(C)Oc1ccc2cc(NC(=O)c3nccc(OC)c3O)ccc2n1] | $^1$H NMR $\delta_H$ (DMSO-$d^6$): 12.26 (s, 1H), 11.02 (s, 1H), 8.41 (d, J = 2.1 Hz, 1H), 8.29-8.13 (m, 2H), 8.07-7.84 (m, 1H), 7.77-7.62 (m, 1H), 7.31-7.05 (m, 1H), 6.96 (d, J = 8.8 Hz, 1H), 5.38-5.26 (m, 1H), 3.94 (d, J = 9.9 Hz, 3H), 1.71 (m, 2H), 1.33 (d, J = 6.2 Hz, 3H), 0.95 (t, J = 7.4 Hz, 3H); LCMS (Method B): 3.37 min, (368.1, $MH^+$). |
| 12 | 3-hydroxy-N-(2-isobutoxyquinolin-6-yl)-4-methoxypicolinamide 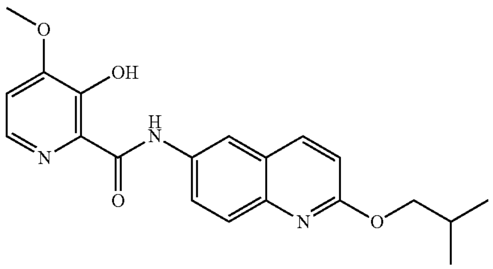 [SMILES: COc1ccnc(C(=O)Nc2ccc3nc(OCC(C)C)ccc3c2)c1O] | $^1$H NMR $\delta_H$ (DMSO-$d^6$): 12.26 (s, 1H), 11.04 (s, 1H), 8.43 (s, 1H), 8.19 (m, 2H), 8.04 (d, J = 10.2 Hz, 1H), 7.75 (m, 1H), 7.28 (d, J = 5.2 Hz, 1H), 7.02 (d, J = 8.9 Hz, 1H), 4.18 (d, J = 6.7 Hz, 2H), 3.93 (s, 3H), 2.10 (dt, J = 13.3, 6.5 Hz, 1H), 1.02 (d, J = 6.7 Hz, 6H); LCMS (Method B): 3.40 min, (368.1, $MH^+$). |

-continued

| Example No | Compound | $^1$H NMR/LCMS |
|---|---|---|
| 13 | N-(3-benzylquinolin-6-yl)-3-hydroxy-4-methoxypicolinamide 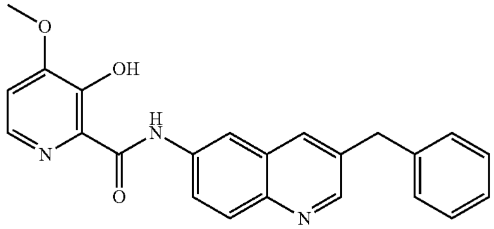 [SMILES: COc1ccnc(C(=O)Nc2ccc3ncc(Cc4ccccc4)cc3c2)c1O] | $^1$H NMR $\delta_H$ (CDCl3): 11.68 (s, 1H), 10.03 (s, 1H), 8.88-8.77 (m, 3H), 8.59-8.54 (m, 1H), 8.00-7.98 (m, 1H), 7.40-7.34 (m, 3H), 7.25-7.22 (m, 3H), 7.00-6.95 (m, 1H), 4.31 (s, 2H), 4.01 (s, 3H); LCMS (Method B): 2.50 min, (386.1, MH$^+$). |
| 14 | N-(6-benzylquinolin-2-yl)-3-hydroxy-4-methoxypicolinamide 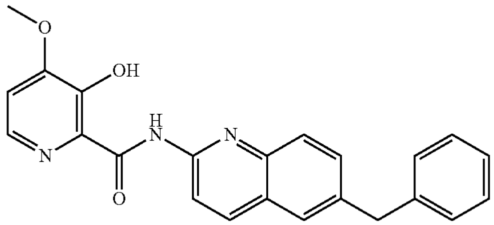 [SMILES: COc1ccnc(C(=O)Nc2ccc3cc(Cc4ccccc4)ccc3n2)c1O] | $^1$H NMR $\delta_H$ (DMSO-d$^6$): 14.12 (s, 1H), 11.60 (s, 1H), 8.58-8.27 (m, 3H), 7.90-7.69 (m, 2H), 7.65-7.56 (m, 1H), 7.31 (d, J = 3.5 Hz, 4H), 7.26-7.15 (m, 1H), 7.15-6.97 (m, 1H), 4.14 (s, 2H), 3.95 (s, 3H); LCMS (Method B): 2.94 min, (386.1, MH$^+$). |

[a]Product was filtered from reaction mixture, no chromatography needed.

Example 15: N-(6-bromoquinolin-2-yl)-3-hydroxy-4-methoxypicolinamide

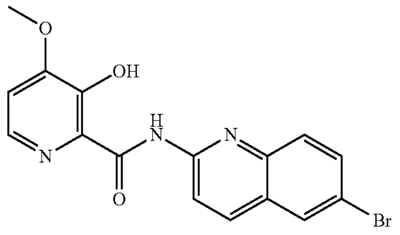 [SMILES: COc1ccnc(C(=O)Nc2ccc3cc(Br)ccc3n2)c1O]

6-Bromoquinolin-2-amine (69 mg, 0.30 mmol) was taken up in DMF (4 mL) and 8-methoxy-2,2-dimethyl-4H-[1,3]dioxino[5,4-b]pyridin-4-one 2,2,2-trifluoroacetate (250 mg, 0.77 mmol) added. Sodium bis(trimethylsilyl)amide solution (0.8 mL, 1.5 mmol) was added and the reaction stirred at 60° C. for 24 h. The reaction mixture was allowed to cool to rt and then water (5 mL) was added. A precipitate formed which was filtered, and the solid was slurried in ethanol, filtered and dried under vacuum to yield the title compound as a light brown solid (14.3 mg, 16%).

$^1$H NMR $\delta_H$ (400 MHz, DMSO-d$^6$) 15.80 (s, 1H), 8.66 (d, J=9.7 Hz, 1H), 8.25 (d, J=6.4 Hz, 1H), 8.13 (s, 1H), 7.81-7.68 (m, 2H), 7.50-7.41 (m, 1H), 6.66-6.52 (m, 1H), 3.72 (s, 2H) (NH or OH not seen); LCMS (Method B): 2.50 min, (374.0/375.9, MH$^+$).

Example 16: 3-hydroxy-4-methoxy-N-(6-phenylquinolin-2-yl)picolinamide

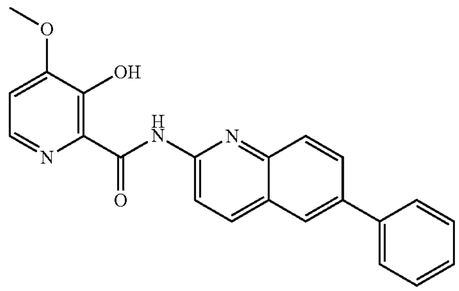 [SMILES: COc1ccnc(C(=O)Nc2ccc3cc(-c4ccccc4)ccc3n2)c1O]

Following the procedure for Example 15, the title compound was obtained as a light brown solid (30 mg, 17%).

$^1$H NMR $\delta_H$ (400 MHz, DMSO-d$^6$) 15.78 (s, 1H), 8.67 (d, J=9.0 Hz, 1H), 8.33 (d, J=9.0 Hz, 1H), 8.15 (s, 1H), 8.00 (d, J=2.1 Hz, 1H), 7.83 (dd, J=13.6, 8.0 Hz, 3H), 7.51 (t, J=7.7 Hz, 2H), 7.44 (d, J=4.6 Hz, 1H), 7.40 (d, J=7.4 Hz, 1H), 6.61 (d, J=4.7 Hz, 1H), 3.72 (s, 3H);

LCMS (Method B): 2.82 min, (372.1, MH$^+$).

Example 17: 2-((6-bromoquinolin-2-yl)carbamoyl)-4-methoxypyridin-3-yl acetate

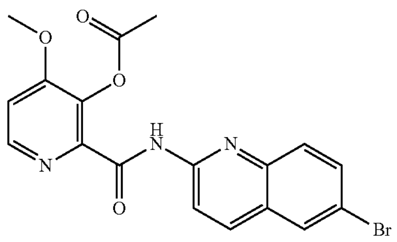 [SMILES: COc1ccnc(C(=O)Nc2ccc3cc(Br)ccc3n2)c1OC(C)=O]

Example 15 (82 mg, 0.22 mmol) was dissolved in pyridine (1 mL) and acetic anhydride (0.4 mL, 4.4 mmol) and stirred for 1 h. The solvent was evaporated in vacuo and the residue was azeotroped sequentially with heptane, DCM and $Et_2O$. The crude residue was purified by column chromatography ($SiO_2$, 0-100% EtOAc in PE) to afford the title compound as an orange solid (8 mg, 9%).

$^1$H NMR $\delta_H$ (400 MHz, DMSO-d$^6$) 10.85 (s, 1H), 8.56 (d, J=5.5 Hz, 1H), 8.49-8.38 (m, 2H), 8.27 (f, 1H), 7.92-7.78 (m, 1H), 7.54 (d, J=5.5 Hz, 2H), 3.97 (s, 3H), 2.36 (z, 3H).

Examples 18-19

The following Examples were prepared using the general method described in Example 17 from the appropriate intermediate.

| Example No | Compound | $^1$H NMR/LCMS |
|---|---|---|
| 18 | 4-methoxy-2-((6-phenylquinolin-2-yl)carbamoyl)pyridin-3-yl acetate 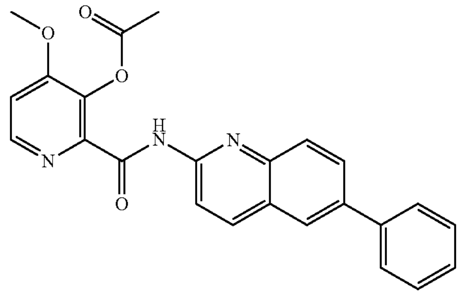 [SMILES: COc1ccnc(C(=O)Nc2ccc3cc(-c4ccccc4)ccc3n2)c1OC(C)=O] | $^1$H NMR $\delta_H$ (400 MHz, DMSO-d$^6$) δ 10.84 (s, 1H), 8.57 (d, J = 5.5 Hz, 1H), 8.53 (d, J = 9.0 Hz, 1H), 8.42 (d, J = 9.0 Hz, 1H), 8.28 (d, J = 2.0 Hz, 1H), 8.10 (dd, J = 8.8, 2.0 Hz, 1H), 7.95 (d, J = 8.8 Hz, 1H), 7.84 (d, J = 8.7 Hz, 2H), 7.54 (t, J = 7.2 Hz, 3H), 7.43 (t, J = 7.3 Hz, 1H), 3.97 (s, 3H), 2.38 (s, 3H); LCMS (Method B): 3.73 min, (414.1, MH$^+$). |
| 19 | 2-((2-(4-fluorophenoxy)quinolin-6-yl)carbamoyl)-4-methoxypyridin-3-yl acetate 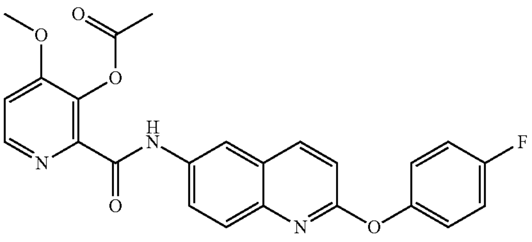 [SMILES: COc1ccnc(C(=O)Nc2ccc3nc(Oc4ccc(F)cc4)ccc3c2)c1OC(C)=O] | $^1$H NMR $\delta_H$ (DMSO-d$^6$): 10.79 (s, 1H), 8.51 (dd, J = 7.2, 3.9 Hz, 2H), 8.39 (d, J = 8.9 Hz, 1H), 7.97 (dd, J = 9.1, 2.3 Hz, 1H), 7.60 (d, J = 9.1 Hz, 1H), 7.47 (d, J = 5.5 Hz, 1H), 7.33-7.22 (m, 5H), 3.94 (s, 3H), 2.31 (s, 3H); LCMS (Method B): 3.31 min, (448.1, MH$^+$). |

Examples 20-28

The following Examples were prepared using the general method described in Example 1 from the appropriate intermediate.

| Example No | Compound | $^1$H NMR/LCMS |
|---|---|---|
| 20 | N-(2-(2-chlorophenoxy) quinolin-6-yl)-3-hydroxy-4-methoxypicolinamide 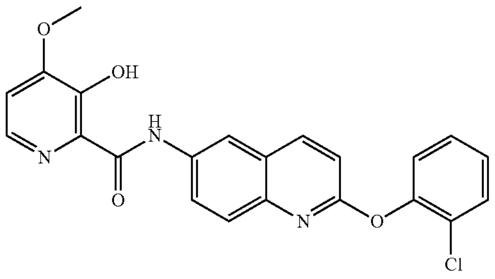 [SMILES: COc1ccnc(C(=O)Nc2ccc3nc(Oc4ccccc4Cl)ccc3c2)c1O] | $^1$H NMR $\delta_H$ (DMSO-d$^6$): 12.21 (br s, 1H), 11.10 (br s, 1H), 8.50 (br s, 1H), 8.44 (d, J = 8.8 Hz, 1H), 8.15 (br s, 1H), 8.02 (br s, 1H), 7.67-7.57 (m, 2H), 7.52-7.41 (m, 2H), 7.40-7.31 (m, 2H), 7.26 (br s, 1H), 3.94 (s, 3H); LCMS (Method B): 3.13 min, (422.1, MH$^+$). |
| 21 | N-(2-(4-fluorophenoxy)-4-pentylquinolin-6-yl)-3-hydroxy-4-methoxypicolinamide 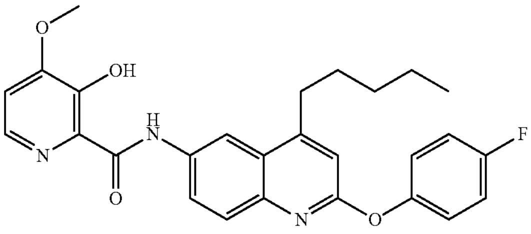 [SMILES: CCCCCc1cc(Oc2ccc(F)cc2)nc2ccc(NC(=O)c3nccc(OC)c3O)cc12] | $^1$H NMR $\delta_H$ (DMSO-d$^6$): 12.24 (br s, 1H), 11.13 (br s, 1H), 8.60 (d, J = 2.0 Hz, 1H), 8.14 (v br s, 2H), 7.63 (d, J = 9.0 Hz, 1H), 7.34-7.18 (m, 5H), 7.14 (s, 1H), 3.94 (s, 3H), 3.09-2.99 (m, 2H), 1.83-1.69 (m, 2H), 1.49-1.33 (m, 4H), 0.92 (t, J = 7.0 Hz, 3H); LCMS (Method B): 4.30 min, (476.2, MH$^+$). |
| 22 | 3-hydroxy-4-methoxy-N-(2-(2-methoxyphenoxy)quinolin-6-yl)picolinamide 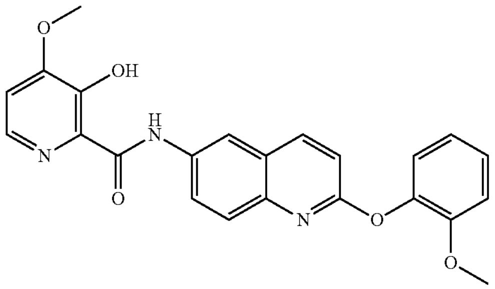 [SMILES: COc1ccccc1Oc1ccc2cc(NC(=O)c3nccc(OC)c3O)ccc2n1] | $^1$H NMR $\delta_H$ (DMSO-d$^6$): 12.23 (br s, 1H), 11.07 (br s, 1H), 8.48 (br m, 1H), 8.36 (d, J = 8.8 Hz, 1H), 8.18 (br m, 1H), 8.04 (br m, 1H), 7.59 (d, J = 9.0 Hz, 1H), 7.3-7.16 (m, 5H), 7.06-6.99 (m, 1H), 3.94 (s, 3H), 3.69 (s, 3H); LCMS (Method A): 2.48 min, (418.1, MH$^+$). |
| 23 | N-(2((2-chlorophenyl)(methyl) amino)quinolin-6-yl)-3-hydroxy-4-methoxypicolinamide 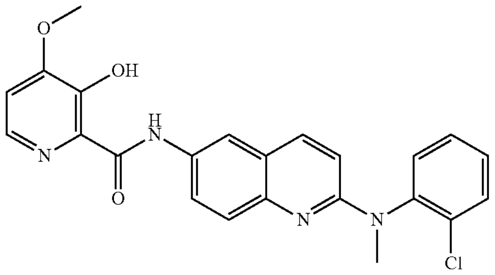 [SMILES: COc1ccnc(C(=O)Nc2ccc3nc(N(C)c4ccccc4Cl)ccc3c2)c1O] | $^1$H NMR $\delta_H$ (DMSO-d$^6$): 12.33 (s, 1H), 10.95 (s, 1H), 8.27 (br s, 1H), 8.16 (br s, 1H), 7.98 (br s, 1H), 7.93 (d, J = 9.1 Hz, 1H), 7.73-7.64 (m, 2H), 7.59-7.42 (m, 3H), 7.27 (br s, 1H), 6.38 (d, J = 9.1 Hz, 1H), 3.93 (s, 3H), 3.46 (s, 3H); LCMS (Method A): 3.13 min, (435.1, MH$^+$). |

-continued

| Example No | Compound | $^1$H NMR/LCMS |
| --- | --- | --- |
| 24 | N-(2-(2-chlorophenoxy)-5-propoxyquinolin-6-yl)-3-hydroxy-4-methoxypicolinamide 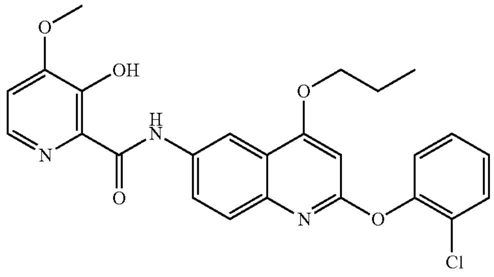 [SMILES: CCCOc1cc(Oc2ccccc2Cl)nc2ccc(NC(=O)c3nccc(OC)c3O)cc12] | $^1$H NMR $\delta_H$ (DMSO-$d^6$): 11.94 (s, 1H), 10.65 (s, 1H), 9.17 (s, 1H), 8.31 (d, J = 9.0 Hz, 1H), 8.17 (d, J = 5.2 Hz, 1H), 7.69 (dd, J = 7.9, 1.4 Hz, 1H), 7.53-7.42 (m, 1H), 7.38-7.30 (m, 3H), 7.28 (d, J = 5.3 Hz, 1H), 6.97 (dd, J = 9.0, 2.0 Hz, 1H), 4.26 (t, J = 7.2 Hz, 2H), 3.93 (s, 3H), 1.82-1.69 (m, 2H), 0.90 (t, J = 7.4 Hz, 3H); LCMS (Method A): 3.08 min, (480.1, $MH^+$). |
| 25 | N-(2-((2-chloropyridin-3-yl)(methyl)amino)quinolin-6-yl)-3-hydroxy-4-methoxypicolinamide 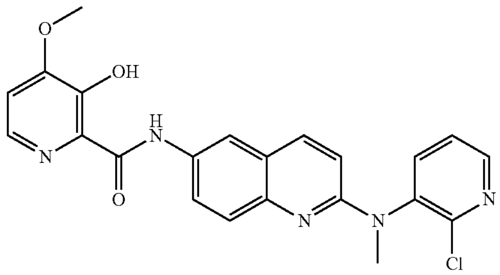 [SMILES: COc1ccnc(C(=O)Nc2ccc3nc(N(C)c4cccnc4Cl)ccc3c2)c1O] | $^1$H NMR $\delta_H$ (DMSO-$d^6$): 12.32 (br s, 1H), 10.97 (br s, 1H), 8.47 (dd, J = 4.7, 1.8 Hz, 1H), 8.29 (br m, 1H), 8.16 (br m, 1H), 8.07 (dd, J = 7.8, 1.8 Hz, 1H), 8.04-7.95 (m, 2H), 7.66 (d, J = 9.0 Hz, 1H), 7.62 (dd, J = 7.8, 4.7 Hz, 1H), 7.27 (br m, 1H), 6.55 (d, J = 9.0 Hz, 1H), 3.93 (s, 3H), 3.47 (s, 3H); LCMS (Method A): 1.15 min, (436.1, $MH^+$). |
| 26 | N-(2-((2-chlorophenyl)thio)quinolin-6-yl)-3-hydroxy-4-methoxypicolinamide 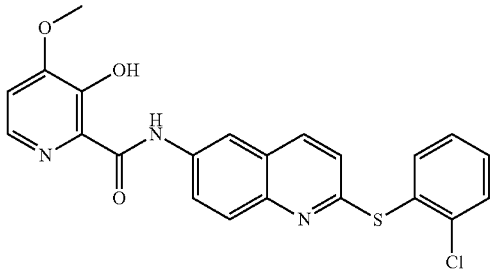 | $^1$H NMR $\delta_H$ (DMSO-$d^6$): 12.15 (br s, 1H), 11.13 (br s, 1H), 8.48 (br m, 1H), 8.24 (d, J = 8.6 Hz, 1H), 8.12 (br m, 2H), 7.84-7.77 (m, 2H), 7.73 (dd, J = 8.0, 1.3 Hz, 1H), 7.62-7.53 (m, 1H), 7.53-7.46 (m, 1H), 7.27 (br m, 1H), 7.09 (d, J = 8.7 Hz, 1H), 3.94 (s, 3H); LCMS (Method A): 3.06 min, (438.0, $MH^+$). |
| 27 | N-(2-((2-chloropyridin-3-yl)oxy)quinolin-6-yl)-3-hydroxy-4-methoxypicolinamide 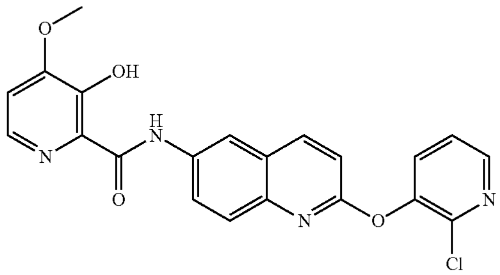 | $^1$H NMR $\delta_H$ (DMSO-$d^6$): 12.20 (br s, 1H), 11.11 (br s, 1H), 8.56 (br m, 1H), 8.49 (d, J = 8.7 Hz, 1H), 8.39 (dd, J = 4.7, 1.7 Hz, 1H), 8.19 (br m, 1H), 8.07 (br m, 1H), 7.99 (dd, J = 8.0, 1.7 Hz, 1H), 7.66-7.57 (m, 2H), 7.42 (d, J = 8.8 Hz, 1H), 7.27 (br m, 1H), 3.94 (s, 3H); LCMS (Method A): 0.99 min, (423.0, $MH^+$). |

-continued

| Example No | Compound | $^1$H NMR/LCMS |
|---|---|---|
| 28 | N-(2-((2-chloropyridin-3-yl)thio)quinolin-6-yl)-3-hydroxy-4-methoxypicolinamide<br>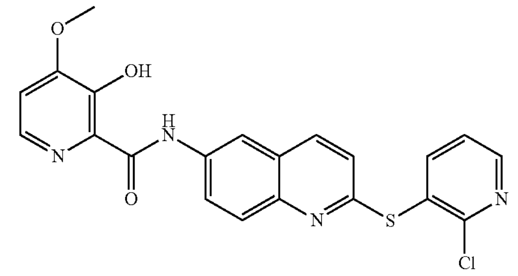 | $^1$H NMR $\delta_H$ (DMSO-d$^6$): 12.13 (s, 1H), 11.19 (s, 1H), 8.57 (br m, 1H), 8.43-8.39 (m, 1H), 8.33 (d, J = 8.7 Hz, 1H), 8.17 (br m, 2H), 8.05 (dd, J = 8.0, 1.4 Hz, 1H), 7.94 (d, J = 9.0 Hz, 1H), 7.57 (d, J = 8.6 Hz, 1H), 7.38 (dd, J = 8.0, 4.7 Hz, 1H), 7.26 (br m, 1H), 3.94 (s, 3H); LCMS (Method A): 1.90 min, (439.0, MH$^+$). |

Examples 29-36

The following Examples were prepared using the general method described in Example 17 from the appropriate intermediate.

| Example No | Compound | $^1$H NMR/LCMS |
|---|---|---|
| 29 | 2-((2-((4-fluorophenyl)thio)quinolin-6-yl)carbamoyl)-4-methoxypyridin-3-yl acetate<br>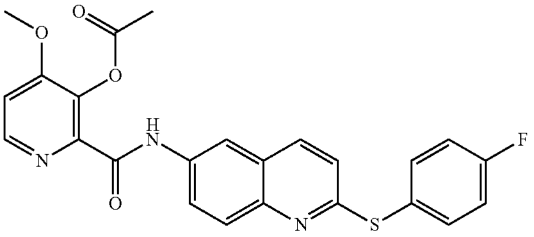 | $^1$H NMR $\delta_H$ (DMSO-d$^6$): 10.85 (s, 1H), 8.53 (d, J = 5.5 Hz, 1H), 8.49 (d, J = 2.3 Hz, 1H), 8.20 (d, J = 8.6 Hz, 1H), 8.03 (dd, J = 9.1, 2.4 Hz, 1H), 7.81-7.70 (m, 3H), 7.48 (d, J = 5.6 Hz, 1H), 7.43-7.34 (m, 2H), 7.06 (d, J = 8.7 Hz, 1H), 3.95 (s, 3H), 2.32 (s, 3H); LCMS (Method B): 3.47 min, (464.1, MH$^+$). |
| 30 | 2-((2-(2-chlorophenoxy)quinolin-6-yl)carbamoyl)-4-methoxypyridin-3-yl acetate<br>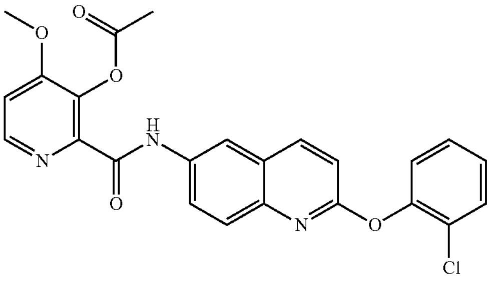 | $^1$H NMR $\delta_H$ (DMSO-d$^6$): 10.80 (s, 1H), 8.54-8.49 (m, 2H), 8.43 (d, J = 8.8 Hz, 1H), 7.97 (dd, J = 9.1, 2.4 Hz, 1H), 7.63 (dd, J = 8.0, 1.4 Hz, 1H), 7.58 (d, J = 9.1 Hz, 1H), 7.50-7.41 (m, 3H), 7.38-7.31 (m, 2H), 3.95 (s, 3H), 2.32 (s, 3H); LCMS (Method B): 3.43 min, (464.1, MH$^+$). |

-continued

| Example No | Compound | $^1$H NMR/LCMS |
|---|---|---|
| 31 | 2-((2-(4-fluorophenoxy)-4-pentylquinolin-6-yl)carbamoyl)-4-methoxypyridin-3-yl acetate 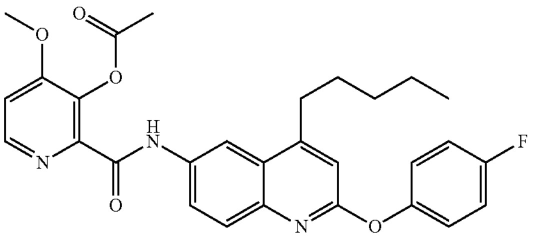 [SMILES: CCCCCc1cc(Oc2ccc(F)cc2)nc2ccc(NC(=O)c3nccc(OC)c3OC(C)=O)cc12] | $^1$H NMR $\delta_H$ (DMSO-$d^6$): 10.83 (s, 1H), 8.56 (d, J = 2.2 Hz, 1H), 8.53 (d, J = 5.5 Hz, 1H), 8.14 (dd, J = 9.1, 2.2 Hz, 1H), 7.60 (d, J = 9.0 Hz, 1H), 7.48 (d, J = 5.6 Hz, 1H), 7.31-7.26 (m, 4H), 7.12 (s, 1H), 3.95 (s, 3H), 3.07-2.98 (m, 2H), 2.31 (s, 3H), 1.82-1.70 (m, 2H), 1.51-1.35 (m, 4H), 0.92 (t, J = 7.0 Hz, 3H); LCMS (Method B): 4.21 min, (518.2, $MH^+$). |
| 32 | 2-((2-((2-chlorophenyl)(methyl)amino)quinolin-6-yl)carbamoyl)-4-methoxypyridin-3-yl acetate 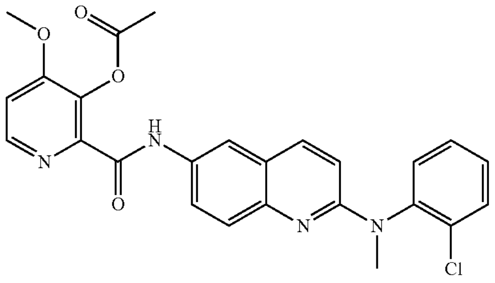 [SMILES: COc1ccnc(C(=O)Nc2ccc3nc(N(C)c4ccccc4Cl)ccc3c2)c1OC(C)=O] | $^1$H NMR $\delta_H$ (DMSO-$d^6$): 10.65 (s, 1H), 8.52 (d, J = 5.5 Hz, 1H), 8.27 (d, J = 2.2 Hz, 1H), 7.96-7.86 (m, 2H), 7.73-7.62 (m, 2H), 7.57-7.49 (m, 2H), 7.49-7.41 (m, 2H), 6.36 (d, J = 9.1 Hz, 1H), 3.95 (s, 3H), 3.46 (s, 3H), 2.31 (s, 3H); LCMS (Method B): 3.16 min, (477.1, $MH^+$). |
| 33 | 2-((2-((2-chlorophenyl)thio)quinolin-6-yl)carbamoyl)-4-methoxypyridin-3-yl acetate 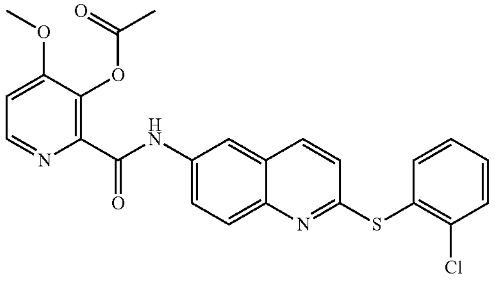 [SMILES: COc1ccnc(C(=O)Nc2ccc3nc(Sc4ccccc4Cl)ccc3c2)c1OC(C)=O] | $^1$H NMR $\delta_H$ (DMSO-$d^6$): 10.86 (s, 1H), 8.53 (d, J = 5.5 Hz, 1H), 8.50 (d, J = 2.3 Hz, 1H), 8.23 (d, J = 8.5 Hz, 1H), 8.03 (dd, J = 9.1, 2.4 Hz, 1H), 7.83-7.75 (m, 2H), 7.73 (dd, J = 8.0, 1.3 Hz, 1H), 7.60-7.54 (m, 1H), 7.52-7.45 (m, 2H), 7.07 (d, J = 8.7 Hz, 1H), 3.95 (s, 3H), 2.32 (s, 3H); LCMS (Method B): 3.55 min, (480.1, $MH^+$). |
| 34 | 2-((2-((2-chloropyridin-3-yl)(methyl)amino)quinolin-6-yl)carbamoyl)-4-methoxypyridin-3-yl acetate 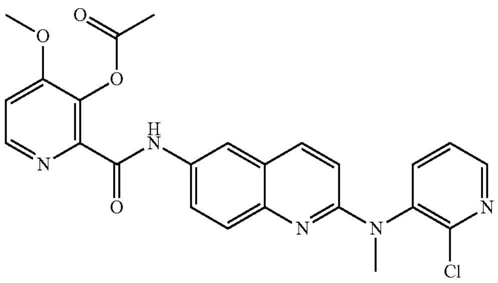 [SMILES: COc1ccnc(C(=O)Nc2ccc3nc(N(C)c4cccnc4Cl)ccc3c2)c1OC(C)=O] | $^1$H NMR $\delta_H$ (DMSO-$d^6$): 10.67 (s, 1H), 8.52 (d, J = 5.5 Hz, 1H), 8.46 (dd, J = 4.7, 1.8 Hz, 1H), 8.30 (d, J = 2.3 Hz, 1H), 8.06 (dd, J = 7.8, 1.8 Hz, 1H), 7.99 (d, J = 9.1 Hz, 1H), 7.91 (dd, J = 9.0, 2.4 Hz, 1H), 7.66-7.58 (m, 2H), 7.46 (d, J = 5.6 Hz 1H) 6.53 (d J = 9.1 Hz, 1H), 3.95 (s, 3H), 3.46 (s, 3H), 2.31 (s, 3H); LCMS (Method B): 3.37 min, (478.1, $MH^+$). |

-continued

| Example No | Compound | $^1$H NMR/LCMS |
| --- | --- | --- |
| 35 | 2-((2-((2-chloropyridin-3-yl)thio)quinolin-6-yl)carbamoyl)-4-methoxypyridin-3-yl acetate 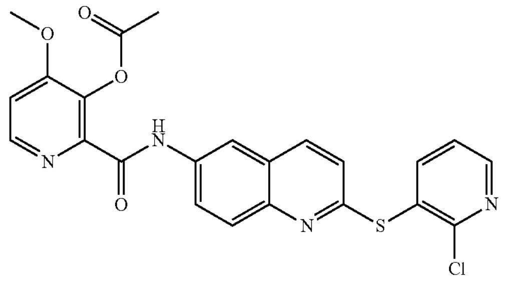 [SMILES: COc1ccnc(C(=O)Nc2ccc3nc(Sc4cccnc4Cl)ccc3c2)c1OC(C)=O] | $^1$H NMR $\delta_H$ (DMSO-$d^6$): 10.92 (s, 1H), 8.60-8.57 (m, 1H), 8.54 (d, J = 5.5 Hz, 1H), 8.41 (dd, J = 4.7, 1.5 Hz, 1H), 8.33 (d, J = 8.5 Hz, 1H), 8.08 (dd, J = 9.1, 2.3 Hz, 1H), 8.04 (dd, J = 8.0, 1.5 Hz, 1H), 7.91 (d, J = 9.1 Hz, 1H), 7.55 (d, J = 8.6 Hz, 1H), 7.49 (d, J = 5.6 Hz, 1H), 7.41-7.35 (m, 1H), 3.96 (s, 3H), 2.33 (s, 3H); LCMS (Method B): 3.69 min, (481.0, $MH^+$). |
| 36 | 2-((2-((2-chloropyridin-3-yl)oxy)quinolin-6-yl)carbamoyl)-4-methoxypyridin-3-yl acetate 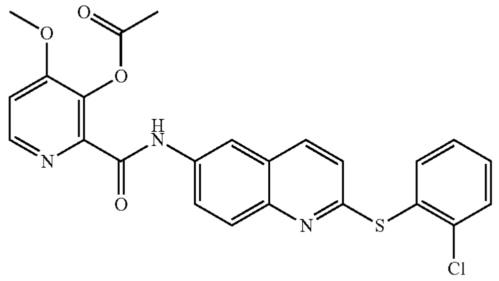 | $^1$H NMR $\delta_H$ (DMSO-$d^6$): 10.82 (s, 1H), 8.54 (d, J = 2.3 Hz, 1H), 8.52 (d, J = 5.5 Hz, 1H), 8.48 (d, J = 8.8 Hz, 1H), 8.39 (dd, J = 4.7, 1.6 Hz, 1H), 8.01-7.95 (m, 2H), 7.63-7.57 (m, 2H), 7.48 (d, J = 5.6 Hz, 1H), 7.40 (d, J = 8.8 Hz, 1H), 3.95 (s, 3H), 2.32 (s, 3H); LCMS (Method B): 3.55 min, (465.1, $MH^+$). |

Example 37: 3-(2-((4-fluorophenyl)thio)quinolin-6-yl)-8-methoxy-2-thioxo-2,3-dihydro-4H-pyrido[2,3-e][1,3]oxazin-4-one

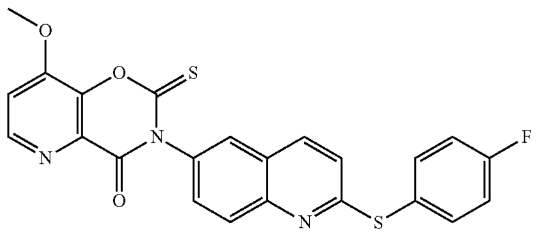 [SMILES: COc1ccnc2c(=O)n(-c3ccc4nc(Sc5ccc(F)cc5)ccc4c3)c(=S)oc12]

A solution of Example 9 (30 mg, 0.071 mmol) in anhydrous DCM (1 mL) was treated with thiophosgene (10.9 μL, 0.142 mmol) followed by pyridine (0.086 mL, 1.07 mmol), and the reaction was stirred at rt for 30 min. The reaction mixture was purified by column chromatography ($SiO_2$, 0-100% EtOAc in PE) and the title compound was isolated as a pale yellow solid (5.9 mg, 18%).

$^1$H NMR $\delta_H$ (DMSO-d): 8.61 (d, J=5.4 Hz, 1H), 8.30 (d, J=8.6 Hz, 1H), 7.95 (d, J=2.2 Hz, 1H), 7.92 (d, J=8.9 Hz, 1H), 7.80-7.71 (m, 3H), 7.61 (d, J=5.5 Hz, 1H), 7.45-7.37 (m, 2H), 7.18 (d, J=8.7 Hz, 1H), 4.10 (s, 3H); LCMS (Method B): 3.19 min, (464.1, $MH^+$).

Examples 38-46

The following Examples were prepared using the general method described in Example 37 from the appropriate intermediate.

| Example No | Compound | $^1$H NMR/LCMS |
|---|---|---|
| 38 | 3-(2-(sec-butoxy)quinolin-6-yl)-8-methoxy-2-thioxo-2,3-dihydro-4H-pyrido[2,3-e][1,3]oxazin-4-one 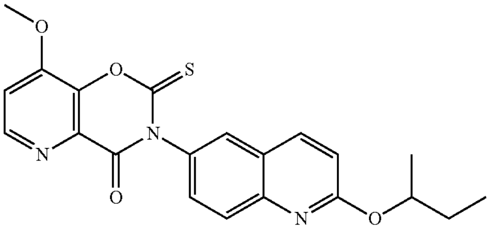 [SMILES: CCC(C)Oc1ccc2cc(-n3c(=S)oc4c(OC)ccnc4c3=O)ccc2n1] | $^1$H NMR $\delta_H$ (DMSO-$d_6$): 8.61 (d, J = 5.4 Hz, 1H), 8.29 (d, J = 8.9 Hz, 1H), 7.89 (d, J = 2.2 Hz, 1H), 7.86 (d, J = 8.9 Hz, 1H), 7.65 (dd, J = 8.8, 2.3 Hz, 1H), 7.61 (d, J = 5.5 Hz, 1H), 7.03 (d, J = 8.9 Hz, 1H), 5.43-5.34 (m, 1H), 4.10 (s, 3H), 1.80-1.65 (m, 2H), 1.36 (d, J = 6.2 Hz, 3H), 0.97 (t, J = 7.4 Hz, 3H); LCMS (Method B): 3.31 min, (410.1, $MH^+$). |
| 39 | 8-methoxy-3-(2-((3-methylbutan-2-yl)oxy)quinolin-6-yl)-2-thioxo-2,3-dihydro-4H-pyrido[2,3-e][1,3]oxazin-4-one 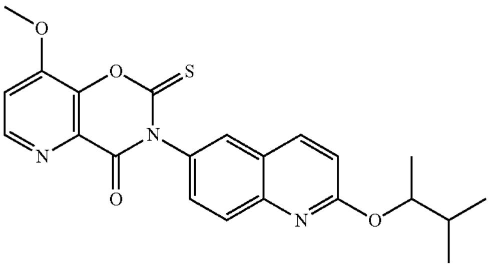 [SMILES: COc1ccnc2c(=O)n(-c3ccc4nc(OC(C)C(C)C)ccc4c3)c(=S)oc12] | $^1$H NMR $\delta_H$ (DMSO-$d^6$): 8.61 (d, J = 5.4 Hz, 1H), 8.29 (d, J = 8.9 Hz, 1H), 7.89 (d, J = 2.3 Hz, 1H), 7.86 (d, J = 8.9 Hz, 1H), 7.65 (dd, J = 8.8, 2.3 Hz, 1H), 7.61 (d, J = 5.5 Hz, 1H), 7.04 (d, J = 8.8 Hz, 1H), 5.35-5.24 (m, 1H), 4.10 (s, 3H), 2.05-1.91 (m, 1H), 1.32 (d, J = 6.3 Hz, 3H), 1.05-0.95 (m, 6H); LCMS (Method B): 3.51 min, (424.1, $MH^+$). |
| 40 | 3-(2-(2-chlorophenoxy)quinolin-6-yl)-8-methoxy-2-thioxo-2,3-dihydro-4H-pyrido[2,3-e][1,3]oxazin-4-one 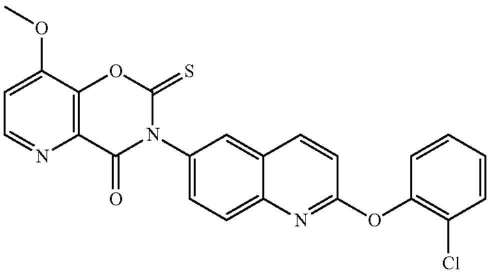 | $^1$H NMR $\delta_H$ (DMSO-$d^6$): 8.61 (d, J = 5.4 Hz, 1H), 8.54 (d, J = 8.9 Hz, 1H), 8.00 (d, J = 2.1 Hz, 1H), 7.73 (d, J = 8.9 Hz, 1H), 7.68 - 7.63 (m, 2H), 7.61 (d, J = 5.4 Hz, 1H), 7.51-7.47 (m, 2H), 7.43 (d, J = 8.9 Hz, 1H), 7.40-7.34 (m, 1H), 4.10 (s, 3H); LCMS (Method B): 3.16 min, (464.0, $MH^+$). |
| 41 | 8-methoxy-3-(2-(2-methoxyphenoxy)quinolin-6-yl)-2-thioxo-2,3-dihydro-4H-pyrido[2,3-e][1,3]oxazin-4-one 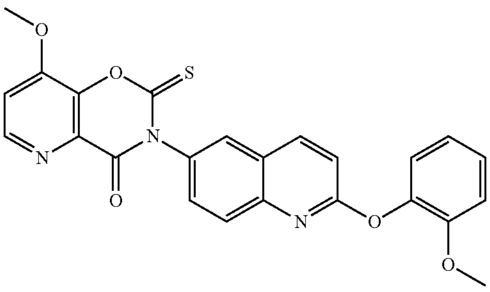 [SMILES: COc1ccccc1Oc1ccc2cc(-n3c(=S)oc4c(OC)ccnc4c3=O)ccc2n1] | 1H NMR $\delta_H$ (DMSO-$d^6$): 8.61 (d, J = 5.4 Hz, 1H), 8.45 (d, J = 8.7 Hz, 1H), 7.96 (d, J = 2.3 Hz, 1H), 7.72 (d, J = 8.9 Hz, 1H), 7.65-7.58 (m, 2H), 7.34-7.25 (m, 3H), 7.21 (dd, J = 8.2, 1.5 Hz, 1H), 7.09-7.02 (m, 1H), 4.10 (s, 3H), 3.71 (s, 3H); LCMS (Method B): 2.91 min, (460.1, $MH^+$). |

-continued

| Example No | Compound | $^1$H NMR/LCMS |
|---|---|---|
| 42 | 3-(2-((2-chlorophenyl)(methyl) amino)quinolin-6-yl)-8-methoxy-2-thioxo-2,3-dihydro-4H-pyrido[2,3-e][1,3]oxazin-4-one 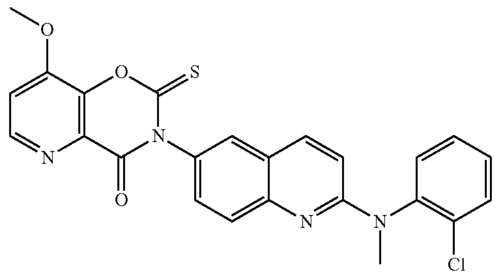 [SMILES: COc1ccnc2c(=O)n(-c3ccc4nc(N(C)c5ccccc5Cl)ccc4c3)c(=S)oc12] | $^1$H NMR $\delta_H$ (DMSO-d$^6$): 8.61 (d, J = 5.4 Hz, 1H), 7.98 (d, J = 9.1 Hz, 1H), 7.77 (d, J = 8.9 Hz, 1H), 7.74-7.69 (m, 2H), 7.63-7.44 (m, 5H), 6.42 (d, J = 9.1 Hz, 1H), 4.09 (s, 3H), 3.50 (s, 3H); LCMS (Method B): 3.16 min, (477.1, MH$^+$). |
| 43 | 3-(2-((2-chlorophenyl)thio) quinolin-6-yl)-8-methoxy-2-thioxo-2,3-dihydro-4H-pyrido[2,3-e][1,3]oxazin-4-one 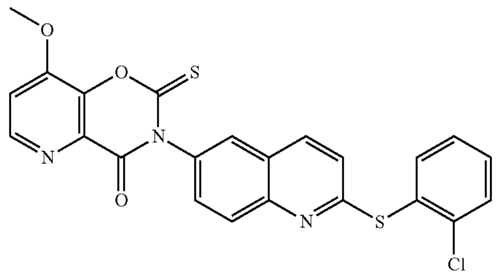 [SMILES: COc1ccnc2c(=O)n(-c3ccc4nc(Sc5ccccc5Cl)ccc4c3)c(=S)oc12] | $^1$H NMR $\delta_H$ (DMSO-d$^6$): 8.61 (d, J = 5.4 Hz, 1H), 8.32 (d, J = 8.8 Hz, 1H), 7.96 (d, J = 2.0 Hz, 1H), 7.91 (d, J = 8.9 Hz, 1H), 7.87 (d, J = 7.7 Hz, 1H), 7.78-7.70 (m, 2H), 7.63-7.57 (m, 2H), 7.54-7.50 (m, 1H), 7.18 (d, J = 8.7 Hz, 1H), 4.10 (s, 3H); LCMS (Method B): 3.25 min, (480.0, MH$^+$). |
| 44 | 3-(2-((2-chloropyridin-3-yl)oxy)quinolin-6-yl)-8-methoxy-2-thioxo-2,3-dihydro-4H-pyrido[2,3-e][1,3]oxazin-4-one 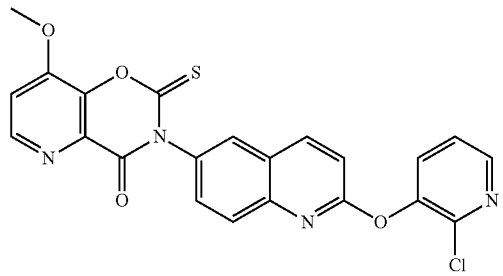 | $^1$H NMR $\delta_H$ (DMSO-d$^6$): 8.61 (d, J = 5.4 Hz, 1H), 8.59 (d, J = 8.7 Hz, 1H), 8.41 (dd, J = 4.7, 1.7 Hz, 1H), 8.05-8.01 (m, 2H), 7.75 (d, J = 8.9 Hz, 1H), 7.68 (dd, J = 8.9, 2.3 Hz, 1H), 7.63 (dd, J = 8.0, 4.7 Hz, 1H), 7.61 (d, J = 5.5 Hz, 1H), 7.50 (d, J = 8.8 Hz, 1H), 4.10 (s, 3H); LCMS (Method B): 3.27 min, (465.0, MH$^+$). |
| 45 | 3-(2-((2-chloropyridin-3-yl)thio)quinolin-6-yl)-8-methoxy-2-thioxo-2,3-dihydro-4H-pyrido[2,3-e][1,3]oxazin-4-one 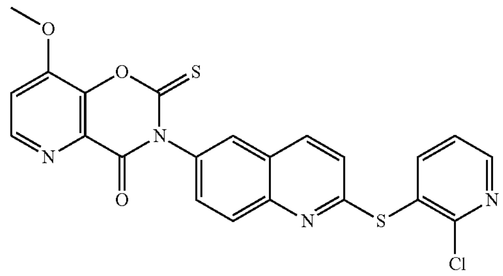 | $^1$H NMR $\delta_H$ (DMSO-d$^6$): 8.62 (d, J = 5.4 Hz, 1H), 8.47-8.40 (m, 2H), 8.10-8.03 (m, 3H), 7.80 (dd, J = 9.1, 2.1 Hz, 1H), 7.64 (d, J = 11.5 Hz, 1H), 7.62 (d, J = 8.4 Hz, 1H), 7.42 (dd, J = 8.1, 4.7 Hz, 1H), 4.10 (s, 3H); LCMS (Method B): 3.41 min, (481.0, MH$^+$). |

-continued

| Example No | Compound | $^1$H NMR/LCMS |
|---|---|---|
| 46 | 3-(2-((2-chloropyridin-3-yl)(methyl)amino)quinolin-6-yl)-8-methoxy-2-thioxo-2,3-dihydro-4H-pyrido[2,3-e][1,3]oxazin-4-one 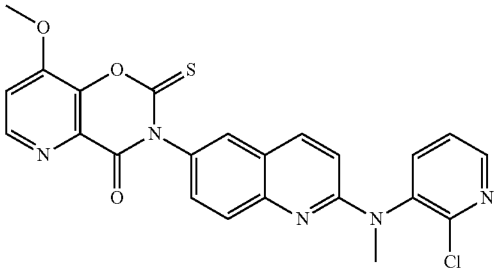 | $^1$H NMR $\delta_H$ (DMSO-d$^6$): 8.61 (d, J = 5.4 Hz, 1H), 8.50 (dd, J = 4.7, 1.8 Hz, 1H), 8.16-8.06 (m, 2H), 7.83-7.74 (m, 2H), 7.65 (dd, J = 7.8, 4.7 Hz, 1H), 7.62-7.54 (m, 2H), 6.64 (d, J = 9.1 Hz, 1H), 4.09 (s, 3H), 3.52 (s, 3H); LCMS (Method B): 3.19 min, (478.0, MH$^+$). |

Example 47: 2-((2-isopropoxyquinolin-6-yl)carbamoyl)-4-methoxypyridin-3-yl acetate

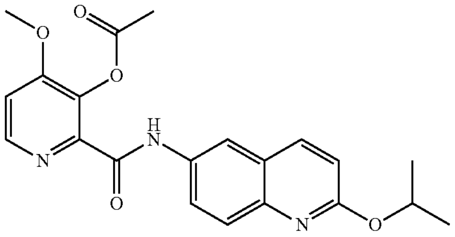 [SMILES: COc1ccnc(C(=O)Nc2ccc3nc(OC(C)C)ccc3c2)c1OC(C)=O]

Following the procedure for Example 17, the title compound was obtained as a light yellow solid (24.5 mg, 94%).

1H NMR $\delta_H$ (400 MHz, DMSO-d6) 10.72 (s, 1H), 8.51 (d, J=5.5 Hz, 1H), 8.40 (s, 1H), 8.18 (d, J=8.9 Hz, 1H), 7.95 (d, J=11.2 Hz, 1H), 7.71 (d, J=8.9 Hz, 1H), 7.46 (d, J=5.5 Hz, 1H), 6.92 (d, J=8.9 Hz, 1H), 5.52-5.39 (m, 1H), 3.94 (s, 3H), 2.31 (s, 3H), 1.36 (d, J=6.2 Hz, 6H).

LCMS (Method B): 3.98 min, (396.2, MH$^+$).

Example 48: Testing the Fungicidal Activity of the Compounds of the Invention

Compounds were screened in 96 well plates with 10 compounds per plate. Each compound was screened using agar amended to 20, 2, 0.2 and 0.02 ppm of the test material. Proline at 50 and 10 ppm and 0.2% DMSO were used respectively as positive and negative controls. Each test concentration and standard were tested twice on a plate.

Compounds were screened against *Zymoseptoria tritici*. The agar used in the test was 1% potato dextrose agar. Sufficient spores were added to the appropriate agar to give 10,000 spores/mL agar.

A ×10 stock solution in 2% DMSO was produced for each dose i.e. 200, 20, 2 and 0.2 ppm, and 10 μl of this added to the appropriate wells on the plate. An equivalent amount of 2% DMSO and Proline stock at 500 and 100 ppm were added for the controls. To each well, 90 μl of the appropriate agar spore suspension was added to give the final well concentrations outlined in the first paragraph.

Plates were incubated at room temperature (18° C.) and assessed after 7 days.

The amount of fungal growth in each well was compared to the DMSO controls and scored according to the following key:

A—EC50<2 ppm

B—2≤EC50<20

C—EC50≥20

D—No activity detected at the highest dose tested

NT—Not tested

The ranking in the table is:

| Example | *Zymoseptoria* |
|---|---|
| 1 | B |
| 2 | A |
| 3 | A |
| 4 | B |
| 5 | A |
| 6 | A |
| 7 | A |
| 8 | A |
| 9 | A |
| 10 | C |
| 11 | A |
| 12 | NT |
| 13 | C |
| 14 | C |
| 15 | B |
| 16 | B |
| 17 | B |
| 18 | B |
| 19 | A |
| 20 | C |
| 21 | C |
| 22 | C |
| 23 | A |
| 24 | C |
| 25 | B |
| 26 | A |
| 27 | C |
| 28 | C |
| 29 | C |
| 30 | B |
| 31 | C |
| 32 | A |
| 33 | C |
| 34 | C |
| 35 | B |
| 36 | C |
| 37 | A |
| 38 | B |
| 39 | C |
| 40 | A |

-continued

| Example | *Zymoseptoria* |
|---|---|
| 41 | C |
| 42 | B |
| 43 | C |
| 44 | C |
| 45 | C |
| 46 | C |
| 47 | A |

The invention claimed is:

1. A compound of formula I, or an agronomically acceptable salt or N-oxide thereof:

I

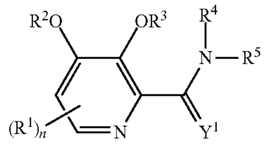

$Y^1$ is O;

$R^1$, $R^{5a}$ and $R^{15}$ are each independently at each occurrence selected from $C_1$-$C_6$-alkyl, $C_1$-$C_6$-haloalkyl, $C_3$-$C_6$-cycloalkyl, halogen, nitro, $OR^{11}$, $SR^{12}$, $OS(O)_2R^{12}$, $S(O)_2R^{12}$, $C(O)OR^{12}$, $C(O)NR^{12}R^{12}$, $C(O)R^{12}$, $S(O)_2NR^{12}R^{12}$, $S(O)(NR^{12})R^{12}$, $S(O)R^{12}$, cyano, $C_2$-$C_6$-alkenyl, $C_2$-$C_6$-alkynyl, and $NR^{12}R^{13}$, $R^2$ and $R^3$ are each independently selected from H, $C_1$-$C_4$-alkyl, $C_3$-$C_6$-cycloalkyl, $C(O)R^{14}$, $C(O)OR^{14}$, $CH_2OC(O)R^{14}$ and $CH_2OC(O)OR^{14}$;

$R^4$ is independently at each occurrence selected from: H, $C_3$-$C_6$-cycloalkyl, $C_1$-$C_6$-alkyl and benzyl;

or $R^3$ and $R^4$ together form a group independently selected from $C_1$-$C_2$-alkylene, —C(O)— and —C(S)—;

$R^5$ is quinoline; wherein $R^5$ is substituted with from 1 to 5 $R^{5a}$ groups and/or a single $Z^1$—$Z^2$—$R^6$ group;

$Z^1$ is independently absent or is $CR^8R^9$;

$Z^2$ is independently absent or is selected from C(O)O, OC(O), O, S, S(O), $S(O)_2$, $C(O)NR^7$, $NR^7C(O)$, $S(O)_2NR^7$, $NR^7S(O)_2$, $S(O)NR^7$, $NR^7S(O)$, $CR^8R^9$, C(O), C(S), C═$NOR^{10}$, and $NR^7$;

$R^6$ is independently at each occurrence selected from $C_3$-$C_8$-alkyl and $C_0$-$C_3$-alkylene-$R^{6a}$, wherein $R^{6a}$ is independently at each occurrence selected from phenyl, 5- or 6-membered heteroaryl, 5-, 6-, 7- or 8-membered heterocycloalkyl and $C_5$-$C_8$-cycloalkyl; said heterocycloalkyl or cycloalkyl group being monocyclic or bicyclic; said heteroaryl or phenyl group being optionally substituted with from 1 to 5 $R^{15}$ groups or said heterocycloalkyl or cycloalkyl group being optionally substituted with from 1 to 4 $R^{16}$ groups;

$R^{16}$ is independently at each occurrence selected from: ═O, ═S, $C_1$-$C_6$-alkyl, $C_1$-$C_6$-haloalkyl, $C_3$-$C_6$-cycloalkyl; halogen, nitro, $OR^{11}$, $SR^{12}$, $OS(O)_2R^{12}$, $S(O)_2R^{12}$, $S(O)_2NR^{12}R^{12}$, $S(O)(NR^{12})R^{12}$, $S(O)R^{12}$, cyano, $C_2$-$C_6$-alkenyl, $C_2$-$C_6$-alkynyl, and $NR^{12}R^{13}$;

$R^7$ and $R^{12}$ are each independently at each occurrence selected from: H, $C_3$-$C_6$-cycloalkyl, $C_1$-$C_6$-alkyl and benzyl;

or where two $R^{12}$ groups are attached to the same nitrogen atom, said $R^{12}$ groups, together with said nitrogen atom form a 4-, 5-, 6- or 7-membered heterocycloalkyl ring;

$R^8$ is independently at each occurrence selected from: H, $C_3$-$C_6$-cycloalkyl, $C_1$-$C_6$-alkyl, phenyl and 5- or 6-membered heteroaryl;

$R^9$ is independently at each occurrence selected from: H, halo and $OR^{10}$;

or $R^8$ and $R^9$ together with the carbon atom to which they are attached may form a $C_3$-$C_6$-cycloalkyl ring or a 3-, 4-, 5- or 6-membered heterocycloalkyl ring;

$R^{10}$ is each independently at each occurrence selected from: H, $C_3$-$C_6$-cycloalkyl, $C_1$-$C_6$-alkyl and $C_1$-$C_3$-alkylene-$R^{10a}$, wherein $R^{10a}$ is independently at each occurrence selected from phenyl and 5- or 6-membered heteroaryl;

$R^{11}$ is independently at each occurrence selected from: H, $C_1$-$C_0$-alkyl, $C_3$-$C_6$-cycloalkyl, C(O)—$C_1$-$C_6$-alkyl and $C_1$-$C_6$-haloalkyl;

$R^{13}$ is independently at each occurrence selected from; H, $C_1$-$C_6$-alkyl, C(O)—$C_1$-$C_6$-alkyl and $S(O)_2$-$C_1$-$C_6$-alkyl;

or where an $R^{12}$ group and an $R^{13}$ group are attached to the same nitrogen atom, said $R^{12}$ and $R^{13}$ groups, together with said nitrogen atom form a 4-, 5-, 6- or 7-membered heterocycloalkyl ring;

$R^{14}$ is independently at each occurrence: $C_1$-$C_6$-alkyl, phenyl, benzyl and $C_3$-$C_6$-cycloalkyl;

n is independently an integer selected from 0, 1 and 2; and wherein any aforementioned alkyl, alkylene, alkenyl, cycloalkyl, heterocycloalkyl (including where two $R^{12}$ groups or an $R^{12}$ group and an $R^{13}$ group together with a nitrogen to which they are attached form a heterocycloalkyl ring), alkynyl, C(O)-alkyl, $S(O)_2$-alkyl and benzyl is optionally substituted, where chemically possible, by 1 to 4 substituents which are each independently selected at each occurrence from the group consisting of: ═O; ═$NR^a$, ═$NOR^a$, $C_1$-$C_4$-alkyl, halo, nitro, cyano, $C_1$-$C_4$-haloalkyl, $C_2$-$C_4$-alkenyl, $C_2$-$C_4$-alkynyl, $NR^aR^b$, $S(O)_2R^a$, $S(O)R^a$, $S(O)(NR^a)R^a$, $S(O)_2NR^aR^a$, $CO_2R^a$, $C(O)R^a$, $CONR^aR^a$, $OR^a$ and $SR^a$;

wherein $R^a$ is independently selected from H and $C_1$-$C_4$-alkyl; and $R^b$ is independently selected from H, $C_1$-$C_4$-alkyl, C(O)—$C_1$-$C_4$-alkyl and $S(O)_2$-$C_1$-$C_4$-alkyl.

2. A compound of claim 1, wherein n is 0.

3. A compound of claim 1, wherein $R^2$ is independently selected from $C_1$-$C_4$-alkyl and $C_3$-$C_6$-cycloalkyl.

4. A compound of claim 1, wherein $R^3$ is independently selected from H, $C(O)R^{14}$, $C(O)OR^{14}$, $CH_2OC(O)R^{14}$ and $CH_2OC(O)OR^{14}$.

5. A compound of claim 1, wherein $R^4$ is H.

6. A compound of claim 1, wherein $R^3$ and $R^4$ together form a group independently selected from $C_1$-$C_2$-alkylene, —C(O)— and —C(S)—.

7. A compound of claim 1, wherein $R^5$ has the structure

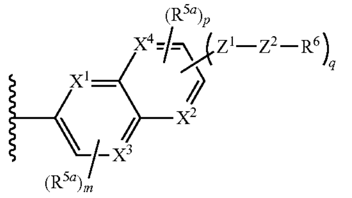

wherein a single one of $X^1$, $X^2$, $X^3$ and $X^4$ is nitrogen and the other three of $X^1$, $X^2$, $X^3$ and $X^4$ are carbon; m is independently an integer selected from 0, 1, 2 and 3; p is independently an integer selected from 0, 1, 2, 3 and 4; and q is independently an integer selected from 0 and 1.

8. A compound of claim 7, wherein q is 1.

9. A compound of claim 8, wherein $R^5$ has the structure:

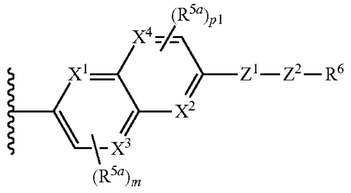

wherein a single one of $X^1$, $X^2$, $X^3$ and $X^4$ is nitrogen and the other three of $X^1$, $X^2$, $X^3$ and $X^4$ are carbon; m is independently an integer selected from 0, 1, 2 and 3; and p1 is independently an integer selected from 0, 1, 2 and 3.

10. A compound of claim 8, wherein $R^5$ has the structure:

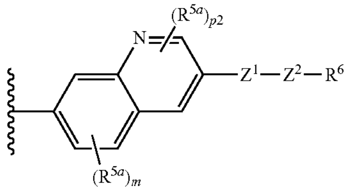

wherein m is independently an integer selected from 0, 1, 2 and 3; and p2 is independently an integer selected from 0, 1 and 2.

11. A compound of claim 8, wherein $R^5$ has the structure:

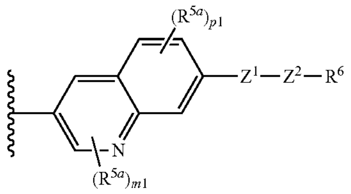

wherein m1 is independently an integer selected from 0, 1 and 2; and p1 is independently an integer selected from 0, 1, 2 and 3.

12. A compound of claim 8, wherein $Z^1$ is absent.

13. A compound of claim 8, wherein $Z^2$ is independently selected from $NR^7$, S, and O.

14. A compound of claim 8, wherein $Z^2$ is independently absent.

15. A compound of claim 8, wherein $Z^2$ is $CR^8R^9$.

16. A compound of claim 8, wherein $R^6$ is $R^{6a}$.

17. A compound of claim 16, wherein $R^{6a}$ has the structure:

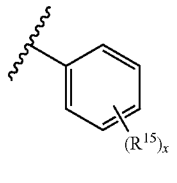

wherein x is an integer selected from 0, 1, 2, 3, 4 and 5.

18. A compound of claim 13, wherein $R^6$ is $C_3$-$C_8$-alkyl.

19. A compound of claim 1, wherein the compound of formula (I) is selected from the group consisting of:

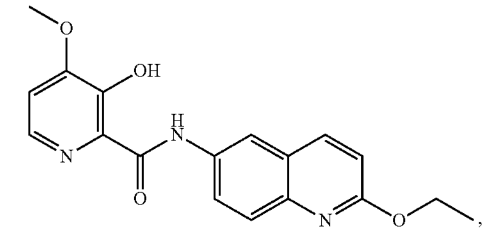

,

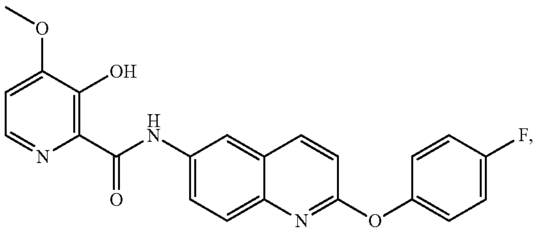

,

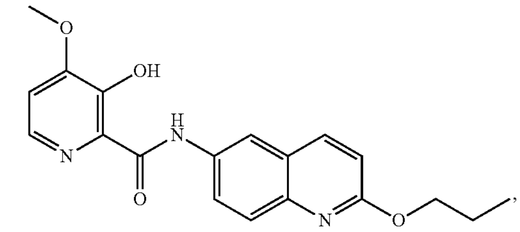

,

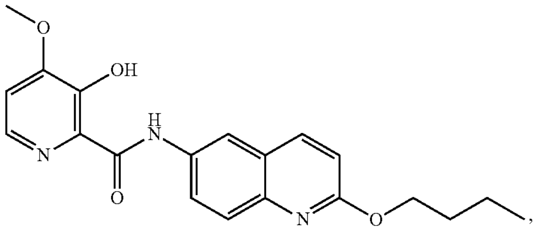

,

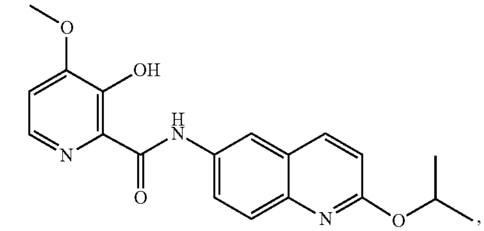

,

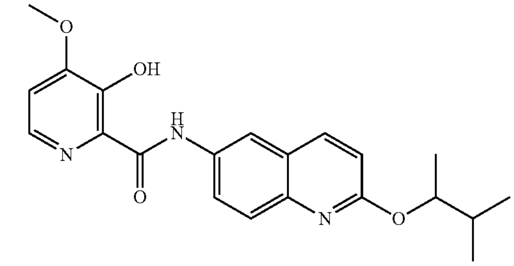

,

-continued
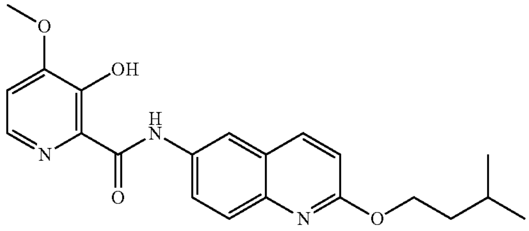
,
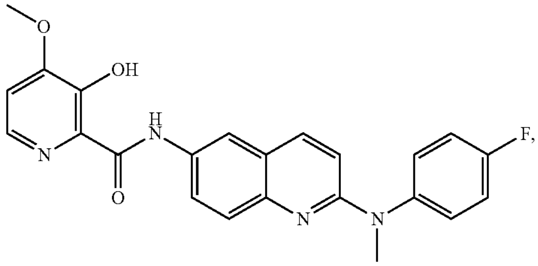
,
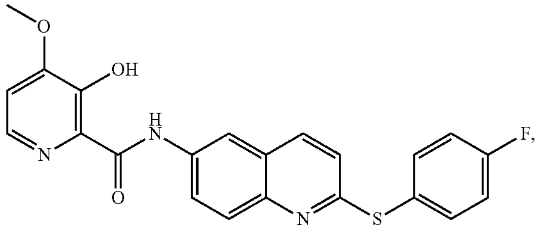
,
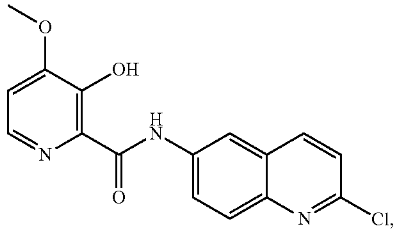
,
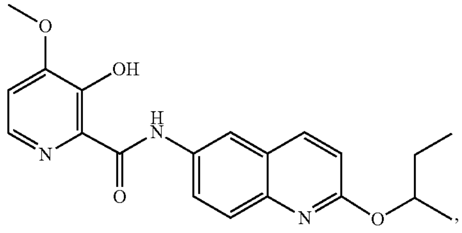
,
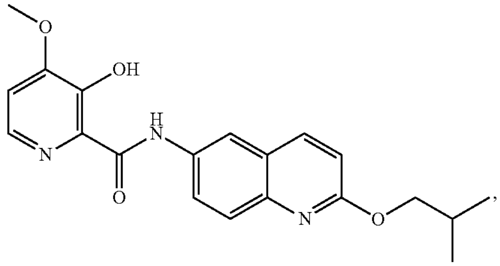
,
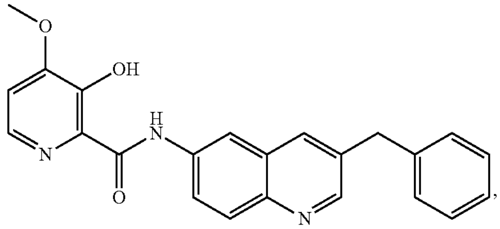
,
-continued
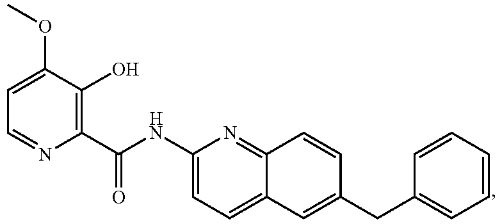
,
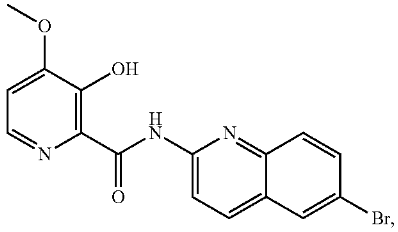
,
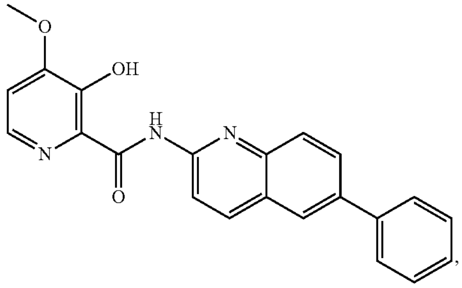
,
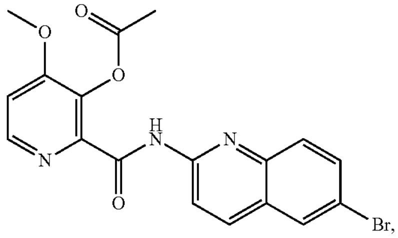
,
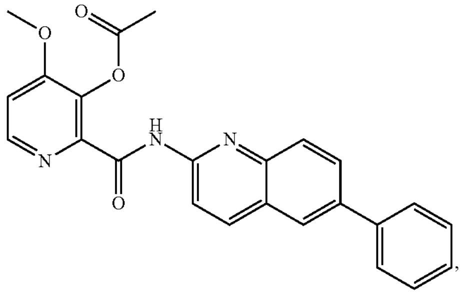
,
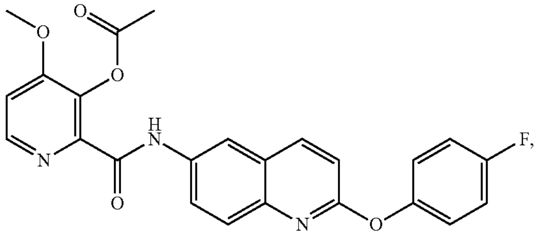
, -continued
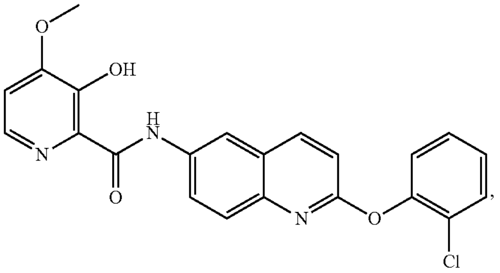
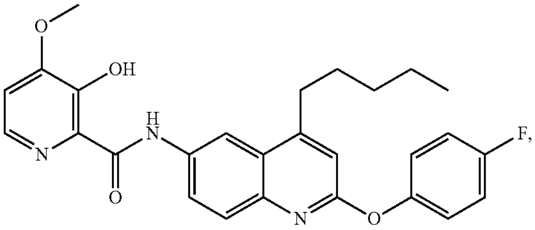
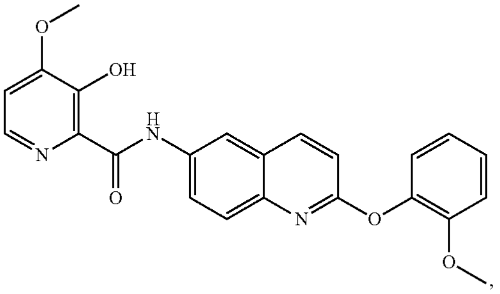
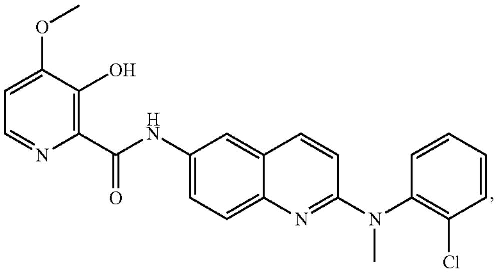
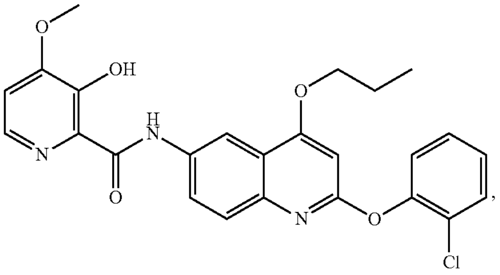
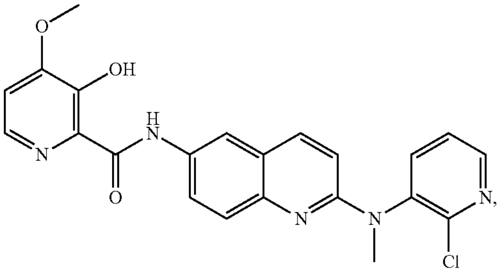
-continued
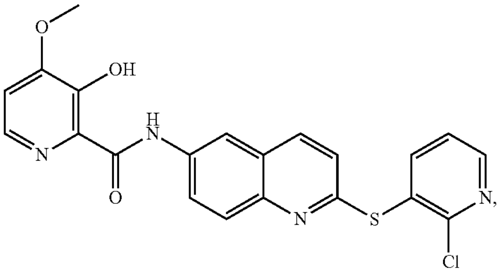
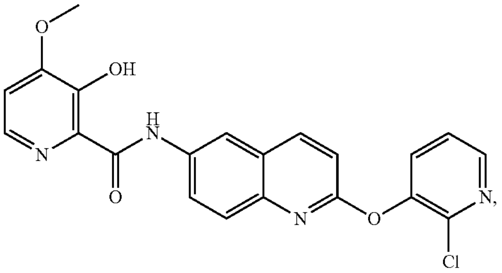
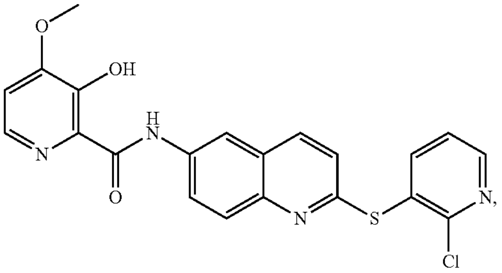
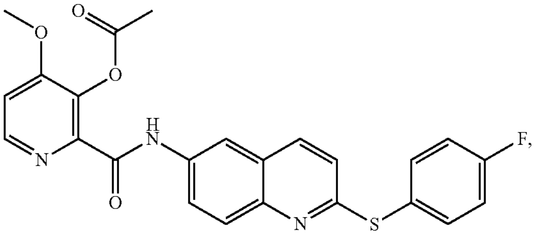
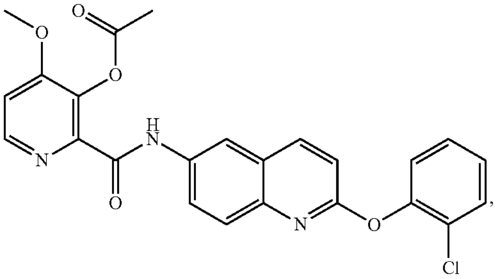
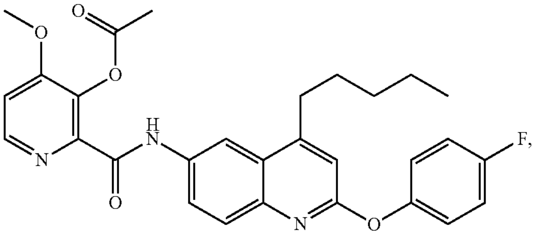

-continued
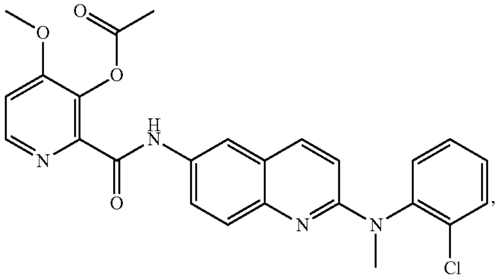
,
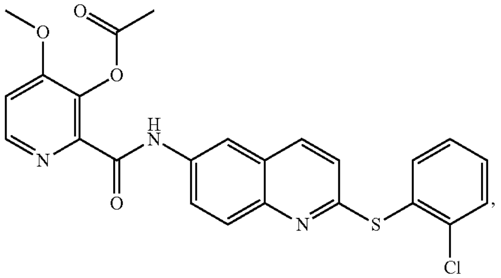
,
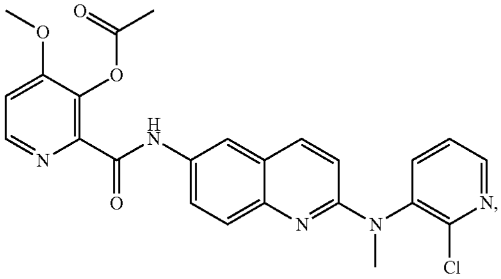
,
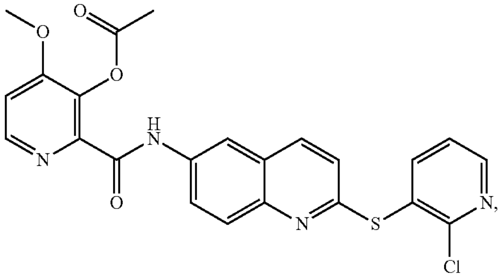
,
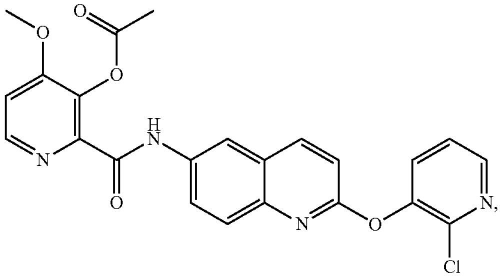
,
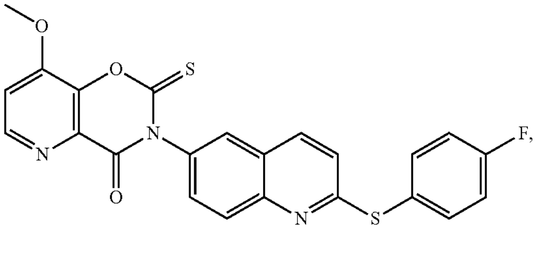
,
-continued
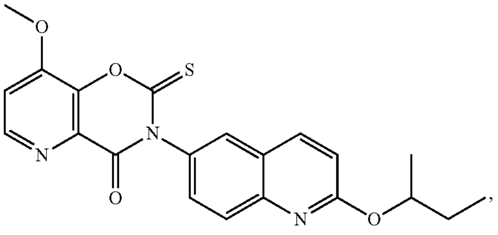
,
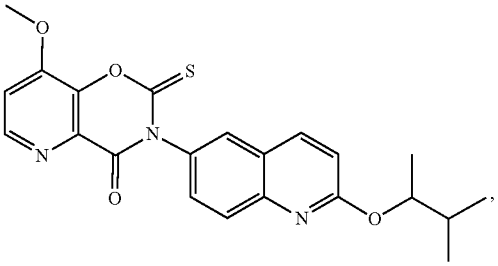
,
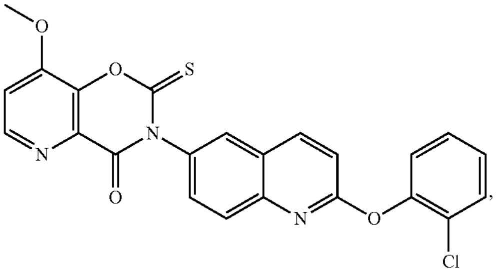
,
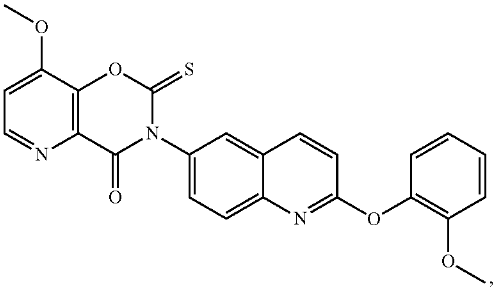
,
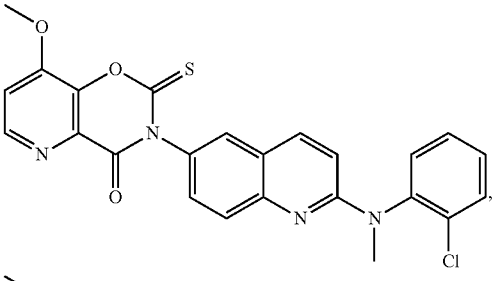
,
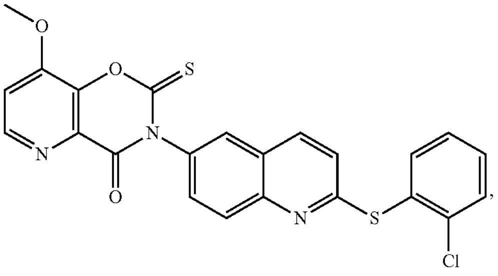
, -continued

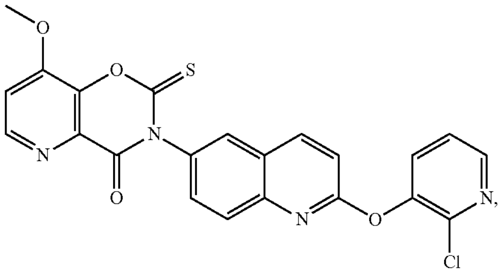

,

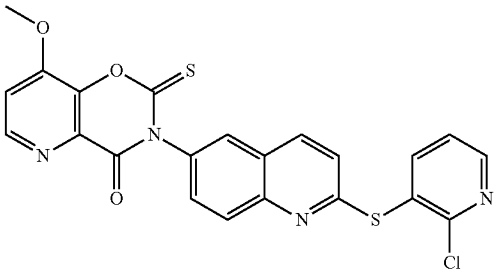

and

-continued

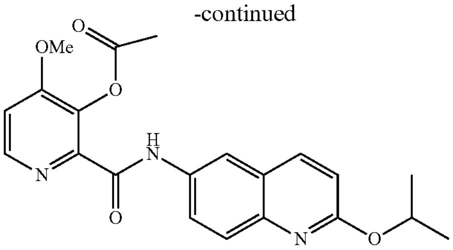

.

20. A method for controlling a fungal disease of a plant, the method comprising applying an agronomically effective and substantially non-phytotoxic quantity of a compound of claim 1 to seeds of the plant, to the plant or to a growing medium for the plant.

21. A fungicidal composition comprising an effective and non-phytotoxic amount of an active compound of claim 1.

22. A compound of claim 6, wherein $R^3$ and $R^4$ together form-C(S)—.

23. The method of claim 20, wherein the fungal disease is a Septoria disease.

24. The method of claim 23, wherein the Septoria disease is caused by *Zymoseptoria tritici*.

* * * * *